(12) United States Patent
Senior et al.

(10) Patent No.: US 12,374,428 B2
(45) Date of Patent: Jul. 29, 2025

(54) DETERMINING PROTEIN DISTANCE MAPS BY COMBINING DISTANCE MAPS CROPS

(71) Applicant: DeepMind Technologies Limited, London (GB)

(72) Inventors: Andrew W. Senior, London (GB); James Kirkpatrick, London (GB); Laurent Sifre, Paris (FR); Richard Andrew Evans, London (GB); Hugo Penedones, Zurich (CH); Chongli Qin, London (GB); Ruoxi Sun, Mountain View, CA (US); Karen Simonyan, London (GB); John Jumper, London (GB)

(73) Assignee: DeepMind Technologies Limited, London (GB)

( * ) Notice: Subject to any disclaimer, the term of this patent is extended or adjusted under 35 U.S.C. 154(b) by 1081 days.

(21) Appl. No.: 17/266,689

(22) PCT Filed: Sep. 16, 2019

(86) PCT No.: PCT/EP2019/074674
§ 371 (c)(1),
(2) Date: Feb. 8, 2021

(87) PCT Pub. No.: WO2020/058176
PCT Pub. Date: Mar. 26, 2020

(65) Prior Publication Data
US 2021/0407625 A1  Dec. 30, 2021

Related U.S. Application Data

(60) Provisional application No. 62/770,490, filed on Nov. 21, 2018, provisional application No. 62/734,773, (Continued)

(51) Int. Cl.
*G16B 40/20* (2019.01)
*G06F 18/2413* (2023.01)
(Continued)

(52) U.S. Cl.
CPC ....... *G16B 40/20* (2019.02); *G06F 18/24147* (2023.01); *G06N 3/044* (2023.01);
(Continued)

(58) Field of Classification Search
None
See application file for complete search history.

(56) References Cited

U.S. PATENT DOCUMENTS

2008/0215301 A1  9/2008  Eyal et al.
2013/0303383 A1  11/2013  Sander et al.
(Continued)

FOREIGN PATENT DOCUMENTS

CN  101294970  10/2008
CN  101647022  2/2010
(Continued)

OTHER PUBLICATIONS

Gao, Y., Wang, S., Deng, M. and Xu, J., Jan. 17, 2018. RaptorX-Angle: real-value prediction of protein backbone dihedral angles through a hybrid method of clustering and deep learning. BMC bioinformatics, 19, pp. 73-84. (Year: 2018).*
(Continued)

*Primary Examiner* — Karlheinz R. Skowronek
*Assistant Examiner* — Meredith Abbott Vassell
(74) *Attorney, Agent, or Firm* — Fish & Richardson P.C.

(57) ABSTRACT

Methods, systems, and apparatus, including computer programs encoded on a computer storage medium, for performing protein structure prediction. In one aspect, a method comprises generating a distance map for a given protein, wherein the given protein is defined by a sequence of amino
(Continued)

acid residues arranged in a structure, wherein the distance map characterizes estimated distances between the amino acid residues in the structure, comprising: generating a plurality of distance map crops, wherein each distance map crop characterizes estimated distances between (i) amino acid residues in each of one or more respective first positions in the sequence and (ii) amino acid residues in each of one or more respective second positions in the sequence in the structure of the protein, wherein the first positions are a proper subset of the sequence; and generating the distance map for the given protein using the plurality of distance map crops.

20 Claims, 19 Drawing Sheets

Related U.S. Application Data filed on Sep. 21, 2018, provisional application No. 62/734,757, filed on Sep. 21, 2018.

(51) Int. Cl.
   *G06N 3/044*     (2023.01)
   *G06N 3/045*     (2023.01)
   *G06N 3/047*     (2023.01)
   *G06N 3/08*      (2023.01)
   *G06N 20/00*     (2019.01)
   *G16B 15/20*     (2019.01)
   *G16H 10/40*     (2018.01)

(52) U.S. Cl.
   CPC ............. *G06N 3/045* (2023.01); *G06N 3/047* (2023.01); *G06N 3/08* (2013.01); *G16B 15/20* (2019.02); *G16H 10/40* (2018.01); *G06N 20/00* (2019.01)

(56) References Cited

U.S. PATENT DOCUMENTS

| | | |
|---|---|---|
| 2013/0304432 A1 | 11/2013 | Sander et al. |
| 2016/0077112 A1 | 3/2016 | Jara et al. |
| 2017/0249420 A1 | 8/2017 | Saladi et al. |
| 2017/0316147 A1 | 11/2017 | Gao et al. |
| 2017/0372004 A1 | 12/2017 | Henriksen et al. |

FOREIGN PATENT DOCUMENTS

| | | |
|---|---|---|
| CN | 101794351 | 8/2010 |
| CN | 105046106 | 11/2015 |
| CN | 105468934 | 4/2016 |
| CN | 105740646 | 7/2016 |
| CN | 105808972 | 7/2016 |
| CN | 106372456 | 2/2017 |
| CN | 106503484 | 3/2017 |
| CN | 107330512 | 11/2017 |
| CN | 107506613 | 12/2017 |
| CN | 107622182 | 1/2018 |
| EP | 1482433 | 12/2004 |
| EP | 2728000 | 5/2014 |
| IN | 201641028573 | 2/2018 |
| JP | 1995152775 | 6/1995 |
| JP | H07-152775 | 6/1995 |
| JP | 2004258814 | 9/2004 |
| JP | 2017530373 | 10/2017 |
| KR | 20110112664 | 10/2011 |
| WO | WO 0214875 | 2/2002 |
| WO | WO 2017/062382 | 4/2017 |

OTHER PUBLICATIONS

Office Action in Canadian Appln. No. 3,110,200, dated Feb. 9, 2022, 5 pages.

Office Action in Canadian Appln. No. 3,110,242, dated Feb. 9, 2022, 5 pages.

Office Action in Canadian Appln. No. 3,110,395, dated Feb. 9, 2022, 4 pages.

Zhao et al., "A Position-Specific Distance-Dependent Statistical Potential for Protein Structure and Functional Study," Structure, Jun. 2012, 20(6):118-1126.

Office Action in Chinese Appln. No. 201980054190.6, dated Sep. 1, 2023, 18 pages (with English translation).

Zhang, "The Research and Establishment of Algorithm Model of the Protein Spatial Structure Similarity," Thesis for the degree of Master, Zhengzhou University, School of Electrical Engineering, May 2016, 80 pages (with English abstract).

Abagyan et al., "ICM—a new method for protein modeling and design: applications to docking and structure prediction from the distorted native conformation," J Comput Chem., May 1994, 15(5):488-506.

Altschuh et al., "Correlation of co-ordinated amino acid substitutions with function in viruses related to tobacco mosaic virus," J. Mol. Biol., Feb. 1987, 193(4):693-707.

Altschul et al., "Gapped BLAST and PSI-BLAST: a new generation of protein database search programs," Nucleic Acids Res., Sep. 1997, 25(17):3389-3402.

Aszodi et al., "Estimating polypeptide a-carbon distances from multiple sequence alignments," J. Math. Chem., Jun. 1995, 17(2):167-184.

Aszodi et al., "Global fold determination from a small No. of distance restraints," J. Mol. Biol., Aug. 1995, 251(2):308-326.

Bohr et al., "A novel approach to prediction of the 3-dimensional structures of protein backbones by neural networks," FEBS Letters, Feb. 1990, 261(1):43-46.

Bohr et al., "Protein Structures from Distance Inequalities," Journal of Molecular Biology, Jun. 1993, 231(3):861-869.

Boomsma et al., "A generatiye, probabilistic model of local protein structure," PNAS, Jul. 2008, 105(26):26:8932-8937.

Clevert et al., "Fast and Accurate Deep Network Learning by Exponential Linear Units (ELUs)," CoRR, Nov. 2015, arXiv:1511.07289, 14 pages.

Cong et al., "An automatic method for CASP9 free modeling structure prediction assessment," Bioinformatics, Dec. 2011, 27(24):3371-3378.

Conway et al., "Relaxation of backbone bond geometry improves protein energy landscape modeling, " Protein Sci., Oct. 2013, 23(1):47-55.

Das et al., "Macromolecular modeling with Rosetta," Annu. Rev. Biochem., Jul. 2008, 77:363-382.

Dawson et al., "CATH: An expanded resource to predict protein function through structure and sequence," Nucleic Acids Res., Jan. 2017, 45(D1):D289-D295.

Derevyanko et al., "Deep convolutional networks for quality assessment of protein folds," Bioinformatics, Dec. 2018, 34(23):4046-4053.

Dill et al., "The protein folding problem," Annu. Rev. Biophys., Jun. 2008, 37:289-316.

Dill et al., "The protein-folding problem, 50 years on," Science, Nov. 2012, 338(6110):1042-1046.

Ekeberg et al., "Improved contact prediction in proteins: Using pseudolikelihoods to infer Potts models," Physical Review E., 87(1):012707.

Fan et al., "Virtual Ligand Screening Against Comparative Protein Structure Models," Methods in Molecular Biology, Nov. 2011, 819:105-126.

Feig, "Computational protein structure refinement: almost there, yet still so far to go," Computational protein structure refinement, Mar. 2017, 7(3):e1307.

Fredholm et al., "A Novel Approach to Prediction of the 3-Dimensional Structures of Protein Backbones by Neural Networks," Advances in Neural Information Processing Systems, 1990, 3:523-9.

Gilliland et al., "The Protein Data Bank," Nucleic Acids Res., Jan. 2000, 28(1):235-242.

Gregor et al., "DRAW: a recurrent neural network for image generation," CoRR, Feb. 2015, arxiv:1502.04623v2, 10 pages.

(56) References Cited

OTHER PUBLICATIONS

Gregor et al., "Towards conceptual compression," CoRR, Apr. 2016, arxiv.org/abs/1604.08772, 14 pages.

Hamelryck et al., "Sampling realistic protein conformations using local structural bias," PLoS Comput. Biol., Sep. 2006, 2(9):e131.

Hastings, "Monte Carlo sampling methods using Markov chains and their applications," Biometrika, Apr. 1970, 57(1):97-109.

He et al., "Deep Residual Learning for Image Recognition," Proceedings of the IEEE Conference on Computer Vision and Pattern Recognition, 2016, pp. 770-778.

Jaderberg et al., "Population based training of neural networks," arXiv:1711.09846, Nov. 2017, 21 pages.

Jones et al., "High precision in protein contact prediction using fully convolutional neural networks and minimal sequence features," Bioinformatics 2018, 34(19):3308-3315.

Jones et al., "MetaPSICOV: Combining coevolution methods for accurate prediction of contacts and long range hydrogen bonding in proteins," Bioinformatics 2015, 31(7):999-1006.

Jones et al., "Predicting novel protein folds by using FRAGFOLD," Proteins: Structure, Function, and Bioinformatics, Jan. 2002, 45(S5):127-132.

Jones et al., "PSICOV: Precise structural contact prediction using sparse inverse covariance estimation on large multiple sequence alignments," Bioinformatics 28(2):184-190.

Kabsch et al., "Dictionary of protein secondary structure: pattern recognition of hydrogen-bonded and geometrical features," Biopolymers, 1983, 22:2577-2637.

Kandathil et al., "DMPfold: a new deep learning-based method for protein tertiary structure prediction and mode refinement," CASP13 Abstracts, Dec. 2018, pp. 84-85.

Kirkpatrick et al., "Optimization by simulated annealing," Science, May 1983, 220(4598):671-680.

Kirkwood, "Statistical mechanics of fluid mixtures," J. Chem. Phys., 1935, 3:300-313.

Konagurthu et al., "Minimum message length inference of secondary structure from protein coordinate data. Bioinformatics," ISMB, 2012, 28:i97-i105.

Kulkic et al., "Toward an accurate prediction of inter-residue distances in proteins using 2D recursive neural networks," Bioinformatics, Jan. 2014, 15(6):15 pages.

Liu et al., "On the limited memory BFGS method for large scale optimization," Math. Program., Aug. 1989, 45(1-3):503-528.

Mariani et al., "IDDT: a local superposition-free score for comparing protein structures and models using distance difference tests," Bioinformatics, 29(21):2722-2728.

Metropolis et al., "Equation of state calculations by fast computing machines," J. Chem. Phys., 1953, 21(6):1087-1092.

Mirdita et al., "Uniclust databases of clustered and deeply annotated protein sequences and alignments," Nucleic Acids Res., 45(D1):D170-D176.

Morcos et al., "Direct-coupling analysis of residue coevolution captures native contacts across many protein families," PNAS, Dec. 2011, 108(49):E1293-E1301.

Moult et al., "Critical assessment of methods of protein structure prediction (CASP)—Round XII," Proteins: Structure, Function, and Bioinformatics, Feb. 2018, 82:1-6.

O'Meara et al., "Combined covalent-electrostatic model of hydrogen bonding improves structure prediction with Rosetta," J. Chem. Theory Comput., 11(2):609-622.

Oord et al., "Wavenet: A generative model for raw audio," arXiv preprint arXiv:1609.03499, 2016, 15 pages.

Ovchinnikov et al., "Improved de novo structure prediction in CASP by incorporating coevolution information into Rosetta," Proteins: Structure, Function, and Bioinformatics, Sep. 2016, 84(S1):67-75.

Ovchinnikov et al., "Robust and accurate prediction of residue-residue interactions across protein interfaces using evolutionary information," Elife, May 2014, 3:e02030.

PCT International Preliminary Report on Patentability in International Appln. No. PCT/EP2019/074670, dated Apr. 1, 2021, 18 pages.

PCT International Preliminary Report on Patentability in International Appln. No. PCT/EP2019/074674, dated Apr. 1, 2021, 17 pages.

PCT International Preliminary Report on Patentability in International Appln. No. PCT/EP2019/074676, dated Apr. 1, 2021, 17 pages.

PCT International Search Report and Written Opinion in International Appln. No. PCT/EP2019/074670, dated Dec. 5, 2019, 26 pages.

PCT International Search Report and Written Opinion in International Appln. No. PCT/EP2019/074674, dated Dec. 13, 2019, 24 pages.

PCT International Search Report and Written Opinion in International Appln. No. PCT/EP2019/074676, dated Dec. 16, 2019, 23 pages.

Quraishi, "End-to-end di erentiable learning of protein structure," Cell Systems, Apr. 2019, 8(4):292-301.e3.

Reczko et al., "Recurrent Neural Networks for Protein Distance Matrix Prediction," Protein Structure by Distance Analysis, Dec. 1994, pp. 87-97.

Remmert et al., "HHblits: lightning-fast iterative protein sequence searching by HMM-HMM alignment," Nature Methods, Feb. 2012, 9(2):173-178.

Rezende et al., "Stochastic backpropagation and approximate inference in deep generative models," Proceedings of the 31st International Conference on Machine Learning, 2014, 32(2):1278-1286.

Sali et al., "Comparative Protein Modelling by Satisfaction of Spatial Restraints," Journal of Molecular Biology, Dec. 1993, 234(3):779-815.

Schaarschmidt et al., "Assessment of contact predictions in CASP12: Co-evolution and deep learning coming of age," Proteins: Structure, Function, and Bioinformatics, Oct. 2017, 86(S1):51-66.

Seemayer et al., "CCMpred: fast and precise prediction of protein residue-residue contacts from correlated mutations," Bioinformatics, Nov. 2014, 30(21):3128-3130.

Shrestha et al., "Improving fragment quality for de novo structure prediction," Proteins: Structure, Function, and Bioinformatics, Apr. 2014, 82(9):2240-2252.

Silver et al., "Mastering the game of go without human knowledge," Nature, Oct. 2017, 550:354-359.

Simons et al., "Assembly of Protein Tertiary Structures from Fragments with Similar Local Sequences using Simulated Annealing and Bayesian Scoring Functions," J. Mol. Biol., Apr. 1997, 268(1):209-225.

Soding et al., "The HHpred interactive server for protein homology detection and structure prediction," Nucleic Acids Research, Jul. 2005, 33(suppl 2):W244-W248.

Uziela et al., "ProQ3D: improved model quality assessments using deep learning," Bioinformatics, Jan. 2017, 33(10):1578-1580.

Van den Oord et al., "Wavenet: A Generative Model for Raw Audio," CoRR, Sep. 2016, arxiv.org/abs/1609.03499, 15 pages.

Wang et al., "Accurate De Novo Prediction of Protein Contact Map by Ultra-Deep Learning Model," PLoS Computational Biology, Jan. 2017, 13(1):e1005324.

Xu, "Distance-based Protein Folding Powered by Deep Learning," PNAS, Aug. 2019, 116(34):16856-16865.

Xu, "Protein structure modeling by predicted distance instead of contacts," CASP13 Abstracts, Dec. 2018, pp. 146-147.

Yang et al., "Sixty-five years of the long march in protein secondary structure prediction: the final stretch?," Briefings Bioinf., 2018, 19(3):482-494.

Yu et al., "Multi-scale context aggregation by dilated convolutions," arXiv:1511.07122, Apr. 2016, 13 pages.

Zemla et al., "Processing and analysis of CASP3 protein structure predictions," Proteins: Structure, Function, and Genetics, 1999, 3:22-29.

Zhang et al., "Contact map prediction by deep residual fully convolutional neural network with only evolutionary coupling features derived from deep multiple sequence alignment," CASP13 Abstracts, Dec. 2018, pp. 181-182.

(56) References Cited

OTHER PUBLICATIONS

Zhang et al., "Scoring function for automated assessment of protein structure template quality," Proteins, Oct. 2004, 57(4):702-710.
Zhang et al., "Template-based and free modeling of I-TASSER and QUARK pipelines using predicted contact maps in CASP12," Proteins, Mar. 2018, 86(S1):136-151.
Zhao et al., "A Position-Specific Distance-Dependent Statistical Potential for Protein Structure and Functional Study," Structure, Jun. 2012, 20(6):1118-1126.
Zhu et al., "Protein threading using residue co-variation and deep learning," Bioinformatics, Jul. 2018, 34(13):i263-i273.
Decision to Grant Patent in Japanese Appln. No. 2021-509152, dated Jul. 19, 2024, 6 pages (with English translation).
Extended Search Report in European Appln. No. 24180923.5, dated Sep. 12, 2024, 17 pages.
Ferreira, Leonardo G., et al. "Molecular docking and structure-based drug design strategies." Molecules 20.7 (2015): 13384-13421. (Year: 2015).
Watanabe et al., "An attempt to predict the three-dimensional structure of a protein using a neural network," Proceedings for nationwide lecture meeting (1) Architecture, Software science and engineering, Database and media, Apr. 2, 2007, 289-290 (with English machine translation).
Deng et al., "Protein Structure Prediction," Int. J. Mod. Phys. B, Jul. 2018, 32(18):18 pages.
Kikuchi, "Development of genome sequence analysis methods using Kikuchi-shi, average distance statistics between amino acids of proteins," Kurashiki University of Science and the Arts, 2008, pp. 184-186 (with English abstract).
Matsunaga, "Conformational Transmistion Pathways in Proteins Explored by the String Method," Proceedings of the Institute of Statistical Mathematics, 2014, 62(2):285-299 (with English abstract).
Office Action in Japanese Appln. No. 2021-509152, dated Mar. 28, 2022, 7 pages (with English translation).
Office Action in Japanese Appln. No. 2021-509189, dated Mar. 28, 2022, 6 pages (with English translation).
Office Action in Japanese Appln. No. 2021-509217, dated Mar. 28, 2022, 8 pages (with English translation).
Office Action in Japanese Appln. No. 2022-130054, dated Jul. 10, 2023, 5 pages.
Al-Lazikani et al., "Protein structure prediction," Current Opinion in Chemical Biology, 2001, 5:51-56.
Boomsma et al., "A generative, probabilistic model of local protein structure," PNAS, Jul. 1, 2008, 105(26):8932-8937.
Office Action in Chinese Appln. No. 201980054143.1, dated Dec. 19, 2023, 29 pages (with English translation).
Office Action in Chinese Appln. No. 201980054171.3, dated Dec. 28, 2023, 34 pages (with English translation).
Office Action in European Appln. No. 19769469.8, dated Dec. 1, 2023, 8 pages.
Senior et al., "Protein structure prediction using multiple deep neural networks in the 13th Critical Assessment of Protein Structure Prediction (CASP13)," Proteins: Structure, Function, and Bioinformatics, Oct. 10, 2019, 87(12):1141-1148.
Sheng et al., "Distance constrains model based hybrid monte carlo sampling algorithm in protein structure prediction," Chinese Journal of Bioinformatics, Jun. 2016, 14(2):6 pages (with English abstract).
Wang et al., "New Deep Neural Networks for Protein Model Evaluation," 2017 International Conference on Tools with Artificial Intelligence, Nov. 6, 2017, pp. 309-313.
Decision to Grant Patent in Japanese Appln. No. 2022-130054, dated Oct. 23, 2023, 5 pages (with English translation).
Decision to Grant a Patent in Japanese Appln. No. 2021-509152, dated Jul. 19, 2022, 6 pages.
Decision to Grant a Patent in Japanese Appln. No. 2021-509189, dated Aug. 1, 2022, 5 pages.
Decision to Grant a Patent in Japanese Appln. No. 2021-509217, dated Jul. 19, 2022, 5 pages.
Evans et al., "De novo structure prediction with deep-learning based scoring," ResearchGate, Dec. 2018, 3 pages.
Notice of Allowance in Chinese Appln. No. 201980054190.6, dated May 15, 2024, 6 pages (with English translation).
Office Action in Chinese Appln. No. 201980054171.3, dated May 17, 2024, 14 pages (with English translation).
Office Action in Indian Appln. No. 202127003862, dated Jan. 7, 2022, 9 pages (with English translation).
Office Action in Indian Appln. No. 202127004079, dated Jan. 19, 2022, 6 pages (with English translation).

* cited by examiner

DETERMINING PROTEIN DISTANCE MAPS BY COMBINING DISTANCE MAPS CROPS

CROSS-REFERENCE TO RELATED APPLICATION

This application is a National Stage Application under 35 U.S.C. § 371 and claims the benefit of International Application No. PCT/EP2019/074674, filed Sep. 16, 2019, which claims priority to U.S. Application No. 62/770,490, filed Nov. 21, 2018, U.S. Application No. 62/734,773, filed Sep. 21, 2018, and U.S. Application No. 62/734,757, filed Sep. 21, 2018, the disclosures of which are incorporated herein by reference.

BACKGROUND

This specification relates to determining protein structures.

A protein consists of a sequence of amino acids. An amino acid is an organic compound which includes an amino functional group and a carboxyl functional group, as well as a side-chain (i.e., group of atoms) that is specific to the amino acid. Protein folding refers to a physical process by which a sequence of amino acids folds into a three-dimensional configuration. As used herein the structure of a protein defines the three-dimensional configuration of the atoms in the amino acid sequence of the protein after the protein undergoes protein folding. When in a sequence linked by peptide bonds the amino acids may be referred to as amino acid residues.

Predictions can be made using machine learning models. Machine learning models receive an input and generate an output, e.g., a predicted output, based on the received input. Some machine learning models are parametric models and generate the output based on the received input and on values of the parameters of the model. The structure of a protein may be determined by predicting the structure from its amino acid sequence.

Some machine learning models are deep models that employ multiple layers of models to generate an output for a received input. For example, a deep neural network is a deep machine learning model that includes an output layer and one or more hidden layers that each apply a non-linear transformation to a received input to generate an output.

SUMMARY

This specification describes systems implemented as computer programs on one or more computers in one or more locations that perform protein tertiary structure prediction and protein domain segmentation. A number of techniques are described; these may be combined or used in isolation.

In a first aspect there is described a method performed by one or more data processing apparatus for determining a final predicted structure of a given protein. The given protein includes a sequence of amino acids and a predicted structure of the given protein is defined by values of a plurality of structure parameters. Generating a predicted structure of the given protein may comprise obtaining initial values of the plurality of structure parameters defining the predicted structure and updating the initial values of the plurality of structure parameters. The updating may comprise, at each of a plurality of update iterations: determining a score e.g. a quality score characterizing a quality of the predicted structure defined by current values of the structure parameters. The quality score may represent how close the predicted structure is to being correct and/or how likely is the predicted structure e.g. it may characterize an estimated similarity between the predicted structure and an actual structure of the protein and/or a likelihood of the predicted structure. The quality score may be based on respective outputs of one or more scoring neural networks which are each configured to process: (i) the current values of the structure parameters, or (ii) a representation of the sequence of amino acids of the given protein, or (iii) both.

The method may further comprise, for one or more of the plurality of structure parameters: determining a gradient of the quality score with respect to the current value of the structure parameter, and updating the current value of the structure parameter using the gradient of the quality score with respect to the current value of the structure parameter. Thus some implementations of the method may use a score-based optimization system for structure prediction.

The method may further comprise determining the predicted structure of the given protein to be defined by the current values of the plurality of structure parameters after a final update iteration of the plurality of update iterations.

The method may comprise generating a plurality of predicted structures of the given protein using the above method. The method may then further comprise selecting a particular predicted structure of the given protein as the final predicted structure of the given protein.

The structure parameters are parameters which define the structure of the protein; they may comprise a set of backbone torsion angles (dihedral angles ($\phi$, $\psi$)) and/or may include (3D) atomic coordinates for some or all of the atoms of the protein e.g. carbon atoms, e.g. alpha or beta carbon atoms.

In implementations such an approach facilitates highly accurate predictions of the structure of the given protein by optimizing the quality score, in implementations by gradient descent. The quality score may be viewed as a "potential" to be minimized by gradient descent.

In some implementations the one or more scoring neural networks comprise a distance prediction neural network configured to process the representation of the sequence of amino acids to generate a distance map for the given protein. In implementations the distance map defines, for each of a plurality of pairs of amino acids in the sequence, a respective probability distribution over possible distance ranges between the pair of amino acids. For example the possible distance ranges may be quantized, or the probability distribution over possible distance ranges may be represented by a parameterized probability distribution. A range between the pair of amino acids may be defined by a distance between particular, corresponding atoms of the amino acids (residues) such as alpha and/or beta carbon atoms.

The method may then further comprise determining the quality score by, for each pair of amino acids, determining a probability that the amino acids are separated by a distance defined by the current values of the structure parameters using the corresponding probability distribution over possible distance ranges between the pair of amino acids defined by the distance map.

In implementations predicting a distance facilitates converging to an accurate predicted structure. The distance map jointly predicts many distances and facilitates the method propagating distance information respecting covariation, local structure, and amino acid residue identities to nearby residues. More specifically predicting a distance probability distribution further facilitates this by also modelling uncertainty in the predictions.

In some implementations the quality score is dependent upon a product, over each pair of amino acids in the sequence, of the probability that the amino acids are separated by the distance defined by the current values of the structure parameters, according to the corresponding probability distribution over possible distance ranges defined by the distance map (i.e. the quality score may dependent upon the product of these probabilities).

Determining the quality score may further comprise, for each pair of amino acids, determining a probability that the amino acids are separated by a distance defined by the current values of the structure parameters using a corresponding probability distribution over possible distance ranges between the pair of amino acids defined by a reference distance map. The reference distance map may define a probability distribution based on positions in the sequence of amino acids of the given protein of the amino acids in the amino acid pair, a relative offset of the amino acids in the amino acid pair, or both; but in implementations without being conditioned on the sequence of amino acids, though optionally conditioned on the length of the sequence. The method may further comprise determining the quality score based on a product, over each pair of amino acids in the sequence of amino acids in the given protein, of the probability that the amino acids are separated by the distance defined by the current values of the structure parameters according to the corresponding probability distribution over possible distance ranges defined by the reference distance map. For example the quality score may be corrected for over-representation of the prior distance distribution using this product, e.g. by subtracting a log of this product (or equivalently a sum of the logs of the probabilities) from a log of the quality score.

In implementations the scoring neural network(s) may comprise a structure prediction neural network to process the (representation of the) sequence of amino acids and to generate, for each of the plurality of structure parameters, a probability distribution over possible values for the structure parameter. Then determining the quality score may comprise, for each of the plurality of structure parameters, determining a probability of the current value of the structure parameter using the corresponding probability distribution. Such a quality score may represent a likelihood of the current values of the structure parameters; again modelling this using probability distributions can help accuracy by modelling the uncertainty of the structural predictions.

In some implementations the structure parameters are defined by discrete ranges, in which case it can be advantageous to represent the probability distribution over possible values for a structure parameter as a parametric probability distribution, to provide a smooth, differentiable distribution. This facilitates determining the gradient of the quality score with respect to the structure parameter values. The parametric probability distribution may be a von Mises (or circular normal) probability distribution, which is convenient where the structure parameters may comprise a set of backbone torsion angles.

A quality score determined in this way may be combined with a quality score derived from a distance map, e.g. by summing the (negative) log likelihoods, so that the quality score represents a combined, differentiable "potential" which may be minimized e.g. by gradient descent. The output of the structure prediction neural network and that of the distance prediction neural network may comprise separate heads on a common neural network. Optionally an input to one or both of the structure prediction neural network and the distance prediction neural network may include one or more features derived from the sequence's MSA (multiple sequence alignment).

In implementations the scoring neural network(s) may comprise a geometry neural network to process the (representation of the) sequence of amino acids and to generate a geometry score representing an estimate of a similarity measure between the predicted structure defined by the current values of the structure parameters and an actual structure of the given protein. The quality score may then be based, in whole or in part, on the geometry score.

Determining the quality score may further comprise determining, based on the current values of the structure parameters, a physics or physical constraint score characterizing a likelihood of the current values of the structure parameters dependent upon how closely the current values of the structure parameters conform to biochemical or physical constraints on a structure of the given protein. For example steric constraints on the structure may be modelled by a van der Waals term.

Prior to optimization, e.g. by gradient descent, initial values of the structure parameters may be obtained by processing the sequence of amino acids using the structure prediction neural network and sampling from the probability distribution for each structure parameter. If a structure of the given protein predicted structure has been predicted previously initial values of the structure parameters may be obtained by perturbing these e.g. by random noise values.

In another aspect there is described a computer-implemented method for generating a distance map for a given protein. A (3D) structure of the given protein is defined by a sequence of amino acids, more specifically amino acid residues, arranged in the structure, and the distance map characterizes estimated distances between the amino acid residues in the structure.

The method may comprise generating a plurality of distance map crops, each characterizing estimated distances between (i) amino acid residues in each of one or more respective first positions in the sequence and (ii) amino acid residues in each of one or more respective second positions in the sequence in the structure of the protein. Generating a distance map crop may comprise identifying one or more first positions in the sequence and one or more second positions in the sequence; the first positions may be a proper subset of the sequence. Generating the distance map crop may further comprise determining a network input from the amino acid residues in the first positions in the sequence and the amino acid residues in the second positions in the sequence. Generating the distance map crop may further comprise providing the network input to a distance prediction neural network, configured to process the network input in accordance with current values of distance prediction neural network weights to generate a network output comprising the distance map crop. The distance map for the given protein may then be generated using the plurality of distance map crops.

In implementations using crops can substantially reduce memory and processing requirements. This can also facilitate use of a more complex architecture for the distance prediction neural network, which in turn allows more accurate representations and optionally the prediction of auxiliary features (and optionally training using these features), as described later. In addition the use of crops facilitates distributed processing in which workers generate the distance map crops, and during training facilitates batching of examples.

In some implementations the distance map/crop defines the distance between a pair of amino acid residues using a binary-valued distance estimate (e.g. defining contact/no contact); in other implementations the distance map/crop defines a continuous-valued distance estimate; in other implementations the distance map/crop defines the distance between a pair of amino acid residues using a distance range probability distribution i.e. a probability distribution over possible distance ranges between the pair of amino acids. In the latter case, as previously described the possible distance ranges may be quantized, or the probability distribution over possible distance ranges may be represented by a parameterized probability distribution. A distance or distance range between the pair of amino acids may, for example, be defined by a distance between particular, corresponding atoms of the amino acid residues, such as alpha and/or beta carbon atoms.

In implementations the distance map crops generate overlapping predictions. They may be combined by averaging, which can improve accuracy in the overlap regions, and/or they may be combined with a subsequent, fusing neural network. An output of the fusing neural network may have a receptive field which includes the complete region covered by the distance map crops, and may be configured to process inputs with different offsets.

In some implementations identifying the one or more first positions in the sequence and one or more second positions in the sequence may comprises stochastically sampling the first positions as a first sequence of consecutive positions of a first predetermined length, and/or stochastically sampling the second positions as a second sequence of consecutive positions of a second predetermined length. Thus the crops may correspond to groups of consecutive residues, modelling distances between (long-range) regions of the structure.

In some implementations the distance prediction neural network comprises one or more dilated convolutional neural network layers, one or more residual blocks, and optionally one or more attention layers. This facilitates use of a deep neural network with a large receptive field, and hence improved predictions.

Determining the network input may include extracting components of (i) a representation of the sequence of amino acid residues, and (ii) alignment features derived from a multiple sequence alignment (MSA) which includes the sequence of amino acid residues. The alignment features may include covariation features (amongst the sequences in the MSA), which can help to identify residues in contact.

The distance prediction neural network may have an auxiliary output characterizing a secondary structure of the amino acid residues in the first and second positions in the sequence, and/or characterizing torsion angles of the residues. Training on such auxiliary outputs can help increase the accuracy of the distance map crops, and the outputs may be useful in their own right.

The distance map may be used for determining a predicted structure of the given protein. For example this may involve obtaining initial values for structure parameters defining the protein structure and updating these based on a quality score for the structure defined by the distance map. The updating may comprise, for one or more or each of the structure parameters: optimizing the quality score by adjusting a current value of the structure parameter e.g. by determining a gradient of the quality score with respect to the current value of the structure parameter and then updating the current value of the structure parameter using the gradient of the quality score; or by another optimization process. The predicted structure of the given protein may be defined by the values of the structure parameters after a final update iteration. Optional further components of the quality score may be determined as previous described.

In another aspect there is described a method comprising obtaining data defining: (i) a sequence of amino acids in a given protein, and (ii) a predicted structure of the given protein, wherein the predicted structure of the given protein is defined by values of a plurality of structure parameters; determining a network input from the sequence of amino acid residues in the given protein; processing the network input using a distance prediction neural network in accordance with current values of distance prediction neural network weights to generate a distance map for the given protein, wherein the distance map defines, for each of a plurality of pairs of amino acid residues in the sequence of amino acid residues in the given protein, a respective probability distribution over possible distance ranges between the pair of amino acid residues in a structure of the given protein; and determining a score characterizing a quality of the predicted structure of the given protein using the probability distributions defined by the distance map.

As previously described, using a probability distribution over possible distance ranges can significantly improve the accuracy with which the score characterizes the quality of the predicted structure, and hence an accuracy of a protein structure determined using the score.

The score may be used for determining a predicted structure of the given protein. For example this may involve obtaining initial values of the structure parameters defining the predicted structure and updating these based on the score. The updating may comprise, for one or more or each of the plurality of structure parameters: optimizing the score by adjusting a current value of the structure parameter e.g. by determining a gradient of the score with respect to the current value of the structure parameter and updating the current value of the structure parameter using the gradient; or by another optimization process. The predicted structure of the given protein may be defined by the values of the plurality of structure parameters after a final update iteration. Optional further components of the score may be determined as previous described.

In general other features of the method may be as previously described. For example the network input may be determined from (i) a representation of the sequence of amino acid residues; and (ii) alignment features derived from a multiple sequence alignment which includes the sequence of amino acid residues, e.g. data defining sequences of amino acid residues of one or more proteins in the multiple sequence alignment that are different than the given protein. The alignment features comprise second order statistics of the multiple sequence alignment e.g. a correlation or covariance between residue pairs.

In another aspect there is described a computer-implemented method comprising, at each of one or more iterations maintaining data including: (i) a current predicted structure of a given protein defined by current values of a plurality of structure parameters, and (ii) a quality score characterizing a quality of the current predicted structure based on, i.e. dependent upon, a current geometry score that is an estimate of a similarity measure between the current predicted structure and an actual structure of the given protein. The method may further comprise, at one or more iterations, determining an alternative predicted structure of the given protein based on the current predicted structure, wherein the alternative predicted structure is defined by alternative values of the structure parameters. The method may further comprise, at one or more iterations, processing, using a geometry neural network and in accordance with current values of geometry neural network weights, a network input comprising: (i) a representation of a sequence of amino acid residues in the given protein, and (ii) the alternative values of the structure parameters, to generate an output characterizing an alternative geometry score that is an estimate of a similarity measure between the alternative predicted structure and the actual structure of the given protein. The method may further comprise, at one or more iterations, determining a quality score characterizing a quality of the alternative predicted structure based on the alternative geometry score. The method may further comprise, at one or more iterations, determining whether to update the current predicted structure to the alternative predicted structure using the quality score characterizing the quality of the current predicted structure and the quality score characterizing the quality of the alternative predicted structure.

Some examples of the method are adapted to be implemented by a structure prediction system that uses one or more search computing units. For example the process of determining the alternative predicted structure(s), using the geometry neural network, determining the quality score, and determining whether to update, may be implemented on each of a plurality of search computing units. The maintained data may be local and/or shared, e.g. each search computing unit may store predicted folding structures with high quality scores in shared memory. The search computing units may thus implement a structure optimization system based on simulated annealing using the quality scores.

In some implementations the method obtains a structure fragment defined by (corresponding to) values of a subset of the structure parameters and generates the alternative predicted structure using a portion of the current predicted structure and the structure fragment. The structure fragment may be obtained using a generative neural network and/or from an actual folding structure of a different protein and/or by fragmenting the predicted folding structure from the previous iteration. Using a generative neural network is advantageous as it can generate many, diverse structure fragments, which helps to explore the search space and thus can more quickly result in more accurate structures.

The similarity measure that the geometry score estimates may be any measure of similarity between protein structures such as the Global Distance Test (GDT) measure (based on alpha carbon atoms) or the root mean square deviation (RMSD) metric (a measure of the similarity between the current values and the alternative values of the structure parameters), or some other metric.

The quality score may be dependent upon a combination, e.g. a weighted combination, of the geometry score and a value score estimating a quality of the predicted structure at a future iteration. The value score may be derived from a value neural network configured to process the representation of the sequence of amino acids of the given protein and the current values of the structure parameters. This can help the method trade a short term geometry score deficit for a longer term overall benefit.

In general other features of the method, and optional further components of the quality score, may include those previously described.

The method may be used for determining a predicted structure of the given protein. For example this may involve obtaining initial values of the structure parameters defining the predicted structure and updating these based on the quality score. For example the updating may comprise, at each of a plurality of update iterations, updating the current values of the structure parameters in response to determining whether to update the current predicted structure to the alternative predicted structure. The predicted structure of the given protein may be defined by the values of the structure parameters after a final update iteration.

In another aspect there is described a computer-implemented method comprising receiving data defining a sequence of amino acid residues of a protein and a predicted structure of the protein defined by values of a plurality of structure parameters, and processing this using a geometry neural network and in accordance with current values of geometry neural network weights, to generate an output characterizing a geometry score, where the geometry score is an estimate of a similarity measure between the predicted structure of the protein and an actual structure of the protein. Other features of the method may include those previously described. For example an input to the geometry neural network may include MSA-derived alignment features.

The method may be used for determining a predicted structure of a given protein including the sequence of amino acid residues. For example this may involve obtaining initial values of the structure parameters defining the predicted structure and updating these based on the geometry score. The updating may comprise, for one or more or each of the plurality of structure parameters: optimizing the geometry score by adjusting a current value of the structure parameter e.g. by determining a gradient of the geometry score with respect to the current value of the structure parameter and updating the current value of the structure parameter using the gradient; or by another optimization process. The predicted structure of the given protein may be defined by the values of the plurality of structure parameters after a final update. Optional further components of the score may be determined as previous described.

In another aspect there is described a computer-implemented method comprising receiving data defining: (i) a sequence of amino acid residues of a protein, (ii) a first predicted structure of the protein defined by first values of a plurality of structure parameters, and (iii) a second predicted structure of the protein defined by second values of the plurality of structure parameters. The method may further comprise processing the received data using a geometry neural network and in accordance with current values of geometry neural network weights, to generate an output characterizing a relative geometry score. The relative geometry score defines a prediction for whether a similarity measure between the first predicted structure of the protein and an actual structure of the protein exceeds a similarity measure between the second predicted structure of the protein and the actual structure of the protein. Other features of the method may include those previously described, e.g. an input to the geometry neural network may include MSA-derived alignment features.

The method may be used for determining a predicted structure of a given protein including the sequence of amino acid residues. For example this may involve obtaining initial values of the structure parameters defining the predicted structure and updating these. The updating may comprise, at each of a plurality of update iterations: determining, based on the current predicted structure, an alternative predicted structure of the given protein defined by alternative values of the structure parameters; determining the relative geometry score for the current and alternative values of the structure parameters; using the relative geometry score to determine whether to update the current predicted structure to the alternative predicted structure; and determining the predicted structure of the given protein as that defined by the values of the structure parameters after a final update iteration. Optionally the relative geometry score may be combined with other score components, as previously described.

According to another aspect there is provided a system including a central memory configured to store data defining a set of predicted structures of a given protein, where each structure is defined by respective values of a set of structure parameters. The system further includes one or more search computing units, where each of the one or more search computing units: (i) maintains data defining a respective current predicted structure of the given protein, and (ii) includes a respective local memory configured to store a set of structure fragments. Each structure fragment is defined by respective values of a respective subset of the plurality of structure parameters. Each of the one or more search computing units is configured to perform operations including, at each of one or more search iterations: updating the respective current predicted structure defined by the data maintained by the search computing unit using a structure fragment stored in the respective local memory of the search computing unit; determining whether a central memory update condition is satisfied; if the central memory update condition is satisfied, storing the respective current predicted structure in the central memory; determining whether a local memory update condition is satisfied; if the local memory update condition is satisfied, updating the respective local memory of the search computing unit, including: (i) selecting a predicted structure stored in the central memory, (ii) determining one or more structure fragments from the selected predicted structure, and (iii) storing the determined structure fragments in the respective local memory of the search computing unit.

In some implementations, each structure fragment is defined by respective values of a respective subset of the set of structure parameters defining a structure of a consecutive sequence of amino acid residues in the given protein.

In some implementations, updating the respective current predicted structure defined by the data maintained by the search computing unit using a structure fragment stored in the respective local memory of the search computing unit includes updating the respective current predicted structure to include: (i) a portion of the current predicted structure, and (ii) the structure fragment.

In some implementations, determining whether the central memory update condition is satisfied includes determining a current quality score characterizing a quality of the current predicted structure. The central memory update condition is determined to be satisfied if the current quality score is higher than any quality scores previously determined by the search computing for previous predicted structures of the given protein.

In some implementations, determining whether the local memory update condition is satisfied includes: determining whether a predetermined number of search iterations have been performed by the search computing unit; and determining the local memory update condition is satisfied if the predetermined number of search iterations have been performed by the search computing unit.

In some implementations, selecting a predicted structure stored in the central memory includes selecting a predicted structure stored in the central memory based on a full-atom quality score characterizing a quality of the current predicted structure based on each atom included in the given protein. Each search computing unit is configured to update the respective current predicted structure defined by the data maintained by the search computing unit based on a backbone-atom quality score characterizing a quality of the current predicted structure based on backbone atoms included in the given protein.

In some implementations, determining one or more structure fragments from the selected predicted structure includes determining a partition of the selected predicted structure into a set of structure fragments, where each structure fragment defines a structure of a consecutive sequence of amino acid residues in the given protein.

In some implementations, the system further updates the respective local memory of the search computing unit by one or more structure fragments defined by a network output generated by a generative neural network.

In some implementations, the system further includes a subsystem configured to perform operations including selecting a predicted structure stored in the central memory as a final predicted structure based on full-atom quality scores of each predicted structure stored in the central memory, where the full-atom quality score of a predicted structure is based on each atom included in the given protein.

In some implementations, the set of structure parameters include a set of backbone atom torsion angles.

In some implementations, the set of structure parameters include a set of backbone atom coordinates.

According to another aspect, there is provided a method including, at each of one or more iterations, maintaining data including: (i) a current predicted structure of a given protein defined by current values of a plurality of structure parameters, and (ii) a quality score characterizing a quality the current predicted structure. A set of alternative predicted structures of the given protein is determined, where each alternative predicted structure is defined by respective alternative values of the set of structure parameters, including processing, using a generative neural network and in accordance with current values of generative neural network weights, a network input including a representation of a sequence of amino acid residues in the given protein to generate network outputs defining a set of structure fragments. Each structure fragment is defined by respective values of a respective subset of the set of structure parameters. For each structure fragment, a respective alternative predicted structure is generated that includes (i) a portion of the current predicted structure and (ii) the structure fragment. A respective quality score characterizing a quality of each alternative predicted structure is determined. The method includes determining, based on the quality score characterizing the current predicted structure and the quality scores characterizing the alternative predicted structures, whether to update the current predicted structure to any of the alternative predicted structures.

In some implementations, a quality score characterizing a quality of a predicted structure is based on a likelihood of the predicted structure according to a distance map. The distance map characterizes estimated distances between amino acid residues in an actual structure of the given protein.

In some implementations, a quality score characterizing a quality of a predicted structure is based on an estimate of a similarity measure between the predicted structure and an actual structure of the given protein.

In some implementations, a quality score characterizing a quality of a given predicted structure is based on an estimate of a quality score characterizing a quality of a future predicted structure at a future iteration if the current predicted structure is the given predicted structure.

In some implementations, the network input includes alignment features derived from a multiple sequence alignment, wherein the multiple sequence alignment includes the sequence of amino acid residues in the given protein.

In some implementations, the alignment features are represented as two-dimensional data, and processing the network input using the generative neural network includes: processing the alignment features by one or more convolutional neural network layers; and processing the output of the convolutional layers using a pooling layer.

In some implementations, using a generative neural network to process a network input including a representation of a sequence of amino acid residues in the given protein to generate network outputs defining a set of structure fragments includes processing the network input to generate, for each of multiple structure parameters of the plurality of structure parameters, data defining a respective probability distribution over possible values of the structure parameter. A respective value of each of the multiple structure parameters is determined by sampling the respective value of the structure parameter from the corresponding probability distribution over possible values of the structure parameter.

In some implementations, processing the network input to generate data defining a respective probability distribution over possible values of a particular structure parameter includes processing the representation of the sequence of amino acid residues in the given protein and data defining respective values determined for one or more previous structure parameters which are each previous to the particular structure parameter in an ordering of the structure parameters to generate the data defining the respective probability distribution over possible values of the particular structure parameter.

In some implementations, an architecture of the generative neural network is derived from an architecture of a WaveNet neural network.

In some implementations, processing the network input to generate, for each of multiple structure parameters of the plurality of structure parameters, data defining a respective probability distribution over possible values of the structure parameter includes sampling one or more latent variables from a latent variable space in accordance with a prior probability distribution over the one or more latent variables. The representation of the sequence of amino acid residues in the given protein and the one or more sampled latent variables are processed to generate, for each of multiple structure parameters of the plurality of structure parameters, data defining a respective probability distribution over possible values of the structure parameter.

In some implementations, an architecture of the generative neural network is derived from an architecture of a variational autoencoder.

In some implementations, the architecture of the generative neural network is derived from an architecture of a DRAW neural network.

In some implementations, the generative neural network is trained on a set of training data including a set of actual protein structures.

In some implementations, each structure fragment is defined by respective values of a respective subset of the set of structure parameters defining a structure of a consecutive sequence of amino acid residues in the given protein.

In some implementations, determining whether to update the current predicted structure to any of the alternative predicted structures includes updating the current predicted structure to a given alternative predicted structure if the given alternative predicted structure has a highest quality score.

In another aspect, there is provided a method including receiving data defining a sequence of amino acid residues of a protein. An input including the data defining the sequence of amino acid residues of the protein is processed using a generative neural network to generate, for each of a set of structure parameters characterizing a structure of the sequence of amino acid residues of the protein, data defining a respective probability distribution over possible values of the structure parameter. A predicted structure of the sequence of amino acid residues of the protein is determined, where: the predicted structure is defined by predicted values of the plurality of structure parameter; and the determining includes, for each of the plurality of structure parameters, sampling the predicted value of the structure parameter in accordance with the corresponding probability distribution over possible values of the structure parameter.

In some implementations, for each structure parameter, the data defining the respective probability distribution over possible values of the structure parameter includes respective values of parameters of a mixture of von Mises probability distributions.

According to another aspect, there is provided a method including, at each of one or more iterations, maintaining data including: (i) a current predicted structure of a given protein defined by current values of a plurality of structure parameters, and (ii) a quality score characterizing a quality of the current predicted structure based on a current value score that is an estimate of a quality score characterizing a quality of a future predicted structure at a future iteration given the current predicted structure. An alternative predicted structure of the given protein is determined based on the current predicted structure, where the alternative predicted structure is defined by alternative values of the structure parameters. The method includes processing, using a value neural network and in accordance with current value neural network weights, a network input including: (i) a representation of a sequence of amino acid residues in the given protein, and (ii) the alternative values of the structure parameters, to generate an output characterizing an alternative value score that is an estimate of a quality score characterizing a quality of the future predicted structure at the future time step if, at the current time step, the current predicted structure is updated to the alternative predicted structure. A quality score characterizing a quality of the alternative predicted structure is determined based on the alternative value score. The method includes determining whether to update the current predicted structure to the alternative predicted structure using the quality score characterizing the quality of the current predicted structure and the quality score characterizing the quality of the alternative predicted structure.

In some implementations, the value neural network includes one or more two-dimensional residual convolutional blocks, one or more attention layers, or both.

In some implementations, the network input includes a distance map characterizing estimated distances between pairs of amino acids in an actual structure of the given protein.

In some implementations, the output of the value neural network includes a probability distribution over a predetermined set of possible value scores.

In some implementations, the value neural network is trained, using machine learning training techniques, on a set of training examples. Each training example includes: (i) a training predicted structure of a protein, and (ii) a target value score that is a quality score characterizing a quality of a future predicted structure of the protein that is determined by repeatedly updating the training predicted structure of the protein.

In some implementations, repeatedly updating the training predicted structure of the protein includes repeatedly updating the training predicted structure of the protein using quality scores based on value scores generated by the value neural network in accordance with current values of value neural network weights.

In some implementations, the value neural network is trained using a contrastive divergence training procedure.

According to another aspect there is provided a method including receiving data defining: (i) a sequence of amino acid residues of a protein, and (ii) a particular predicted structure of the protein defined by values of a plurality of structure parameters. An input including the data defining the sequence of amino acid residues of the protein and the data defining the particular predicted structure of the protein is processed using a value neural network and in accordance with current values of value neural network weights to generate an output characterizing a value score. The value score is an estimate of a quality score characterizing a quality of a future predicted structure of the protein, where the future predicted structure of the protein is determined by iteratively modifying the particular predicted structure of the protein over one or more time steps using a structure modification procedure.

In some implementations, the value neural network includes one or more two-dimensional residual convolutional blocks, one or more attention layers, or both.

In some implementations, the input processed by the value neural network includes alignment features derived from a multiple sequence alignment, where the multiple sequence alignment includes the sequence of amino acid residues of the protein.

In some implementations, the alignment features include second order statistics of the multiple sequence alignment.

In some implementations, the input processed by the value neural network includes a distance map characterizing estimated distances between pairs of amino acids in an actual structure of the protein.

In some implementations, the output of the value neural network includes data defining a probability distribution over a predetermined set of possible value scores.

In some implementations, the structure modification procedure includes, at each of multiple iterations, modifying a current predicted structure of the protein by replacing a portion of the current predicted structure of the protein by a structure fragment, where the structure fragment is defined by values of a subset of the plurality of structure parameters.

According to another aspect, there is provided a method including receiving data defining (i) a sequence of amino acid residues of a protein, (ii) a first predicted structure of the protein defined by first values of a set of structure parameters, and (iii) a second predicted structure of the protein defined by second values of the set of structure parameters. The method includes processing an input including: (i) the data defining the sequence of amino acid residues of the protein, (ii) the data defining the first predicted structure of the protein, and (iii) the data defining the second predicted structure of the protein, using a value neural network and in accordance with current values of value neural network weights, to generate an output characterizing a relative value score. The relative value score defines a prediction for whether a quality score characterizing a quality of a first future predicted structure of the protein exceeds a quality score characterizing a quality of a second future predicted structure of the protein. The first future predicted structure of the protein is determined by iteratively modifying the first predicted structure of the protein over one or more iterations using a structure modification procedure. The second future predicted structure of the protein is determined by iteratively modifying the second predicted structure of the protein over one or more iterations using the structure modification procedure.

According to another aspect there is provided a method for determining a domain segmentation of a protein, where the domain segmentation defines a partition of an amino acid sequence of the protein into a plurality of domains. Each domain defines an amino acid subsequence of the amino acid sequence of the protein. The method includes obtaining a set of candidate domain segmentations of the protein, where each candidate domain segmentation defines a set of respective candidate domains. A respective domain segmentation score is determined for each of the candidate domain segmentations, including, for each candidate domain segmentation, determining a respective domain score for each candidate domain defined by the candidate domain segmentation, including, for each candidate domain: obtaining data characterizing estimated distances, in a structure of the protein, between each pair of amino acids in the amino acid subsequence defined by the candidate domain; and determining the domain score for the candidate domain based on the data characterizing the estimated distances, in the structure of the protein, between each pair of amino acids in the amino acid subsequence defined by the candidate domain; determining the domain segmentation score of the candidate domain segmentation from the respective domain scores for each candidate domain defined by the candidate domain segmentation. The domain segmentation of the protein is determined to be a candidate domain segmentation from the set of candidate domain segmentations based on the respective domain segmentation scores of the candidate domain segmentations.

In some implementations, obtaining data characterizing estimated distances, in a structure of the protein, between each pair of amino acids in the amino acid subsequence defined by the candidate domain includes obtaining data characterizing, for each pair of amino acids in the amino acid subsequence defined by the candidate domain, whether the pair of amino acids are predicted to be separated by a less than a threshold distance in the structure of the protein.

In some implementations, determining the domain score for the candidate domain based on the data characterizing the estimated distances, in the structure of the protein, between each pair of amino acids in the amino acid subsequence defined by the candidate domain includes determining, for each given amino acid in the candidate domain, a number of other amino acids in the candidate domain which are predicted to be separated from the given amino acid by less than the threshold distance. The method includes obtaining data defining a probability distribution which defines, for each of a plurality of non-negative integer values, a respective likelihood that a given amino acid in a training domain of a same length as the target domain is separated by less than the threshold distance from a number of other amino acids in the training domain defined by the integer value. The length of a domain is the length of the amino acid subsequence defined the domain, and a training protein domain is an actual domain of a respective protein. The domain score for the candidate domain is determined based on: (i) for each given amino acid in the candidate domain, the number of other amino acids in the candidate domain which are predicted to be separated from the given amino acid by less than the threshold distance, and (ii) the probability distribution.

In some implementations, obtaining data defining a probability distribution includes obtaining a mean value and a standard deviation value which define a Gaussian probability distribution. The mean value is a mean of a set of non-negative integer values including, for each given amino acid in each given training domain of a plurality of training domains, the number of other amino acids in the given training domain which are separated from the given training domain by less than the threshold distance. The standard deviation value is a standard deviation of the set of non-negative integer values including, for each given amino acid in each given training domain of a plurality of training domains, the number of other amino acids in the given training domain which are separated from the given training domain by less than the threshold distance.

In some implementations, the domain score for a candidate domain is determined based on a product of, for each amino acid in the candidate domain, a likelihood of the number of other amino acids in the candidate domain which are predicted to be separated from the given amino acid by less than the threshold distance according to the probability distribution.

In some implementations, the method further includes determining the domain score for the candidate domain based on a likelihood of a length of the amino acid subsequence defined by the candidate domain, in addition to the data characterizing the estimated distances, in the structure of the protein, between each pair of amino acids in the amino acid subsequence defined by the candidate domain. The length of a domain is the length of the amino acid subsequence defined the domain.

In some implementations, the method further includes determining the domain segmentation score of the candidate domain segmentation based on a likelihood of the number of candidate domains defined by the candidate domain segmentation, in addition to the respective domain scores for each candidate domain defined by the candidate domain segmentation.

In some implementations, the data characterizing the estimated distances, in the structure of the protein, between each pair of amino acids in the amino acid subsequence specified by the candidate domain is obtained from a distance map. The distance map characterizes estimated distances, in the structure of the protein, between each pair of amino acids in the amino acid sequence of the protein. The distance map is a weighted average of distance map crops, where: each distance map crop characterizes estimated distances, in the structure of the protein, between each pair of amino acids in a respective amino acid subsequence of the amino acid sequence of the protein; and each distance map crop is generated by processing a multiple sequence alignment (MSA) for the amino acid subsequence corresponding to the distance map crop.

In some implementations, a weight of each distance map crop in the weighted average of distance map crops is determined based on a number of amino acid sequences included in the MSA which is processed to generate the distance map crop.

In some implementations, the domain segmentation of the amino acid sequence is determined to be the candidate domain segmentation with the highest domain segmentation score.

In implementations a protein structure may be predicted using a combination of one or more of the above described techniques. Thus some implementations of a protein structure prediction system may use one or more neural networks to predict a distance between pairs of residues in the structure and/or to directly estimate the accuracy of a candidate structure, and/or to directly generate protein structures. It is not essential that all these techniques be used together. These approaches may be combined with one or more optimization techniques such as simulated annealing e.g. using multiple computing units or gradient descent, e.g. to optimize a score. Such a score may thus be considered as a potential to be minimized, such as a distance potential or a potential of mean force.

The methods and systems described herein may be used to obtain a ligand such as a drug or a ligand of an industrial enzyme. For example a method of obtaining a ligand may comprise obtaining a target amino acid sequence, in particular the amino acid sequence of a target protein, and performing a computer-implemented method as described above or herein, using the target amino acid sequence as the sequence of amino acids, to determine a (tertiary) structure of the target protein i.e. the or the final predicted structure. The method may then comprise evaluating an interaction of one or more candidate ligands with the structure of the target protein. The method may further comprise selecting one or more of the candidate ligands as the ligand dependent on a result of the evaluating of the interaction.

In some implementations evaluating the interaction may comprise evaluating binding of the candidate ligand with the structure of the target protein. For example evaluating the interaction may comprise identifying a ligand that binds with sufficient affinity for a biological effect. In some other implementations evaluating the interaction may comprise evaluating an association of the candidate ligand with the structure of the target protein which has an effect on a function of the target protein e.g. an enzyme. The evaluating may comprise evaluating an affinity between the candidate ligand and the structure of the target protein, or evaluating a selectivity of the interaction.

The candidate ligand(s) may be derived from a database of candidate ligands, and/or may be derived by modifying ligands in a database of candidate ligands e.g. by modifying a structure or amino acid sequence of a candidate ligand, and/or may be derived by stepwise or iterative assembly/optimization of a candidate ligand.

The evaluation of the interaction of a candidate ligand with the structure of the target protein may be performed using a computer-aided approach in which graphical models of the candidate ligand and target protein structure are displayed for user-manipulation, and/or the evaluation may be performed partially or completely automatically, for example using standard molecular (protein-ligand) docking software. In some implementations the evaluation may comprise determining an interaction score for the candidate ligand, where the interaction score comprises a measure of an interaction between the candidate ligand and the target protein. The interaction score may be dependent upon a strength and/or specificity of the interaction e.g. a score dependent on binding free energy. A candidate ligand may be selected dependent upon its score.

In some implementations the target protein comprises a receptor or enzyme and the ligand is an agonist or antagonist of the receptor or enzyme. In some implementations the method may be used to identify the structure of a cell surface marker. This may then be used to identify a ligand, e.g. an antibody or a label such as a fluorescent label, which binds to the cell surface marker. This may be used to identify and/or treat cancerous cells.

In some implementations the candidate ligand(s) may comprise small molecule ligands, e.g. organic compounds with a molecular weight of <900 daltons. In some other implementations the candidate ligand(s) may comprise polypeptide ligands i.e. defined by an amino acid sequence.

Some implementations of the method may be used to determine the structure of a candidate polypeptide ligand, e.g. a drug or a ligand of an industrial enzyme. The interaction of this with a target protein structure may then be evaluated; the target protein structure may have been determined using a computer-implemented method as described herein or using conventional physical investigation techniques such as x-ray crystallography and/or magnetic resonance techniques.

Thus in another aspect there is provided a method of obtaining a polypeptide ligand (e.g. the molecule or its sequence). The method may comprise obtaining an amino acid sequence of one or more candidate polypeptide ligands. The method may further comprise performing a computer-implemented method as described above or herein, using the amino acid sequence of the candidate polypeptide ligand as the sequence of amino acids, to determine a (tertiary) structure of the candidate polypeptide ligand. The method may further comprise obtaining a target protein structure of a target protein, in silico and/or by physical investigation, and evaluating an interaction between the structure of each of the one or more candidate polypeptide ligands and the target protein structure. The method may further comprise selecting one of the one or more of the candidate polypeptide ligands as the polypeptide ligand dependent on a result of the evaluation.

As before evaluating the interaction may comprise evaluating binding of the candidate polypeptide ligand with the structure of the target protein e.g. identifying a ligand that binds with sufficient affinity for a biological effect, and/or evaluating an association of the candidate polypeptide ligand with the structure of the target protein which has an effect on a function of the target protein e.g. an enzyme, and/or evaluating an affinity between the candidate polypeptide ligand and the structure of the target protein, or evaluating a selectivity of the interaction. In some implementations the polypeptide ligand may be an aptamer.

Implementations of the method may further comprise synthesizing i.e. making the small molecule or polypeptide ligand. The ligand may be synthesized by any conventional chemical techniques and/or may already be available e.g. may be from a compound library or may have been synthesized using combinatorial chemistry.

The method may further comprise testing the ligand for biological activity in vitro and/or in vivo. For example the ligand may be tested for ADME (absorption, distribution, metabolism, excretion) and/or toxicological properties, to screen out unsuitable ligands. The testing may comprise e.g. bringing the candidate small molecule or polypeptide ligand into contact with the target protein and measuring a change in expression or activity of the protein.

In some implementations a candidate (polypeptide) ligand may comprise: an isolated antibody, a fragment of an isolated antibody, a single variable domain antibody, a bi- or multi-specific antibody, a multivalent antibody, a dual variable domain antibody, an immuno-conjugate, a fibronectin molecule, an adnectin, an DARPin, an avimer, an affibody, an anticalin, an affilin, a protein epitope mimetic or combinations thereof. A candidate (polypeptide) ligand may comprise an antibody with a mutated or chemically modified amino acid Fc region, e.g. which prevents or decreases ADCC (antibody-dependent cellular cytotoxicity) activity and/or increases half-life when compared with a wild type Fc region.

Misfolded proteins are associated with a number of diseases. Thus in a further aspect there is provided a method of identifying the presence of a protein mis-folding disease. The method may comprise obtaining an amino acid sequence of a protein and performing a computer-implemented method as described above or herein using the amino acid sequence of the protein to determine a structure of the protein. The method may further comprise obtaining a structure of a version of the protein obtained from a human or animal body e.g. by conventional (physical) methods. The method may then comprise comparing the structure of the protein with the structure of the version obtained from the body and identifying the presence of a protein mis-folding disease dependent upon a result of the comparison. That is, mis-folding of the version of the protein from the body may be determined by comparison with the in silico determined structure.

In some other aspects a computer-implemented method as described above or herein may be used to identify active/binding/blocking sites on a target protein from its amino acid sequence.

Particular embodiments of the subject matter described in this specification can be implemented so as to realize one or more of the following further advantages.

This specification describes a structure prediction system that can determine a final predicted structure of a protein using multiple search computing units running in parallel. Each of the search computing units is configured to determine a respective trajectory of predicted protein structures over a series of search iterations and can save particularly "promising" predicted structures (i.e., predicted structures with high quality scores) to a central memory. To determine an update to a current predicted structure, a search computing unit can perturb the current predicted structure using structure fragments from previous predicted structures stored in the central memory. In this manner, the search computing unit can continuously (i.e., at each search iteration) exploit previously discovered knowledge about the structure of the protein to update the current predicted structure. Moreover, in some implementations, the search computing units can share a single central memory, in which case each search computing unit can exploit knowledge about the structure of the protein discovered by each other search computing unit to update its current predicted structure. In contrast, in some conventional systems, the predicted structure of a protein is only updated using structure fragments obtained from a database of known protein structures (e.g., which are determined experimentally). By updating the predicted structure of a protein using a more diverse set of structure fragments, including structure fragments from previous predicted structures stored in a central memory, the system described in this specification can potentially generate more accurate predicted folding structures, over fewer search iterations, than some conventional systems. By requiring fewer search iterations to generate accurate predicted folding structures, the system described in this specification may thereby consume fewer computational resources (e.g., memory and computing power) than some conventional systems.

This specification describes a structure prediction system that can generate structure fragments using a generative neural network trained on a database of known protein structures. The generative neural network can generate huge numbers of diverse structure fragments, many of which may not correspond to any known (e.g., experimentally determined) protein structures. The search computing units included in the system described in this specification can use the structure fragments generated by the generative neural network to update their respective current predicted structures, thereby potentially generating more accurate predicted folding structures than conventional systems restricted to structure fragments drawn from known protein structures. Moreover, by using structure fragments generated by a generative neural network to update the predicted structure of the protein, the system described in this specification may require fewer search iterations to determine accurate predicted structures of the protein, and may thereby consume fewer computational resources (e.g., memory and computing power) than some conventional systems.

This specification describes a structure prediction system that can determine the quality score of a predicted structure using a geometry score and a value score. The geometry score of a predicted structure is an estimate of a similarity measure between the predicted structure of the protein and the actual structure of the protein. The value score of a given predicted structure is an estimate of a quality score characterizing a quality of a future predicted folding structure generated by a search computing unit at a future search iteration if the current predicted structure is the given predicted structure. By determining quality scores of predicted structures using geometry scores and value scores, the system described in this specification may determine more accurate predicted protein structures than some conventional systems. For example, using value scores can enable a search computing unit to update its current predicted structure in ways that may decrease the quality of the current predicted structure in the short term (e.g., over a few search iterations), but which may result in a higher quality final predicted structure. Moreover, by using geometry scores and value scores in determining quality scores of predicted structures, the system described in this specification may require fewer search iterations to determine accurate predicted protein structures and thereby may consume fewer computational resources (e.g., memory and computing power) than some conventional systems.

This specification describes a structure prediction system that can generate a distance map for a protein (which characterizes estimated distances between amino acid residues in the structure of the protein) by generating multiple "crops" of the distance map using a distance prediction neural network, and subsequently fusing the crops. By generating distance map crops rather than full distance maps, the architecture of the distance prediction neural network is not restricted by the longest amino acid sequence that must be modeled. Therefore, the distance prediction neural network described in this specification can have a more complex architecture (e.g., with more neural network layers) than it otherwise would, thereby enabling more precise distance map estimation.

This specification describes a structure prediction system that can generate distance maps which characterize the distance between pairs of amino acids using continuous-valued distance estimates or distance range probability distributions. In contrast, in some conventional systems, distance maps characterize the distance between pairs of amino acids using binary variables (e.g., indicating whether the distances between pairs of amino acids are less than a predetermined threshold). By generating distance maps which convey more precise information about how closely predicted structures conform with actual protein structures, the system described in this specification can determine more accurate predicted folding structures than some conventional systems.

By generating distance maps which are more accurate and precise than those generated by some conventional systems, the system described in this specification may consume fewer computational resources (e.g., memory and computing power) than some conventional systems. For example, the system described in this specification may use the generated distance maps to determine quality scores which enable current predicted structures to be updated more effectively than in some conventional systems, thereby reducing the number of search iterations required to determine accurate predicted structures.

This specification describes a structure prediction system that can be used to generate predicted protein structures which can accurately approximate the actual structures of different proteins. As will be described in more detail below, accurately predicting protein structures may facilitate understanding life processes (e.g., including the mechanisms of many diseases) and designing proteins (e.g., as drugs, or as enzymes for industrial processes). By predicting protein structures from amino acid sequences, the system described in this specification can facilitate areas of biochemical research and engineering which involve proteins (e.g., drug development) and obviate the need for expensive and time consuming physical experiments to determine protein structures.

This specification describes a structure prediction system that can optimize the current structure parameter values defining a predicted structure of a protein using a "warm" gradient descent optimization procedure. In particular, the warm gradient descent optimization procedure endows the current structure parameter values with a momentum which enables them to "roll around" the quality score surface during optimization rather than directly finding a local minimum of the quality score surface. The quality score surface refers to the high-dimensional surface defined by the mapping from respective structure parameter values to the quality scores of predicted protein structures defined by the respective structure parameter values. By using a warm gradient descent optimization procedure, the system described in this specification can effectively explore the space of possible structure parameter values to determine a diverse set of predicted structures of a protein, each of which approximately correspond to a local minimum of the quality score surface. The best predicted structure in the set of predicted structures can be selected as the final predicted structure of the protein. In this manner, the system described in this specification can determine a final predicted structure of the protein with a higher quality score than if the system used a different gradient descent optimization procedure which produced a less diverse set of predicted structures of the protein.

This specification describes a structure prediction system that can determine a final predicted structure which (approximately) optimizes a quality score that is based on the outputs of one or more scoring neural networks. The scoring neural networks can include, for example, a structure prediction neural network (which generates respective probability distributions over possible values of the structure parameters), a geometry neural network (which generates an estimate of a similarity measure between the predicted structure and the actual structure of the protein), and a distance prediction neural network (which generates distance range probability distributions characterizing inter-amino acid distances). The scoring neural networks can be trained, using machine learning training techniques, on a database of known protein structures (e.g., which are determined using physical experiments). By determining a final predicted structure based on a quality score which is learned directly from known protein structures using machine learning techniques, rather than a quality score that is handcrafted based on heuristic constraints, the system described in this specification can generate more accurate final predicted protein structures.

This specification describes a structure prediction system that can outperform some other structure prediction systems by generating more accurate predicted final protein structures while consuming fewer computational resources (e.g., memory, computing power, or both). For example, some structure prediction systems generate predicted structures by iteratively adjusting a current predicted structure using random protein structure fragments. These structure prediction systems may determine a random protein structure fragment should be inserted into the current predicted structure if doing so would increase the overall quality score of the predicted structure. In contrast to these systems, this specification describes a structure prediction system that can directly optimize the quality score with respect to the predicted structure using gradient descent, and in this manner can generate a more accurate predicted structure over fewer iterations.

This specification describes a domain segmentation system that can generate a domain segmentation of a protein which can be used to accurately and efficiently predict the structure of the protein. For example, a structure prediction system can determine a predicted structure of each domain of the protein (i.e., as defined by the domain segmentation), and subsequently determine a predicted structure of the entire protein by combining the predicted structures of each domain. Determining a predicted structure of a domain of the protein is generally an "easier" problem that determining a predicted structure of the entire protein at once. In particular, since the number of possible structures of an amino acid sequence increases exponentially with the length of the amino acid sequence, the search space of possible predicted structures of a domain will generally be exponentially smaller than the search space of possible predicted structures of the entire protein. By enabling structure prediction systems to separately determine predicted structures of protein domains rather than predicting entire protein structures at once, the system described in this specification enables structure predictions systems to generate more accurate predictions while consuming fewer computational resources (e.g., memory, computing power, or both).

This specification describes a system that can generate a distance map for a protein by combining a large number of distance map crops. The system generates each distance map crop by processing a respective multiple sequence alignment (MSA) corresponding to a respective subsequence of the amino acid sequence of the protein. By generating a distance map for the protein based on distance map crops computed from multiple different MSAs, the system described in this specification can generate a more robust and accurate distance map than by processing a single MSA corresponding to the entire amino acid sequence of the protein.

It can be appreciated that the structure prediction systems described in this specification can be used to predict the structures of protein domains, entire proteins, or protein complexes. In a protein complex, a group of multiple proteins fold together into a global structure (e.g., where the individual proteins may be linked by non-covalent protein-protein interactions).

The details of one or more embodiments of the subject matter of this specification are set forth in the accompanying drawings and the description below. Other features, aspects, and advantages of the subject matter will become apparent from the description, the drawings, and the claims.

BRIEF DESCRIPTION OF THE DRAWINGS

Like reference numbers and designations in the various drawings indicate like elements.

DETAILED DESCRIPTION

Figure 1:
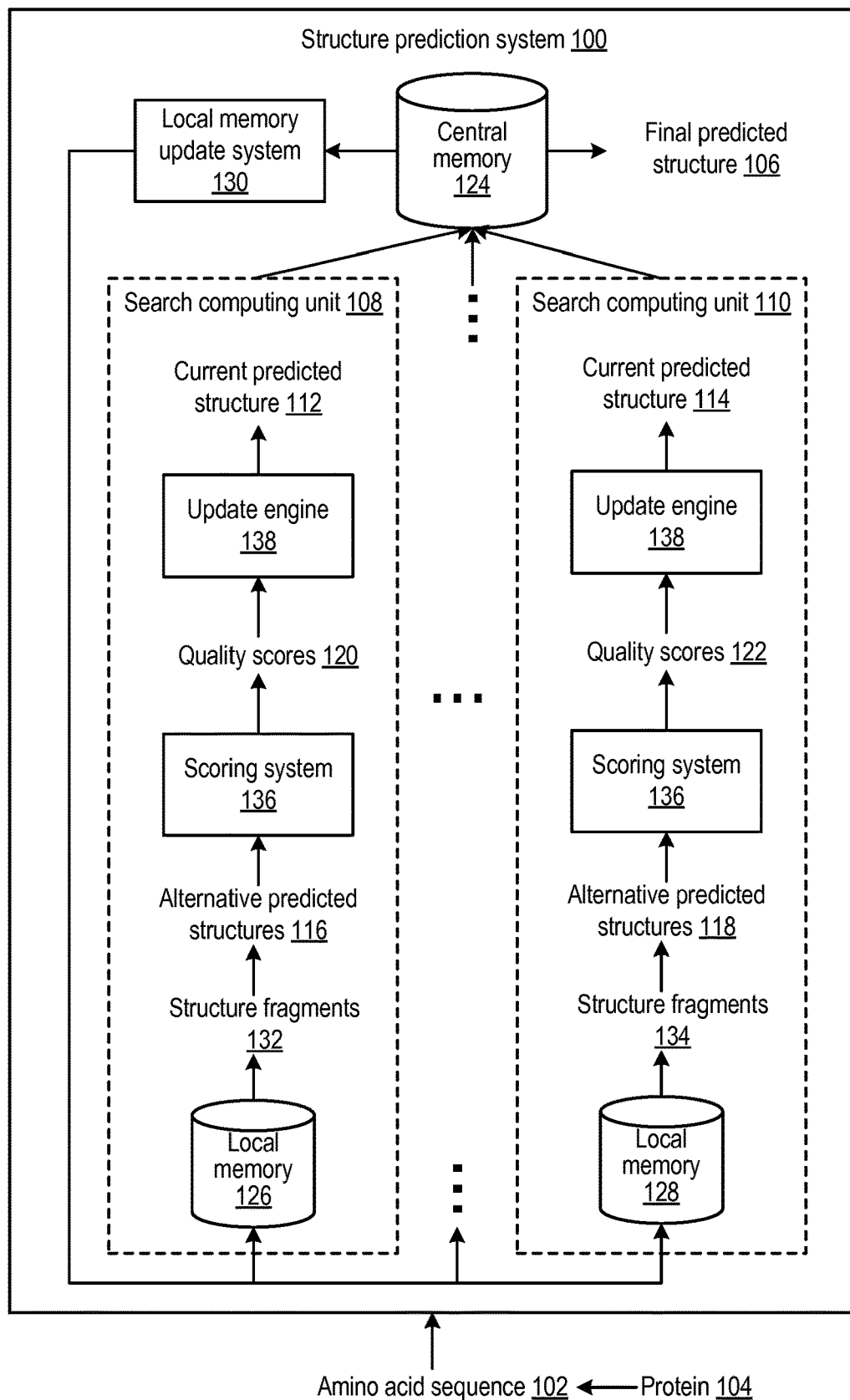
FIG. 1 is a block diagram of an example structure prediction system that uses one or more search computing units.

FIG. 1 shows an example structure prediction system 100. The structure prediction system 100 is an example of a system implemented as computer programs on one or more computers in one or more locations in which the systems, components, and techniques described below are implemented.

Figure 2:
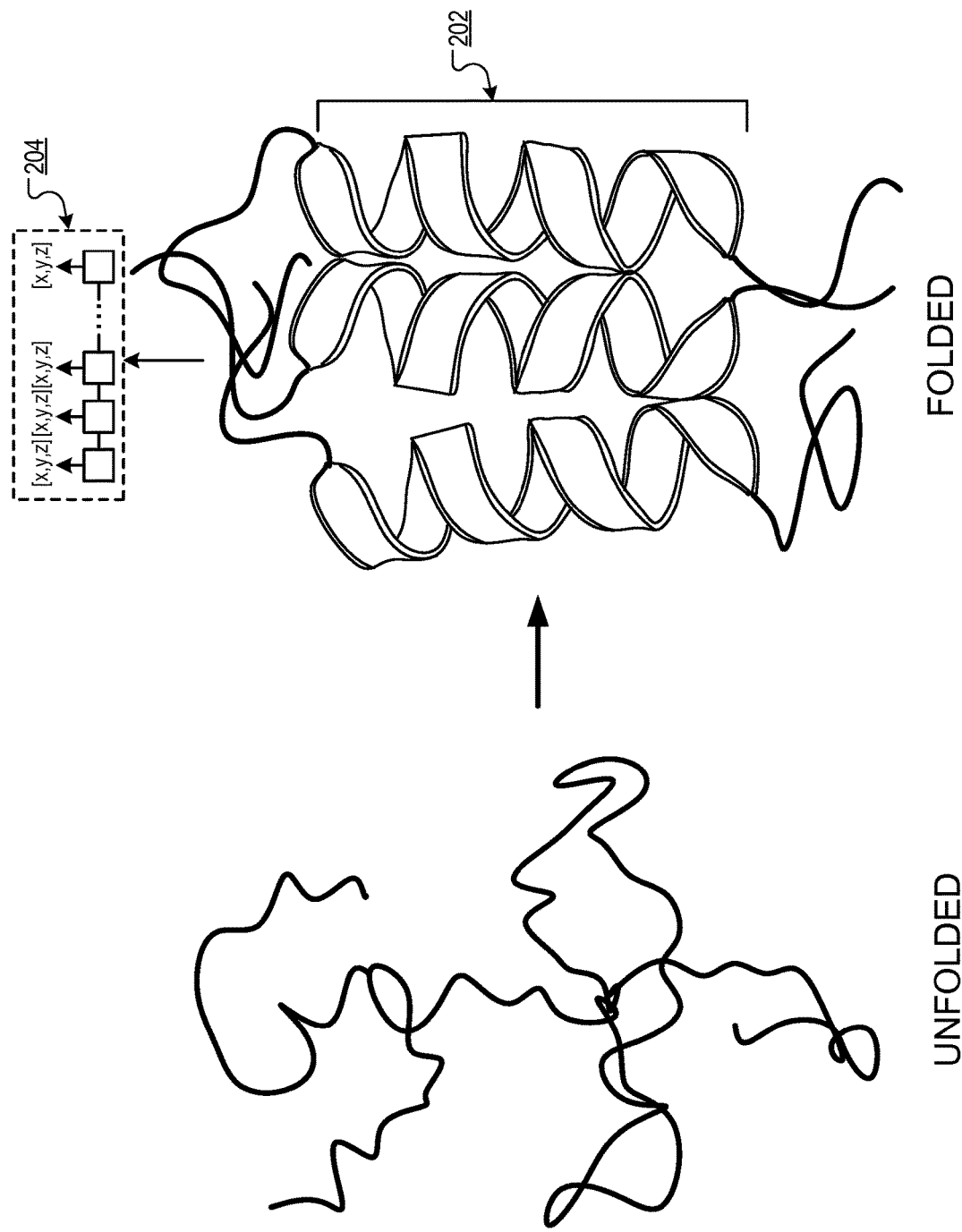
FIG. 2 is an illustration of an unfolded protein and a folded protein.

The structure prediction system 100 is configured to process data defining an amino acid sequence 102 of a protein 104 to generate a final predicted structure 106 of the protein 104. Each amino acid in the amino acid sequence 102 is an organic compound which includes an amino functional group and a carboxyl functional group, as well as a side-chain (i.e., group of atoms) which is specific to the amino acid. The final predicted structure 106 defines an estimate of a three-dimensional configuration of the atoms in the amino acid sequence 102 of the protein 104 after the protein 104 undergoes protein folding. Protein folding refers to a physical process by which a sequence e.g. a random coil of amino acids (e.g., defined by the amino acid sequence 102 of the protein 104) folds into a unique three-dimensional configuration (e.g., as estimated by the final predicted structure 106). Although the configuration is described as unique this does not mean that a protein may not, under some circumstances, fold differently. FIG. 2 provides an illustration of an unfolded protein and a folded protein.

The structure of a protein determines the biological function of the protein. Therefore, determining protein structures may facilitate understanding life processes (e.g., including the mechanisms of many diseases) and designing proteins (e.g., as drugs, or as enzymes for industrial processes). For example, which molecules (e.g., drugs) will bind to a protein (and where the binding will occur) depends on the structure of the protein. Since the effectiveness of drugs can be influenced by the degree to which they bind to proteins (e.g., in the blood), determining the structures of different proteins may be an important aspect of drug development. However, determining protein structures using physical experiments (e.g., by x-ray crystallography) can be time-consuming and very expensive. Therefore, by predicting protein structures from amino acid sequences, the system 100 can facilitate areas of biochemical research and engineering which involve proteins (e.g., drug development).

The amino acid sequence 102 can be represented in any appropriate numerical format. For example, the amino acid sequence 102 may be represented as a sequence of one-hot vectors. In this example, each one-hot vector in the sequence of one-hot vectors represents a corresponding amino acid in the amino acid sequence 102. A one-hot vector has a different component for each different amino acid (e.g., of a predetermined number of amino acids). A one-hot vector representing a particular amino acid has value one (or some other predetermined value) in the component corresponding to the particular amino acid and value zero (or some other predetermined value) in the other components.

A structure of the amino acid sequence 102 (e.g., the final predicted structure 106 output by the system 100) is defined by the values of a set of structure parameters. In some implementations, the structure parameters are a sequence of three-dimensional (3D) numerical coordinates (e.g., represented as 3D vectors) where each coordinate represents the position (in some given frame of reference) of a corresponding atom in an amino acid from the amino acid sequence 102. For example, the structure parameters may be a sequence of 3D numerical coordinates representing the respective positions of the alpha carbon atoms in the amino acids in the structure. An alpha carbon atom, which is referred to in this specification as a backbone atom, refers to a carbon atom in an amino acid to which the amino functional group, the carboxyl functional group, and the side-chain are bonded. In some implementations, the structure parameters are a sequence of torsion (i.e., dihedral) angles between specific atoms in the amino acids in the structure. For example, the structure parameters may be a sequence of phi ($\phi$), psi ($\psi$), and optionally omega ($\omega$) dihedral angles between the backbone atoms in amino acids in the structure, specifically to either side of an alpha carbon (the peptide bond typically constrains $\omega$ to be close to 0 or 180 degrees).

The system 100 includes one or more search computing units (e.g., the search computing units 108 and 110). Each of the search computing units is configured maintain a current predicted structure (e.g., the current predicted structures 112 and 114), and at each of one or more search iterations, to determine whether to update the current predicted structure to an alternative predicted structure (e.g., one of the alternative predicted structures 116 or 118). Generally, each search computing unit is tasked with determining a predicted structure with the highest possible quality score (e.g., the quality score 120 or 122). As will be described in more detail below (e.g., with reference to FIG. 7), each search computing unit can store predicted folding structures with high quality scores in a central memory 124. The search computing units can fragment predicted structures stored in the central memory 124 to determine structure fragments used to update their respective current predicted structures, and the system can determine the final predicted structure 106 of the protein 104 by selecting a predicted structure stored in the central memory 124.

A quality score of a predicted structure generally characterizes a quality of the predicted structure. For example, as will be described in more detail with reference to FIG. 5, the quality score of a predicted structure may characterize an estimated similarity between the predicted structure and an actual structure of the protein 104, a likelihood of the predicted structure based on the distances between the backbone atoms in the amino acids in the predicted structure, or both. Generally, the quality score of a predicted structure may be determined based on a proper subset of the atoms in the amino acids (e.g., solely based on the backbone atoms and not on any other atoms) in the amino acid sequence 102, or based on all of the atoms in each of the amino acids in the amino acid sequence 102. A quality score of a predicted structure which is based solely on the backbone atoms in the amino acids may be referred to as a backbone-atom score, while a quality score determined with reference to all of the atoms in each of the amino acids may be referred to as a full-atom score.

Each search computing unit may be, e.g., a computer, a core within a computer having multiple cores, or other hardware or software, e.g., a dedicated thread, within a computer capable of independently performing operations (e.g., search iterations). The search computing units may include processor cores, processors, microprocessors, special-purpose logic circuitry, e.g., an FPGA (field-programmable gate array) or an ASIC (application-specific integrated circuit), or any other appropriate computing units. In some examples, the search computing units are all the same type of computing unit. In other examples, the search computing units may be different types of computing units. For example, one search computing unit may be a CPU while other search computing units may be GPUs. The search computing units may be configured to operate asynchronously. More specifically, each search computing unit can be configured to perform search iterations independently of each other search computing unit.

Each search computing unit generates a respective trajectory (i.e., a sequence) of predicted structures of the protein 104 (each of which is associated with a different quality score) by iteratively updating a respective current predicted structure. At each search iteration, each search computing unit can determine whether a central memory update condition is satisfied, and in response to determining the central memory update condition is satisfied, can store its current predicted structure in a central memory 124. Storing a predicted structure in the central memory 124 refers to storing the values of the structure parameters defining the predicted structure in the central memory 124. A search computing unit may determine that the central memory update condition is satisfied if, for example, the quality score of its current predicted structure is the highest quality score in the trajectory of predicted structures generated by the search computing unit up to that search iteration. In this example, the central memory 124 is dynamically updated to store the most "promising" predicted structures (e.g., which are most likely to accurately approximate the actual structure of the amino acid sequence 102) generated by the search computing units. The central memory 124 is an (integrated or distributed) data store that can be implemented, for example, as a logical data storage area or a physical data storage device.

Each search computing unit maintains a respective local memory (e.g., the local memory 126 or 128) which is configured to store structure fragments. Each structure fragment characterizes a predicted structure of a subsequence (i.e., fragment) of amino acids in the amino acid sequence 102. Each structure fragment is defined by: (i) data indicating a respective subsequence of the amino acid sequence 102, and (ii) the values of a set of structure parameters characterizing the structure of the amino acids in the respective subsequence of the amino acid sequence 102. In a particular example, if the amino acid sequence 102 is given by: [A, C, E, F, D, G, G, A] (e.g., where A is the symbol for the amino acid alanine, C is the symbol for the amino acid cysteine, etc.), then a structure fragment may characterize a predicted structure of the consecutive subsequence of amino acids [C, E, F] in the amino acid sequence 102. In this example, the structure fragment may defined by: (i) data indicating the subsequence of amino acids [C, E, F], and (ii) the values of structure parameters including torsion angles between the backbone atoms in the amino acids C, E, and F. As will be described in more detail later, the system 100 includes a local memory update system 130 which is configured to initialize and update the respective local memory of each search computing unit.

Each search computing unit determines whether to update its respective current predicted structure to an alternative predicted structure (e.g., the alternative predicted structures 116 or 118) at each of the multiple search iterations performed by the search computing unit (as described earlier). In particular, at each search iteration, each search computing unit obtains one or more respective structure fragments (e.g., the structure fragments 132 or 134) from the local memory maintained by the search computing unit and generates a respective alternative predicted structure from each obtained structure fragment. The search computing unit may obtain the structure fragments from its local memory by randomly sampling a predetermined number of structure fragments from its local memory. The search computing unit can determine each alternative predicted structure to include: (i) a portion of the current predicted structure maintained by the search computing unit, and (ii) an obtained structure fragment. In this manner, the search computing unit generates each alternative predicted structure as a "perturbation" of the current predicted structure maintained by the search computing unit using a respective structure fragment. An example process for determining whether to update a current predicted structure of a protein to an alternative predicted structure of the protein is described further with reference to FIG. 8.

The size of each structure fragment (e.g., the number of amino acids in the subsequence of the amino acid sequence 102 corresponding to the structure fragment) and the number of alternative predicted structures generated by the search computing unit at each iteration are search computing unit hyper-parameters. Generally, such hyper-parameters can differ between search computing units and can change between iterations within a single search computing unit (e.g., according to a fixed schedule or as specified by the output of a hyper-parameter selection neural network).

Each search computing unit determines a respective numerical quality score (e.g., the quality scores 120 or 122) for each respective alternative predicted structure using a scoring system (e.g., the scoring system 136). As described earlier, the quality score for a predicted structure generally characterizes a quality of the structure. An example of a scoring system 136 is described with reference to FIG. 5. As well as the quality scores of the alternative predicted structures, the search computing unit obtains a quality score of the current predicted structure maintained by the search computing unit. For example, the search computing unit may maintain a quality score of the current predicted structure determined using the scoring system 136 at a previous search iteration.

Each search computing unit includes an update engine (e.g., the update engine 138) which determines whether to update its respective current predicted structure to any of the alternative predicted structures using the quality scores of the alternative predicted structures and the quality score of the current predicted structure.

In some implementations, the update engine may determine whether to update the current predicted structure to an alternative predicted structure using a deterministic procedure based on the quality scores. For example, the update engine may determine to update the current predicted structure to a particular alternative predicted structure if the particular alternative predicted structure has a higher quality score than the current predicted structure and any of the other alternative predicted structures. In this example, if the current predicted structure has a higher quality score than any of the alternative predicted structures, the update engine may determine not to update the current predicted structure to any of the alternative predicted structures.

In some implementations, the update engine may determine whether to update the current predicted structure to an alternative predicted structure using a stochastic procedure (i.e., that involves some randomness) based on the quality scores. For example, the update engine may determine a probability distribution over a set of structures including the current predicted structure and each of the alternative predicted structures using the quality scores. In a particular example, the update engine may determine the probability distribution by processing the respective quality scores of the current predicted structure and each of the alternative predicted structures using a soft-max function. The update engine may determine to update the current predicted structure to a structure sampled from the set of structures including the current predicted structure and each of the alternative predicted structures using the probability distribution. By determining whether to update the current predicted structure to an alternative predicted structure using a stochastic procedure, the system 100 can "explore" the space of possible protein structures and thereby potentially determine more accurate predicted structures (as described further with reference to FIG. 8).

The system 100 includes a local memory update system 130 which is configured to initialize and update the local memories of the search computing units. Initializing the local memory of a search computing unit refers to storing multiple structure fragments in the local memory prior to the first search iteration performed by the search computing unit. Updating the local memory of a search computing unit refers to including different structure fragments in the local memory (and potentially removing structure fragments from the local memory) between search iterations performed by the search computing unit. As will be described in more detail with reference to FIG. 3, the local memory update system 130 can, for example, update the local memories of the search computing units using structure fragments obtained from predicted structures stored in the central memory by the search computing units. The local memory update system 130 can thereby enable each search computing unit to take advantage of the progressively refined predicted structures generated by the other search computing units in updating its current predicted structure.

To determine the final predicted structure 106 of the protein 104, the system 100 selects a predicted structure stored in the central memory 124. Generally, each predicted structure stored in the central memory 124 is associated with a score, and the system 100 determines the final predicted structure 106 by selecting a predicted structure in the central memory 124 based on the scores. For example, the system 100 may determine the final predicted structure 106 to be a predicted structure stored in the central memory 124 that has a highest score. The scores associated with the predicted structures stored in the central memory 124 may be, for example, backbone-atom quality scores or full-atom quality scores.

In some cases, determining full-atom quality scores may be more computationally intensive than determining backbone-atom quality scores. That is, determining a full-atom quality score of a predicted structure may require more memory, performing more arithmetic operations, or both, than determining a backbone-atom quality score of a predicted structure. To reduce computational resource consumption, each search computing unit may be configured to update the respective current predicted structure maintained by the search computing unit and update the central memory 124 based on backbone-atom quality scores. However, to determine the final predicted structure 106, the system may determine a full-atom quality score for each predicted structure stored in the central memory 124 and select the final predicted structure 106 based on these full-atom scores.

Generally, the local memory of each search computing unit and the central memory 124 can each be implemented in integrated or distributed formats. For example, the local memory of a search computing unit may be implemented as a data store that is physically remote from the other components of the search computing unit (e.g., the scoring system and the update system of the search computing unit). As another example, the central memory 124 may be implemented as a distributed data store. In this example, each search computing unit may maintain a separate "central memory", and the central memory 124 can be understood as the combination of the respective central memories maintained by each search computing unit.

In some cases, each predicted structure stored in the central memory may be associated with: (i) a set of hyper-parameters of the search computing unit that generated the predicted structure, and (ii) a quality score (e.g., backbone-atom quality score or full-atom quality score) of the predicted structure. The hyper-parameters of a search computing unit may include parameters specifying, e.g., a temperature hyper-parameter that characterizes how readily the search computing unit updates a current predicted structure (as will be described in more detail later), the number of search iterations performed by the search computing unit, and the like. Each search computing unit may repeatedly update its hyper-parameter values by sampling a set of hyper-parameter values associated with a predicted structure stored in the central memory in accordance with a probability distribution over the predicted structures stored in the central memory that is based on their respective quality scores. This can lead to automatic optimization of the hyper-parameters of the search computing units.

FIG. 2 is an illustration of an unfolded protein and a folded protein. The unfolded protein is a sequence e.g. a random coil of amino acids. The unfolded protein undergoes protein folding and folds into a unique 3D configuration. Protein structures often include stable local folding patterns, which may be referred to as secondary structure, such alpha helices (e.g., as depicted by 202) and beta sheets. The structure of the folded protein can be defined by the values of a set of structure parameters. For example, as depicted by 204, the structure parameters may be a sequence of 3D numerical coordinates (e.g., [x, y, z] coordinates) representing the respective positions of the backbone atoms in the amino acids in the folded protein in a given frame of reference.

Figure 3:
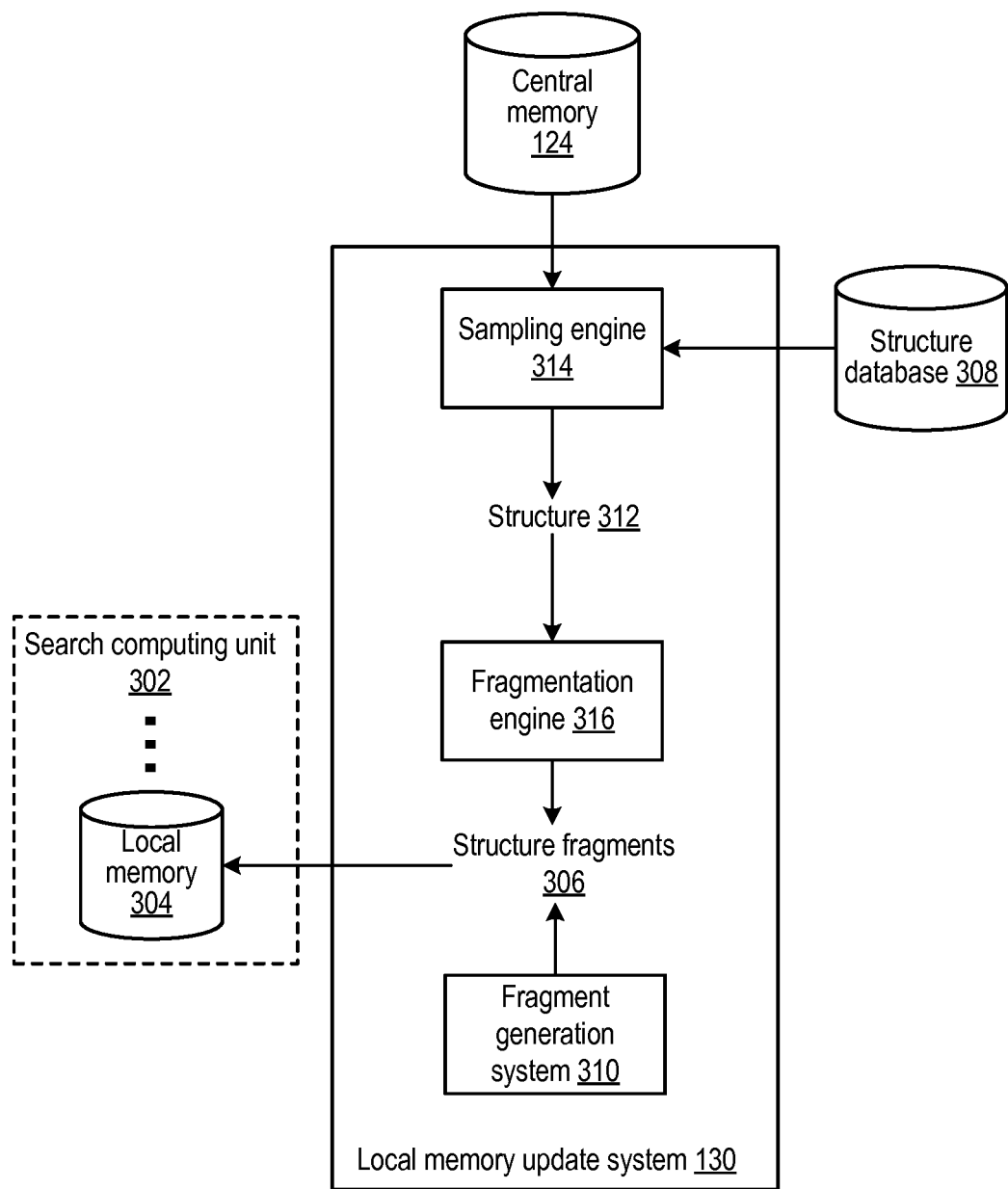
FIG. 3 is a block diagram of an example local memory update system.

FIG. 3 is a block diagram of an example local memory update system 130. The local memory update system 130 is an example of a system implemented as computer programs on one or more computers in one or more locations in which the systems, components, and techniques described below are implemented.

The local memory update system 130 is configured to initialize and later continually update the local memories of the search computing units (e.g., as described with reference to FIG. 1). The search computing unit 302 should be understood as any search computing unit included in the structure prediction system 100 (as described with reference to FIG. 1). Initializing the local memory 304 of the search computing unit 302 refers to storing multiple structure fragments 306 in the local memory 304 prior to the first search iteration performed by the search computing unit 302. Updating the local memory 304 of the search computing unit 302 refers to including different structure fragments 306 in the local memory 304 (and potentially removing structure fragments from the local memory 304) between search iterations performed by the search computing unit 302. For convenience, the description of the local memory update system 130 which follows refers to updating the local memory 304 of a search computing unit 302. However, the same procedures (as described below) used to update the local memory 304 of a search computing unit 302 can be analogously applied to initialize the local memory 304 of the search computing unit.

The local memory update system 130 updates the local memory 304 of the search computing unit 302 whenever a local memory update condition for the search computing unit 302 is satisfied. For example, a local memory update condition for the search computing unit 302 may be satisfied if the search computing unit 302 has performed a predetermined number of search iterations since the last time the local memory update system 130 updated the local memory 304 of the search computing unit 302. As another example, a local memory update condition for the search computing unit 302 may be satisfied if an average increase in the quality score of the current predicted structure maintained by the search computing unit 302 over a predetermined number of iterations is below a predetermined threshold. In this example, the average increase in the quality score of the current predicted structure being below the threshold may indicate that the local memory 304 needs to be "refreshed" with different structure fragments to enable the search computing unit 302 to continue to improve its current predicted structure.

In some implementations, the local memory update system 130 updates the local memory 304 by obtaining different structure fragments 306 and replacing the structure fragments currently in the local memory 304 with the different structure fragments. In some implementations, the local memory update system 130 updates the local memory 304 by obtaining different structure fragments 306 and partially replacing the structure fragments currently in the local memory 304 using a replacement policy. For example, the replacement policy may be a first-in-first-out (FIFO) replacement policy, where the structure fragments which were included in the local memory 304 earliest are replaced by the different structure fragments 306.

The local memory update system 130 may produce the structure fragments 306 to be included in the local memory 304 of the search computing unit 302 in a variety of different ways. For example, as will be described in more detail below, the local memory update system 130 may produce structure fragments by: (i) fragmenting predicted structures stored in the central memory 124, (ii) fragmenting actual structures stored in a structure database 308 of known structures of different proteins, (iii) generating the structure fragments using a generative neural network included in a fragment generation system 310, or (iv) a combination thereof. Fragmenting a structure of a protein refers to extracting one or more structure fragments from the structure of the protein.

In some implementations, the local memory update system 130 produces structure fragments 306 using predicted structures stored in the central memory 124 by the search computing units. More specifically, the local memory update system 130 may sample a structure 312 from the central memory 124 using a sampling engine 314 and process the structure 312 using a fragmentation engine 316 to determine multiple structure fragments from the structure 312.

The sampling engine 314 may sample a predicted structure from the central memory 124 in accordance with the scores associated with the predicted structures stored in the central memory 124. As described previously, each predicted structure stored in the central memory 124 may be associated with a quality score (e.g., a backbone-atom quality score or full-atom quality score). For example, to sample a predicted structure from the central memory 124, the sampling engine 314 may determine a probability distribution over the structures stored in the central memory 124 using their associated scores (e.g., by processing the scores using a soft-max function). The sampling engine can then sample the predicted structure from the central memory 124 in accordance with the determined probability distribution.

The fragmentation engine 316 can process a predicted structure sampled from the central memory 124 to generate multiple structure fragments 306. For example, the fragmentation engine 316 can generate the structure fragments 306 by partitioning the predicted structure into multiple structure fragments, where each structure fragment defines a structure of a consecutive sequence of amino acid residues in the amino acid sequence 102.

In some implementations, the local memory update system 130 produces structure fragments 306 using actual structures of different proteins stored in a structure database 308. The actual structures of the different proteins stored in the structure database 308 may have been determined using physical experimental methods such as x-ray crystallography. The local memory update system can sample (e.g., randomly) structures from the structure database 308 using the sampling engine 314 and process the sampled structures using the fragmentation engine 316 to determine structure fragments 306.

In some implementations, the local memory update system 130 generates structure fragments using a fragment generation system 310. As will be described further with reference to FIG. 4, the fragment generation system includes a generative neural network which is trained to generate network outputs defining realistic structure fragments 306. The fragment generation system 310 may be trained on a database of actual structures of different proteins (e.g., the structure database 308) using machine learning training techniques.

Figure 4:
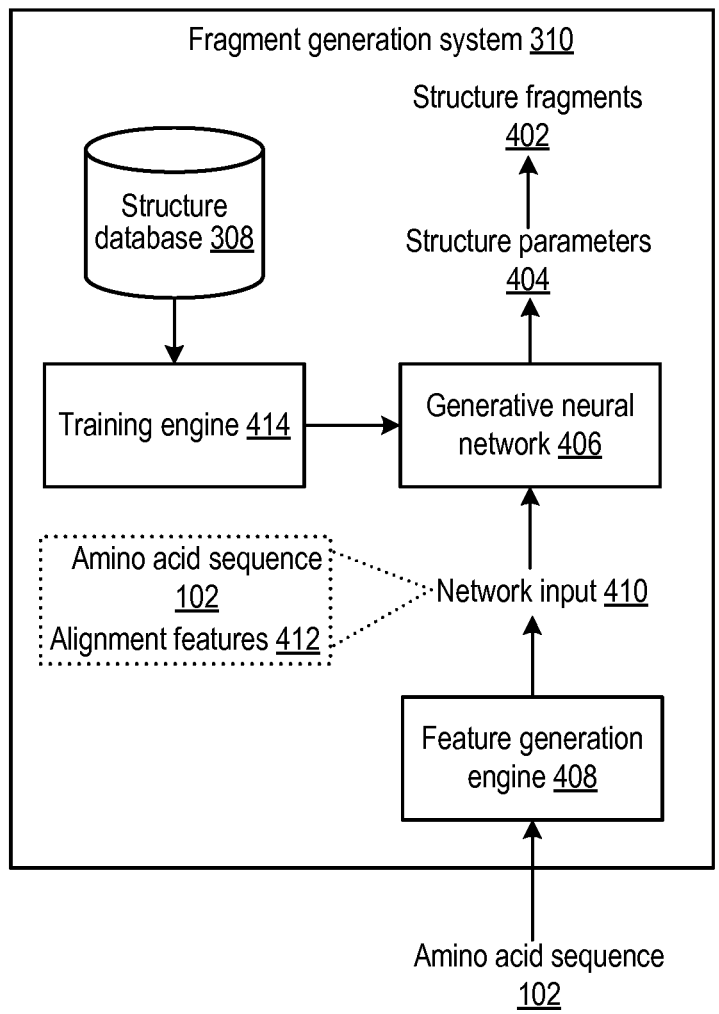
FIG. 4 is a block diagram of an example fragment generation system.

FIG. 4 is a block diagram of an example fragment generation system 310. The fragment generation system 310 is an example of a system implemented as computer programs on one or more computers in one or more locations in which the systems, components, and techniques described below are implemented.

The fragment generation system 310 is configured to receive an input including the amino acid sequence 102 and to process the input to generate realistic structure fragments 402 corresponding to the amino acid sequence 102. Each structure fragment 402 generated by the fragment generation system 310 is defined by structure parameters 404 produced by a generative neural network 406 and characterizes a realistic structure of a subsequence of amino acids in the amino acid sequence 102. Generally, the fragment generation system 310 can be used to generate large numbers of different realistic structure fragments 402 for any subsequence of amino acids in the amino acid sequence 102. A structure fragment can be understood to be "realistic" if the fragment broadly conforms to physical and biochemical constraints satisfied by actual protein structures found in the natural world. For example, a realistic structure fragment may be unlikely to include hydrophobic portions which would be exposed to water, since this configuration may be unlikely to occur in actual protein structures found in the natural world.

To generate a structure fragment 402, the fragment generation system 310 uses a feature generation engine 408 to generate a network input 410 for the generative neural network 406. The network input 410 can include a representation of the amino acid sequence 102, alignment features 412 corresponding to the amino acid sequence 102, or both. The alignment features 412 are derived from a multiple sequence alignment (MSA) of amino acid sequences from other proteins, e.g. homologous proteins, with a similar amino acid sequence 102. A MSA refers to a correspondence between amino acids in amino acid sequences from multiple other proteins with the amino acids in a similar sequence to the amino acid sequence 102 (e.g. the same apart from the insertion of gaps and/or the deletion of residues which do not align). Correlated changes in two amino acid residue positions across the sequences of the MSA can be indicative of which amino acids might be in contact. The feature generation engine 408 can generate the MSA by processing amino acid sequences of other proteins (e.g., which are stored in a database) using any appropriate computational sequence alignment technique (e.g., progressive alignment construction). The feature generation engine 408 can generate alignment features 412 including a representation of the MSA and statistical features (e.g., second order statistical features) derived from the MSA such as those described with reference to: S. Seemayer, M. Gruber, and J. Soding: "CCMpred: fast and precise prediction of protein residue-residue contacts from correlated mutations", Bioinformatics, 2014. The alignment features 412 can be 1D, 2D, or of any other appropriate dimensionality. Some example features are described later.

In some cases, the network input 410 includes data characterizing the entire amino acid sequence 102 (e.g., the network input 410 includes a representation of each amino acid in the amino acid sequence 102). In some other cases, the network input 410 includes data characterizing only a proper subset of the amino acids in the amino acid sequence 102 (i.e., rather than each amino acid in the amino acid sequence 102).

The fragment generation system 310 provides the network input 410 to a generative neural network 406 which is configured to process the network input 410 in accordance with current values of generative neural network weights to generate the structure parameters 404. The structure parameters may be, for example, backbone atom torsion angles or backbone atom coordinates for backbone atoms of a set of amino acids of the amino acid sequence 102. In some implementations, the structure parameters 404 define a structure of the entire amino acid sequence 102, and the fragment generation system 310 generates the structure fragments by fragmenting the structure parameters 404. In some implementations, the structure parameters 404 define the structure of a fragment (i.e., a proper subset) of the amino acid sequence 102.

To generate the structure parameters 404, the generative neural network is configured to process the network input 410 to generate, for each of the structure parameters 404, data defining a respective probability distribution over possible values of the structure parameter. For example, if the structure parameters 404 are backbone atom torsion angles, then the data defining the probability distribution over possible values of a structure parameter may be values of the parameters of a mixture of von Mises probability distributions. As another example, if the structure parameters 404 are backbone atom coordinates, then the data defining the probability distribution over possible values of a structure parameter may be the values of the mean and standard deviation of a Gaussian probability distribution. To generate each structure parameter 404, the fragment generation system 310 samples a value for the structure parameter in accordance with the probability distribution over possible values of the structure parameter.

Since the fragment generation system 310 generates the structure parameters 404 non-deterministically (i.e., by sampling from probability distributions), the fragment generation system can produce many different realistic structure fragments 402 from a given network input 410.

Generally, the generative neural network 406 can be implemented using any appropriate neural network architecture. A few examples follow.

In some cases, the generative neural network 406 may be configured to sequentially generate the probability distributions corresponding to each of the structure parameters 404 (i.e., in accordance with an ordering of the structure parameters 404). In these cases, to generate the probability distribution over possible values of a particular structure parameter, the generative neural network 406 may be configured to process the network input 410 and data defining previously determined values of one or more previous structure parameters. A previous structure parameter refers to a structure parameter that is previous to the particular structure parameter in the ordering of the structure parameters.

For example, the architecture of the generative neural network 406 may be derived from the architecture of a WaveNet generative neural network, as described with reference to: A. Van Den Oord, S. Dieleman, H. Zen, et al.: "A generative model for raw audio", arXiv:1609.03499v2, 2016. In this example, the generative neural network 406 architecture may include a convolutional subnetwork (including one or more masked convolutional layers) and an output layer. To generate the probability distribution over possible values of a given structure parameter, the convolutional subnetwork may process a convolutional subnetwork input including the network input 410 and previously determined values of one or more previous structure parameters to generate a convolutional subnetwork output. The output layer may be a soft-max layer which is configured to process the convolutional subnetwork output generated for the given structure parameter to generate an output defining a probability distribution over possible values for the given structure parameter.

In some cases, the generative neural network 406 may be configured to generate the probability distributions corresponding to each of the structure parameters 404 by sampling one or more latent variables from a latent variable space in accordance with a prior probability distribution. The generative neural network 406 can process the sampled latent variables and the network input 410 (e.g., including the representation of the amino acid sequence 102) to generate the probability distributions corresponding to each of the structure parameters 404. In these cases, the prior probability distribution can be an arbitrary probability distribution (e.g., a standard Gaussian with mean 0 and standard deviation 1) which is selected before the generative neural network 406 is trained.

For example, the architecture of the generative neural network 406 may be derived from the architecture of a variational autoencoder, in particular, a DRAW generative neural network, as described with reference to: K. Gregor, I. Danihelka, A. Graves, et al.: "DRAW: a recurrent neural network for image generation", arXiv: 1502.04623v2, 2015. In this example, the generative neural network architecture may include a recurrent decoder subnetwork. At each of multiple internal time steps, the generative neural network 406 may be configured to sample a latent variable in accordance with a prior probability distribution and provide the sampled latent variable as an input to the recurrent decoder subnetwork for the internal time step. The recurrent decoder subnetwork may be configured to update an internal state of the recurrent decoder subnetwork using the sampled latent variable and the network input 410. The generative neural network 406 may be configured to update the values of a "canvas" internal state of the generative neural network 406 using the updated internal state of the recurrent decoder subnetwork for the time step. After a final internal time step, the values of the canvas internal state of the generative neural network 406 define the probability distributions corresponding to each of the structure parameters 404. For example, the values of the canvas internal state may include respective values defining parameters of a respective probability distribution for each of the structure parameters 404.

An example architecture of a DRAW generative neural network 406 is illustrated with reference to FIG. 21.

In some cases, the generative neural network 406 may process the alignment features 412 included in the network input 410 using one or more convolutional layers (e.g., 2D convolutional layers) followed by a pooling layer.

The generative neural network 406 may be trained by a training engine 414 based on a database 308 of actual structures of different proteins (e.g., which are experimentally determined). More specifically, the values of the generative neural network weights may be repeatedly updated using machine learning training techniques (e.g., stochastic gradient descent) to cause the generative neural network 406 to generate structure parameters 404 which define realistic structure fragments 402 by processing network inputs 410.

The generative neural network 406, and more generally the fragment generation system 310, can be used as part of a local memory update system 310 in a structure prediction system 100, as previously described. However, the description in this specification should not be construed as limiting the generative neural network 406 and the fragment generation system 310 to use within a local memory update system 310 in a structure prediction system 100.

Figure 5:
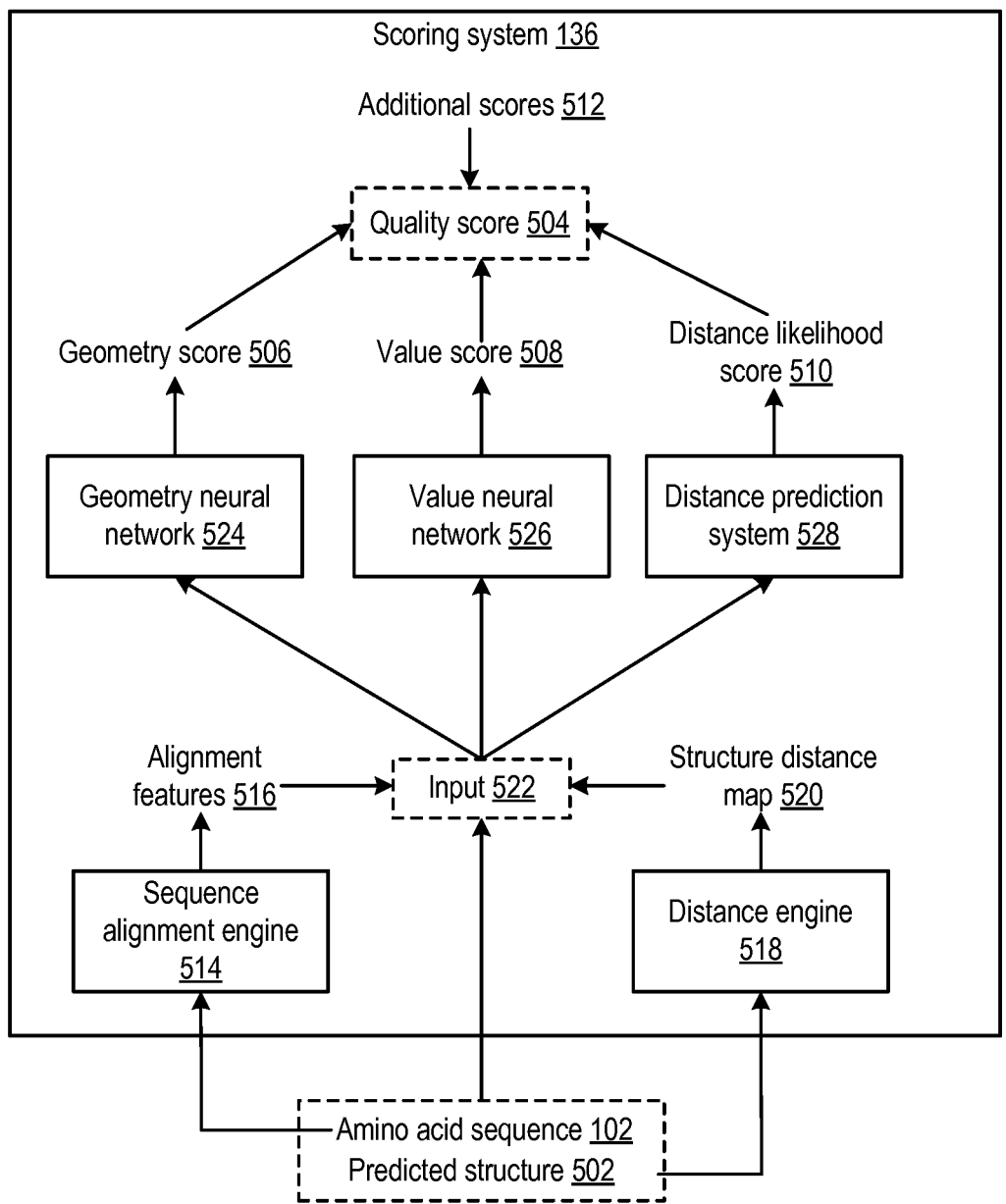
FIG. 5 is a block diagram of an example scoring system, e.g., that can be used by the structure prediction system described with reference to FIG. 1.

FIG. 5 is a block diagram of an example scoring system 136. The scoring system 136 is an example of a system implemented as computer programs on one or more computers in one or more locations in which the systems, components, and techniques described below are implemented.

The search computing units in the structure prediction system 100 determine respective quality scores for predicted structures using the scoring system 136. The scoring system 136 receives an input including: (i) the amino acid sequence 102, and (ii) a predicted structure 502 of the amino acid sequence 102 (e.g., an alternative predicted structure, as described with reference to FIG. 1). The scoring system 136 is configured to process the input to generate a quality score 504 for the predicted structure 502 which generally characterizes a quality of the predicted structure. For example, the system 136 may generate the quality score using one or more of: (i) a geometry score 506, (ii) a value score 508, (iii) a distance likelihood score 510, (iv) other additional scores 512 (all of which are described in more detail below).

As described with reference to FIG. 1, the amino acid sequence 102 and the predicted structure 502 may be represented in any appropriate numerical format. For example, the amino acid sequence 102 may be represented as a sequence of one-hot encoding vectors, where each one-hot encoding vector represents a different amino acid of the amino acid sequence 102. The predicted structure 502 may be represented by the values of a set of structure parameters (e.g., torsion angles between the backbone atoms of the amino acids in the amino acid sequence 102).

Optionally, the system 136 can include a sequence alignment engine 514, e.g. HHblits (Remmert et al., Nature Methods 9, 173, 2012), that is configured to process the amino acid sequence 102 to generate alignment features 516 which are derived from a multiple sequence alignment (MSA) of amino acid sequences from other proteins with similar sequences to amino acid sequence 102 (as described with reference to FIG. 4).

Optionally, the system 136 can include a distance engine 518 that is configured to process the predicted structure 502 to generate a structure distance map 520. The structure distance map 520 characterizes a respective distance (e.g., measured in angstroms) between each pair of amino acids in the amino acid sequence 102 when it is folded in accordance with the predicted structure 502. The distance between a first amino acid and a second amino acid in a structure refers to the distance between particular atoms (e.g., backbone atoms) in the first amino acid and the second amino acid when the amino acid sequence 102 is folded in accordance with the structure. In one example, the structure distance map may directly specify the distance between each pair of amino acids in the amino acid sequence 102. In another example, the structure distance map may specify whether each pair of amino acids in the amino acid sequence 102 are in contact, i.e., are separated by less than a predetermined threshold distance. The structure distance map 520 can be represented in any appropriate numerical format, for example, as matrix where the (i,j) entry of the matrix represents the distance between the i-th amino acid in the amino acid sequence 102 and the j-th amino acid in the amino acid sequence 102.

The system uses one or more of: (i) a representation of the amino acid sequence 102, (ii) the structure parameters defining the predicted structure 502, (iii) the alignment features 516, and (iv) the structure distance map 520, to generate respective inputs 522 for the geometry neural network 524, the value neural network 526, and the distance prediction system 528. In some cases, the representation of the amino acid sequence 102 and the structure parameters defining the predicted structure 502 are represented as one-dimensional (1D) features (i.e., features that are represented as linear sequences), while some of the alignment features 516 and the structure distance map 520 are represented as two-dimensional features (2D) (i.e., features that are represented as matrices). To generate the input 522, the system 136 may combine the 1D and 2D features by broadcasting and concatenating the 1D features along the rows and the columns of the matrix representation of the 2D features.

The system 136 processes the respective input 522 generated for the geometry neural network 524 in accordance with current values of geometry neural network weights to generate an output indicating a geometry score 506. The geometry score 506 is an estimate of a similarity measure between the predicted structure 502 of the amino acid sequence 102 and the actual structure of the amino acid sequence 102. For example, the similarity measure may be a root-mean-square-deviation (RMSD) between the structure parameters defining the predicted structure 502 of the amino acid sequence 102 and structure parameters defining the actual structure of the amino acid sequence 102. As another example, the similarity measure may be a global distance test (GDT) similarity measure. The GDT similarity can be defined as the fraction of backbone atoms in the amino acids in the amino acid sequence 102 whose position in the predicted structure 502 is within a predetermined distance of their position in the actual structure.

In some implementations, the geometry neural network 524 is configured to directly output the geometry score 506. In some implementations, the geometry neural network 524 is configured to generate an output defining a probability distribution over a predetermined set of geometry scores. In these implementations, the output of the geometry neural network 524 includes a respective probability value for geometry score in the predetermined set of geometry scores. The system 136 may determine the geometry score 506 to be a measure of central tendency (e.g., a mean, median, or mode) of the probability distribution over the predetermined set of geometry scores.

The system 136 processes the respective input 522 generated for the value neural network 526 in accordance with current values of value neural network weights to generate an output indicating a value score 508. The value score 508 is an estimate of a quality score characterizing a quality of a predicted structure generated by a search computing unit at a future search iteration if the current predicted structure maintained by the search computing unit at the current search iteration is the predicted structure 502. In some implementations, the future search iteration is a predetermined number of iterations after the current search iteration. In some implementations, the future search iteration is a final search iteration of the search computing unit (e.g., a search iteration where a search termination criterion is satisfied). The value score 508 enables a search computing unit using the scoring system 136 to update its current predicted structure in ways that may decrease the quality of the current predicted structure in the short term (e.g., over a few search iterations), but which may result in a higher quality final predicted structure.

In some implementations, the value neural network 526 is configured to directly output the value score 508. In some implementations, the value neural network 526 is configured to generate an output defining a probability distribution over a predetermined set of value scores. In these implementations, the output of the value neural network 526 includes a respective probability value for each of a value score in the predetermined set of value scores. The system 136 may determine the value score 508 to be a measure of central tendency (e.g., a mean, median, or mode) of the probability distribution over the predetermined set of value scores.

In some implementations, the scoring system 136 may generate respective inputs for the geometry neural network 524 and the value neural network 526 which include a distance map characterizing estimated distances between pairs of amino acid residues in the actual structure of the amino acid sequence 102. The distance map can be generated by a distance prediction neural network included in the distance prediction system 528, as will be described further with reference to FIG. 6.

The geometry neural network 524 and the value neural network 526 can be implemented in any appropriate neural network configuration. For example, the geometry neural network 524 and the value neural network 526 may include multiple convolutional neural network layers, attention layers, and residual blocks (e.g., 2D residual convolutional blocks). In some cases, the convolutional layers may include dilated convolutional filters to increase the sizes of their respective receptive fields. In a particular example, the geometry neural network 524 and the value neural network 526 may have an architecture that includes a sequence of multiple (e.g., 200) convolutional residual blocks (e.g., as described with reference to FIG. 20), followed by a mean pooling layer that outputs a single vector with a dimensionality that is agnostic to the length of the amino acid sequence, followed by a soft-max layer with 100 bins for the range [0,100].

The geometry neural network 524 can be trained using standard machine learning training techniques (e.g., stochastic gradient descent) based on a set of training data which includes multiple training examples. Each training example may include: (i) a training predicted structure of a protein, and (ii) a target geometry score that is a similarity measure between the training predicted structure of the protein and the actual structure of the protein. The target geometry score for the training predicted structure represents the geometry score that should be generated by the geometry neural network by processing an input 522 corresponding to the training predicted structure. The actual structure of the protein may have been determined, for example, through physical experiments.

In some implementations, the geometry neural network 524 is trained on a static set of training data which remains fixed throughout training of the geometry neural network 524. In these implementations, the training predicted structures included in the training examples may be determined, for example, by randomly perturbing the actual predicted structures of proteins. In some implementations, the geometry neural network 524 is trained on a set of training data which is repeatedly updated throughout training of the geometry neural network 524. In these implementations, at any given training iteration, some of the training predicted structures included in the training examples may be predicted structures generated by search computing units using quality scores based on geometry scores 506 generated by the geometry neural network 524 in accordance with the current values of the geometry neural network weights. By repeatedly updating the set of training data throughout training, the geometry neural network 524 can be trained to recognize and correct for inaccurate predicted structures generated by search computing units using quality scores generated in accordance with current values of the geometry neural network weights.

The value neural network 526 can be trained using standard machine learning training techniques (e.g., stochastic gradient descent) based on a set of training data which includes multiple training examples. Each training example may include: (i) a training predicted structure of a protein, and (ii) a target value score that is a quality score characterizing a quality of a future predicted structure of the protein that is determined by repeatedly updating the training predicted structure of the protein. The target value score for the training predicted structure represents the value score that should be generated by the value neural network 526 by processing an input 522 corresponding to the training predicted structure.

In some implementations, the value neural network 526 is trained on a static set of training data which remains fixed throughout training of the value neural network 526. In these implementations, the set of training data may be determined by computing a large number of predicted structure trajectories (i.e., sequences of predicted structures) for different proteins using search computing units (e.g., as described with reference to FIG. 1). To determine a particular training example, a particular predicted structure from a predicted structure trajectory may be selected as the training predicted structure for the particular training example. The target quality value score for the particular training example may be selected to be the quality score of a later predicted structure in the predicted structure trajectory. For example, the target value score may be selected to be the quality score of a last predicted structure in the predicted structure trajectory.

In some implementations, the value neural network 526 is trained on a set of training data which is repeatedly updated throughout the training of the value neural network 526. In these implementations, the set of training data may be updated by generating a large number of predicted structure trajectories for different proteins using quality scores based on value scores 508 generated by the value neural network 526 in accordance with the current values of the value neural network weights. The set of training data may be updated by generating new training examples from these predicted structure trajectories (e.g., using the previously described method for determining training examples form predicted structure trajectories). By repeatedly updating the set of training data throughout training, the value neural network 526 can be trained to recognize and correct for inaccurate predicted structures generated by search computing units using quality scores generated in accordance with current values of the value neural network weights.

Typically, the set of training data used to train the geometry neural network 524 includes training examples with training predicted structures corresponding to proteins for which a "ground-truth" structure for the protein is known (e.g., by physical experiments). Specifically, the ground-truth structure for the protein must be known to determine the target geometry scores for the training examples. In contrast, the set of training data used to train the value neural network may include training examples with training predicted structures corresponding to proteins for which the ground-truth structure for the protein may be unknown. Specifically, the ground-truth structure for the protein does not need to be known to determine the target value scores for the training examples.

The geometry neural network 524 and the value neural network 526 may be trained using a contrastive divergence training procedure. In this case, the geometry score generated by the geometry neural network may not be a direct estimate of a particular similarity measure between the predicted structure 502 and the actual structure of the protein. Similarly, the value score generated by the value neural network may not be a direct estimate of a particular quality score of a future predicted structure. The description of the geometry neural network 524 and the value neural network 526 in this specification should be understood to include the case where the geometry neural network 526 and the value neural network 526 are trained using a contrastive divergence training procedure.

Any appropriate supervised loss objective function can be used during training of the geometry neural network and the value neural network, e.g., a cross-entropy loss objective function or a squared-error loss objective function. In a particular example, a geometry neural network configured to generate relative geometry scores may be trained using a logistic loss objective function that characterizes whether the ranking of predicted structures defined by the relative importance scores are consistent with the actual ranking of the predicted structures.

The system 136 processes the respective input 522 generated for the distance prediction system 528 using the distance prediction system 528 to generate a distance likelihood score 510. As will be described further with reference to FIG. 6, the distance likelihood score 510 defines a likelihood of the predicted structure 502 based on the difference between: (i) distances between pairs of amino acids in the amino acid sequence 102 in the predicted structure 502, and (ii) estimated distances between pairs of amino acids in the actual structure of the amino acid sequence 102.

The system 136 may generate additional scores 512 in addition to the geometry score 506, the value score 508, and the distance likelihood score 510. For example, the additional scores may include scores based on whether hydrophobic parts of the predicted structure 502 would be exposed to water if the amino acid sequence 102 were folded in accordance with the predicted structure 502. In this example, a predicted structure 502 which includes hydrophobic regions that would be exposed to water would result in a lower score since this predicted structure 502 would probably be dissimilar to the actual structure of the amino acid sequence 102. As another example, the additional scores may include scores based on a similarity measure between: (i) the predicted structure 502, and (ii) a predicted structure of the protein generated as an output of a one-shot prediction neural network. In this example, the one-shot prediction neural network may be configured to process an input including a representation of the amino acid sequence 102 and the alignment features 516 to directly generate a predicted structure of the protein.

The system 136 may determine the quality score 504 for the predicted structure 502 by combining one or more of: the geometry score 506, the value score 508, the distance likelihood score 510, and the additional scores 512. For example, the system 136 may determine the quality score as a linear combination of the geometry score 506, the value score 508, the distance likelihood score 510, and the additional scores 512, where the coefficients of the linear combination are adjustable system hyper-parameters.

The geometry neural network 524, the value neural network 526, and the distance prediction system 528 can be used as part of a scoring system 136, as previously described. However, the description in this specification should not be construed as limiting the geometry neural network 524, the value neural network 526, and the distance prediction system 528 to use within a scoring system 136. Moreover, as will be described in more detail below, different variations of the geometry neural network 524 and value neural network 526 can be implemented for use within or outside a scoring system 136.

In some implementations, the geometry neural network 524 may be configured to process an input 522 which includes: (i) data defining an amino acid sequence of a protein, (ii) data defining a first predicted structure of the protein, and (iii) data defining a second predicted structure of the protein. In general, the first predicted structure of the protein is different than the second predicted structure of the protein. The data defining the first predicted structure of the protein and the data defining the second predicted structure of the protein may include respective values of structures parameters (e.g., torsion angles or coordinates of backbone atoms in the amino acid sequence of the protein). Moreover, the input 522 to the geometry neural network 524 may include alignment features 516 and respective structure distance maps 520 corresponding to the first and second predicted structures of the protein. The geometry neural network 524 may be configured to process the input to generate an output characterizing a relative geometry score between the first predicted structure of the protein and the second predicted structure of the protein.

The relative geometry score may define a prediction for whether a similarity measure between the first predicted structure and the actual structure of the protein exceeds a similarity measure between the second predicted structure and the actual structure of the protein. That is, the relative geometry score may define a prediction for whether the first predicted structure of the second predicted structure is more accurate. In a particular example, the relative geometry score may be positive (respectively, negative) to indicate a prediction that the similarity measure between the first predicted structure and the actual structure of the protein exceeds (respectively, does not exceed) a similarity measure between the second predicted structure and the actual structure of the protein.

When the scoring system 136 is being used by a search computing unit, at each search iteration, the geometry neural network 524 may be configured to generate a relative geometry score for each alternative predicted structure. To generate the relative geometry score for an alternative predicted structure, the geometry neural network 524 may be configured to jointly process the data defining the current predicted structure of the search computing unit at the search iteration and the data defining the alternative predicted structure. Thereafter, the relative geometry score can be used (as previously described) to determine the quality score 504 of the alternative predicted structure.

In some implementations, the value neural network 526 may be configured to process an input 522 which includes: (i) data defining an amino acid sequence of a protein, (ii) data defining a first predicted structure of the protein, and (iii) data defining a second predicted structure of the protein. In general, the first predicted structure of the protein is different than the second predicted structure of the protein. The data defining the first predicted structure of the protein and the data defining the second predicted structure of the protein may include respective values of structures parameters (e.g., torsion angles or coordinates of backbone atoms in the amino acid sequence of the protein). Moreover, the input 522 to the value neural network 526 may include alignment features 516 and respective structure distance maps 520 corresponding to the first and second predicted structures of the protein. The value neural network 526 may be configured to process the input to generate an output characterizing a relative value score between the first predicted structure of the protein and the second predicted structure of the protein.

The relative value score may define a prediction for whether a quality score characterizing a quality of a first future predicted structure of the protein exceeds a quality score characterizing a quality of a second future predicted structure of the protein. The first future predicted structure of the protein refers to a predicted structure generated by iteratively modifying the first predicted structure of the protein (e.g., by a search computing unit) over multiple search iterations. The second future predicted structure of the protein refers to a predicted structure generated by iteratively modifying the second predicted structure of the protein (e.g., by a search computing unit) over multiple search iterations. That is, the relative value score may define a prediction for whether the first predicted structure of the second predicted structure can be iteratively modified (e.g., by a search computing unit) to lead to a "better" (e.g., more accurate) future predicted structure. In a particular example, the relative value score may be positive (respectively, negative) to indicate a prediction that the quality score of the first future predicted structure of the protein exceeds (respectively, does not exceed) the quality score of the second future predicted structure of the protein.

When the scoring system 136 is being used by a search computing unit, at each search iteration, the value neural network 526 may be configured to generate a relative value score for each alternative predicted structure. To generate the relative value score for an alternative predicted structure, the value neural network 526 may be configured to jointly process the data defining the current predicted structure of the search computing unit at the search iteration and the data defining the alternative predicted structure. Thereafter, the relative value score can be used (as previously described) to determine the quality score 504 of the alternative predicted structure.

As described earlier, a backbone-atom quality score of a predicted structure is based solely on the backbone atoms in the amino acids, while a full-atom quality score is determined with reference to all of the atoms in each of the amino acids. The scoring system 136 may include respective implementations of the geometry neural network, the value neural network, and the distance prediction system which are used to generate full-atom quality scores, and a respective implementation of the geometry neural network, the value neural network, and the distance prediction system which are used to generate backbone-atom quality scores. For example, the full-atom implementation of the geometry neural network may be configured to process a predicted structure 502 which specifies the position of every atom in each amino acid in the amino acid sequence 102 to generate a full-atom geometry score. The full-atom geometry score may define a similarity measure between the predicted structure 502 and the actual structure of the protein based on every atom in each amino acid of the protein. The backbone-atom implementation of the geometry neural network may be configured to process a predicted structure 502 which specifies the position of the backbone atoms of the amino acids in the amino acid 102 to generate a backbone-atom geometry score. The backbone-atom geometry score may define a similarity measure between the predicted structure 502 and the actual structure of the protein based on the backbone atom in each amino acid of the protein.

Figure 6:
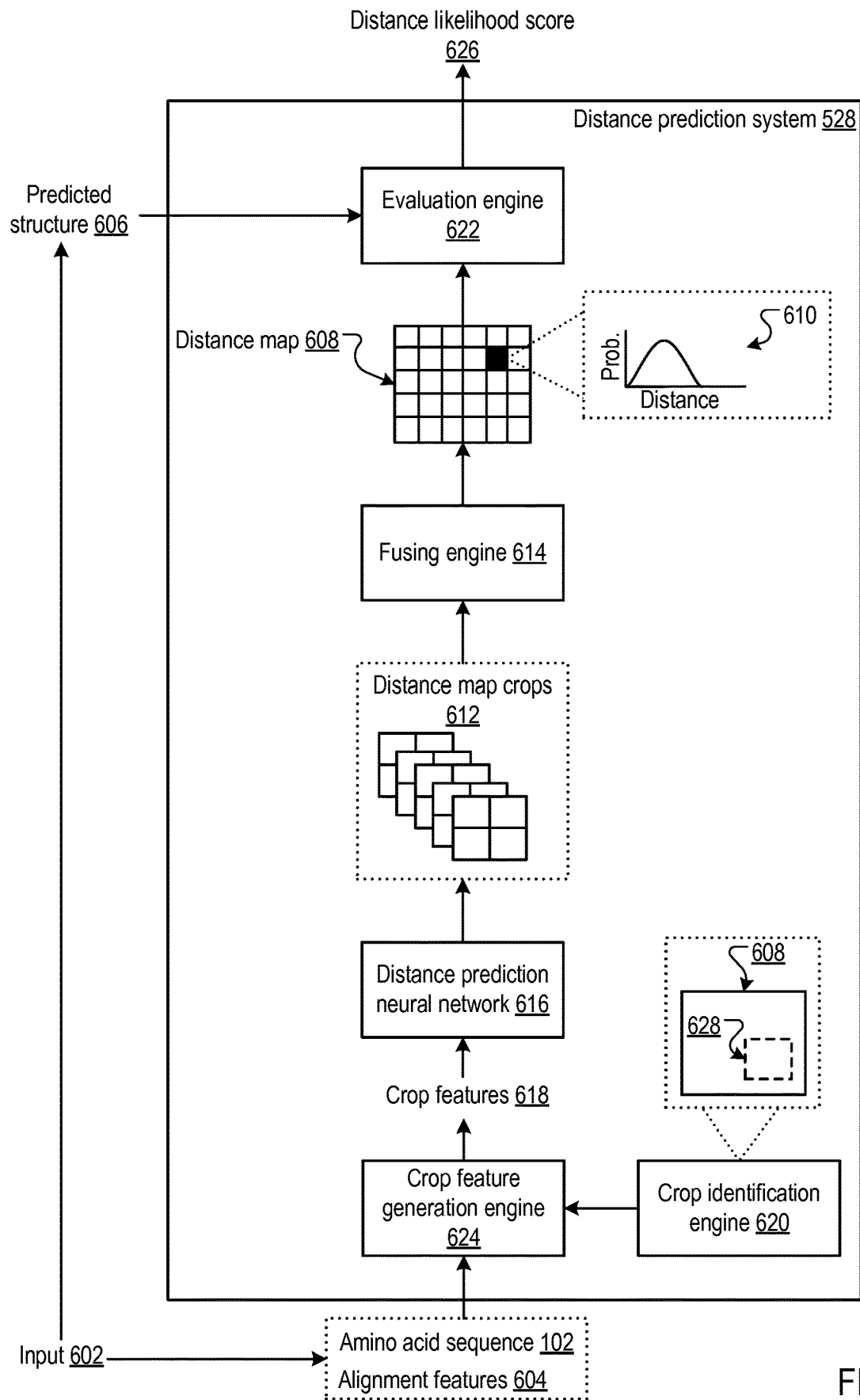
FIG. 6 is a block diagram of an example distance prediction system.

FIG. 6 is a block diagram of an example distance prediction system 528. The distance prediction system 528 is an example of a system implemented as computer programs on one or more computers in one or more locations in which the systems, components, and techniques described below are implemented.

The distance prediction system 528 is configured to receive an input 602 (e.g., as described with reference to FIG. 5) including a representation of the amino acid sequence 102, alignment features 604, and a predicted structure 606 of the amino acid sequence 102. The system 528 is configured to process the input 602 to generate a distance likelihood score 510. The distance likelihood score 510 defines a likelihood of the predicted structure 606 based on the difference between: (i) distances between pairs of amino acids in the amino acid sequence 102 in the predicted structure 606, and (ii) estimated distances between pairs of amino acids in the amino acid sequence 102 in the actual structure of the amino acid sequence 102.

The alignment features are determined based on an MSA for the amino acid sequence and may include profile features (that may be 1-D) with the position-specific substitution probabilities for each residue as well as covariation features, e.g., the parameters of a regularized pseudo-likelihood trained Potts model (e.g., similar to CCMPred) that are fitted on the MSA. The features may include the Frobenius norm of the parameters of the Potts model and the raw parameter values for each residue pair i,j. The alignment features may include features explicitly representing gaps and deletions in the MSA e.g. a gap matrix in which the (i,j)th element counts the number of times where gaps occur in both the ith and jth position (the variance of the covariance is greater with more gaps), and/or a deletion probability e.g. the probability of a deletion happening to the right of a residue position.

Additional profile features may be extracted using PSI-BLAST. The number of amino acid sequences in the MSA may be an additional alignment feature. The alignment features and the representation of the amino acid sequence can be represented as a two-dimensional array of features, where each i,j feature is the concatenation of the one-dimensional features for both the i and j residues as well as the two-dimensional features for the residue pair i,j. The alignment features described here can be used as inputs for each of the scoring neural networks described in this specification, e.g., the geometry neural network, the value neural network, and the structure prediction neural network.

Thus in a particular example implementation the input features to the distance prediction system 528 may comprise the number of amino acid sequences in the MSA; sequence length features comprising the representation of the amino acid sequence 102 (21D), the deletion probability (1D), a residue index, and profiles such as a PSI-BLAST profile (21D), an HHblits profile (22D), HHblits bias, a non-gapped profile (21D), an HMM profile (30D), and a Potts model bias (30D); and sequence length features such as the gap matrix (1D), the Frobenius norm (1D), and the Potts model parameters (484D).

Figure 19:
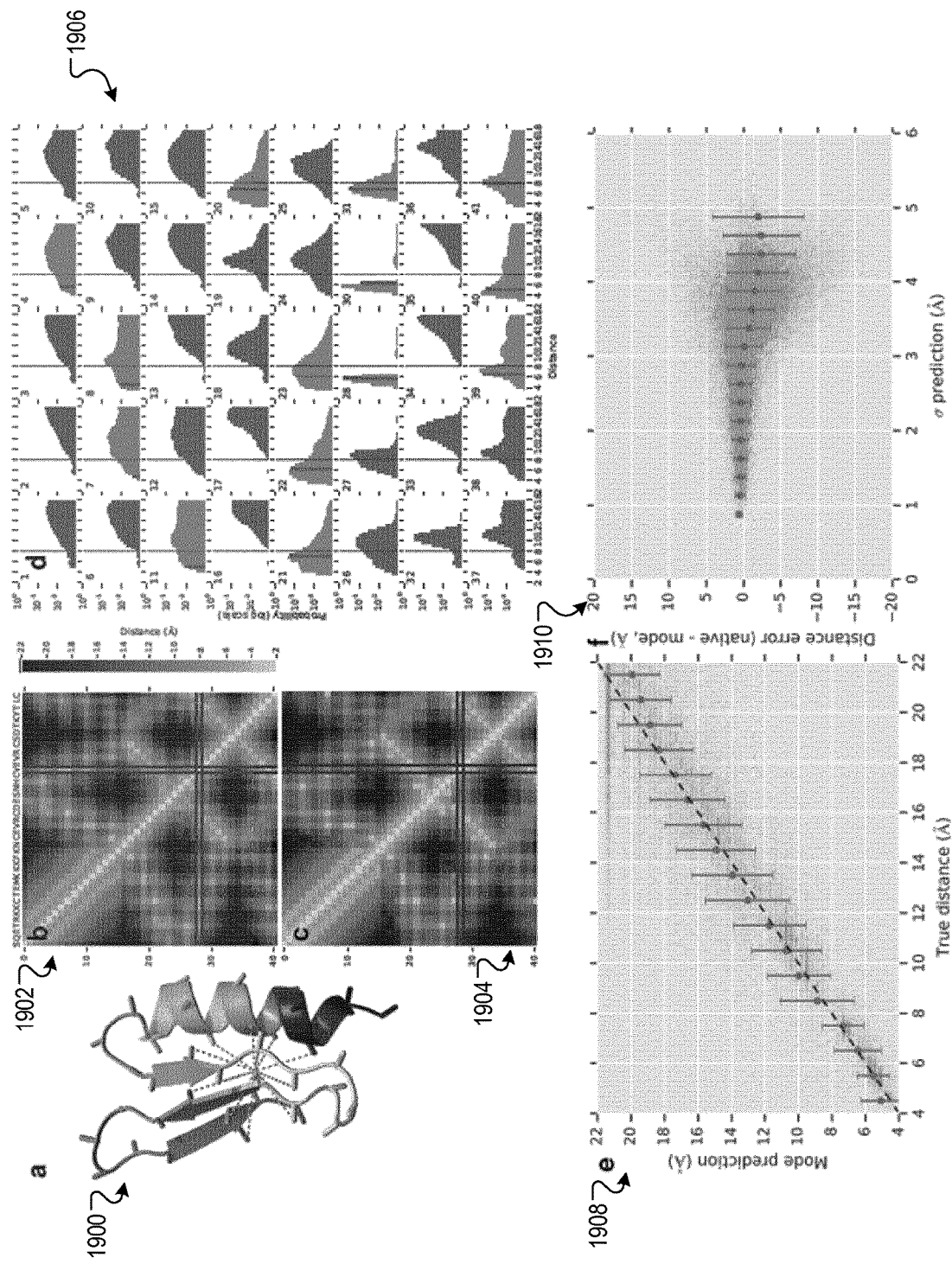
FIG. 19 illustrates aspects of an example distance map.

To generate the distance likelihood score 510, the system 528 generates a distance map 608 which characterizes estimated distances between each pair of amino acids in the amino acid sequence 102 in the actual (e.g., experimentally determined) structure of the amino acid sequence 102. The distance map 608 can be represented as a matrix where the (i, D entry of the matrix includes data characterizing the estimated distance between the i-th amino acid in the amino acid sequence 102 and the j-th amino acid in the amino acid sequence 102 in the actual structure of the amino acid sequence 102. In some implementations, for each pair of amino acids in the amino acid sequence 102, the distance map 608 characterizes the estimated distance between the pair of amino acids as a binary variable. In these implementations, the binary variable may have value 1 if the estimated distance between the pair of amino acids is less than a predetermined threshold (e.g., 8 angstroms), and the binary value may have value 0 otherwise. In some implementations, for each pair of amino acids in the amino acid sequence 102, the distance map 608 characterizes the estimated distance between the pair of amino acids as a continuous-valued number (e.g., representing the distance in angstroms). In some implementations, for each pair of amino acids in the amino acid sequence 102, the distance map 608 characterizes the estimated distance between the pair of amino acids by a probability distribution over a predetermined set of distance ranges (e.g., the probability distribution 610). In these implementations, the probability distribution includes a respective probability value for each distance range in the predetermined set of distance ranges. For example in one particular implementation the distance between the pair of amino acids is the distance between the amino acid residues' $C_\beta$ atoms ($C_\alpha$ for glycine, which lacks a beta carbon). In one particular implementation the distance range 2-22 Å is quantized into 64 equal bins (as illustrated in FIG. 19 described later).

To generate the distance map 608, the system 528 may generate a set of distance map crops 612. Each distance map crop 612 is an estimate of a proper subset of the full distance map 608. More specifically, each distance map crop 612 characterizes the estimated distances between (i) amino acid residues in each of one or more first positions in the amino acid sequence 102, and (ii) amino acid residues in each of one or more second positions in the amino acid sequence 102, where the first positions, the second positions, or both are a proper subset of the total positions in the amino acid sequence 102. The first positions can be understood as identifying respective rows of the distance map matrix 608, and the second positions can be understood as identifying respective columns of the distance map matrix 608. As will be described in more detail below, the system 528 combines the distance map crops 612 using a fusing engine 614 to generate the full distance map 608.

Each distance map crop is generated as the output of a distance prediction neural network 616. The distance prediction neural network 616 is configured to generate a distance map crop by processing crop features 618 which characterize the amino acids in each of the first positions and second positions in the amino acid sequence corresponding to the distance map crop. The crop features 618 may be generated by a crop feature generation engine 624. The crop feature generation engine 624 is configured to extract the components of (i) a representation of the amino acid sequence 102, and (ii) the alignment features 604, corresponding to the amino acids in the first positions and the second positions in the amino acid sequence 102 corresponding to the distance map crop. In some cases, the crop feature generation engine is additionally configured to extract the on-diagonal components of the alignment features corresponding to the amino acids in the first positions and the amino acids in the second positions in the amino acid sequence. Using features close to the diagonal (i=j) can help to encode local structure e.g. secondary structure.

If the distance prediction neural network 616 were configured to directly generate the distance map 608 by processing the entire representation of the amino acid sequence 102 and the alignment features 604, then the architecture of the distance prediction neural network 616 would be restricted by the longest amino acid sequence that must be modeled. By processing crop features 618 to generate distance map crops 612 (which the system 528 fuses to generate the full distance map 608), the distance prediction neural network 616 can have a more complex architecture (e.g., with more neural network layers) than it otherwise would, thereby enabling more precise distance map 608 estimation.

The distance prediction neural network 616 can be implemented in any appropriate neural network configuration. For example, the distance prediction neural network 616 may include multiple convolutional neural network layers, attention layers, and residual blocks. In some cases, the convolutional layers may include dilated convolutional filters to increase the sizes of their respective receptive fields. In a particular example, the distance prediction neural network may be a deep two-dimensional dilated convolutional residual network. In this example, the distance prediction network is two-dimensional throughout and uses 220 residual blocks with dilated convolutions. An example architecture of the residual blocks is described in more detail with reference to FIG. 20.

The distance prediction neural network 616 can be trained based on a training data set including multiple training examples. Each training example includes a training network input and a target distance map corresponding to the training network input. The training network input is derived from a training protein with a known structure. In some implementations, the target distance map characterizes actual distances between amino acid residues in the structure of the training protein. In some other implementations, the target distance map characterizes estimated distances between amino acids residues in the structure of the training protein which are generated by a "teacher" neural network by processing the training input. In these implementations, the teacher neural network may be a more complex neural network than the distance prediction neural network 616 (e.g., a neural network with more layers, more parameters, or both) which is trained to generate distance maps characterizing actual distances between amino acid residues in the structures of proteins. By training the distance prediction neural network 616 to generate outputs matching the outputs of a teacher neural network (i.e., in a distillation learning framework), the distance prediction neural network 616 may be trained more effectively than it otherwise would be. The objective function used to train the distance prediction neural network 616 may be a cross-entropy objective function.

In some cases, the system 528 may augment the training data set by generating new training examples including training distance maps which are randomly perturbed from training distance maps originally included in the training data set. In some cases, the system 528 may augment the training data set by generating new training examples where the alignment features included in the training examples are generated using a random subsampling of the full MSA for the amino acid sequence.

The system 528 includes a crop identification engine 620 which is configured to select the distance map crops 612 to be generated by the distance prediction neural network 616. More specifically, the crop identification engine 620 generates an output including the first positions and the second positions corresponding to each distance map crop (e.g., the distance map crop 628 of the distance map 608). In some implementations, the crop identification engine 620 is configured to generate randomly selected first positions and second positions for each distance map crop. If applied during training this approach can act as a form of data augmentation. In some implementations, the crop identification engine 620 is configured to identify a predetermined set of distance map crops which are selected to "cover" the distance map 608 (i.e., so that the distance between each possible pair of amino acids in the amino acid sequence 102 is characterized by at least one distance map crop 612). Optionally an input to the distance prediction neural network may include an encoding of a relative and/or absolute position of a crop.

In one example, the crop identification engine 620 selects distance map crops of size 64×64, that is, distance map crops that characterize the pairwise distances between two groups of 64 consecutive residues. However a crop need not be square.

After generating the distance map crops 612, the system 528 "fuses" (i.e., combines) the distance map crops 612 using a fusing engine 614 to determine the full distance map 608. In some implementations, the system 528 determines the full distance map 608 to be an average of the distance map crops 612. For example, for a given pair of amino acids in the amino acid sequence 102, the system 528 may determine the distribution of the estimated distance between the given pair of amino acids characterized by the distance map 608 to be an average of the distributions of the estimated distances between the given pair of amino acids characterized by each of the distance map crops 612. In this example, the average excludes the distance map crops which do not characterize the distance between the given pair of amino acids. Also in this example, the average may be weighted more heavily towards distance map crops that are more centered on the given pair of amino acids; this can help reduce edge effects. In some implementations, the system 528 determines the full distance map 608 by processing the distance map crops 612 using a fusing neural network in accordance with current values of fusing neural network parameters to generate an output including the full distance map 608.

In some cases, the system 528 generates a set of distance map crops 612 using multiple distance prediction neural networks that are trained independently with different hyperparameters. Using such an ensemble can further improve accuracy.

The system includes an evaluation engine 622 which is configured to determine a distance likelihood score 626, e.g.

the distance likelihood score 510, from the predicted structure 606 and the distance map 608. For example, the evaluation engine 622 may determine the distance likelihood score 626 based on a sum of squared differences between, for each pair of amino acids in the amino acid sequence 102, a continuous-valued estimate for the distance between the pair of amino acids according to the distance map 608 and the distance between the pair of amino acids in the predicted structure 606. As another example, the evaluation engine 622 may determine the distance likelihood score 626 based on, for each pair of amino acids in the amino acid sequence 102, a probability according to the distance map 608 that the pair of amino acids are separated by the distance defined by the predicted structure 606. In a particular example, the evaluation engine 622 may determine the distance likelihood score s as:

$$s = \prod_{(i,j)} p_{i,j}(d_{i,j}) \quad (1)$$

where the product is over pairs of amino acids in the amino acid sequence 102 indexed by (i,j) and $p_{i,j}(d_{i,j})$ denotes a probability that the amino acid pair indexed by (i,j) are separated by the distance $d_{i,j}$ defined by the predicted structure 606 according to the corresponding probability distribution $p_{i,j}$ over possible distance ranges between the pair of amino acid residues (i,j) defined by distance map 608. As another example, the evaluation engine 622 may determine the distance likelihood score based in part on a "reference" distance map, as will be described in more detail below.

A reference distance map characterizes estimated distances which are generally expected between each pair of amino acids in the amino acid sequence 102, but which are determined without reference to the identities of the specific amino acids in the amino acid sequence 102. For example, for each pair of amino acids in the amino acid sequence 102, the reference distance map may characterize the estimated distance between the pair of amino acids based on the positions and relative offsets of the amino acids in the amino acid pair. The position of a given amino acid refers to the number of other amino acids between the given amino acid and the first amino acid in the amino acid sequence. The relative offset between two amino acids refers to the number of other amino acids between the two amino acids in the amino acid sequence. The reference distance map can characterize the estimated distances between pairs of amino acids in the same manner as the distance map 608 (e.g., as a continuous-valued number or as a probability distribution over a predetermined set of distance ranges).

The distance prediction system 528 may generate the reference distance map using a protein structure database of actual structures of different proteins. In a particular example, the distance prediction system 528 may determine a reference probability distribution over a predetermined set of distance ranges between a pair of amino acids based on each pair of amino acids included in a respective protein structure in the protein structure database with the same positions and relative offset. In this example, the reference distance map may include a respective reference probability distribution characterizing the estimated distances between each pair of amino acids in the amino acid sequence 102.

The evaluation engine 622 may determine the distance likelihood score 626 using the reference distance map as:

$$s = \log \prod_{(i,j)} p_{i,j}(d_{i,j}) - \log \prod_{(i,j)} p_{i,j}^r(d_{i,j}) \quad (2)$$

where the product is over pairs of amino acids in the amino acid sequence 102 indexed by (i,j), $p_{i,j}(d_{i,j})$ denotes a probability that the amino acid pair indexed by (i,j) are separated by the distance $d_{i,j}$ defined by the predicted structure 606 according to a corresponding probability distribution $p_{i,j}$ over possible distance ranges between the pair of amino acid residues (i,j) defined by distance map 608, $p_{i,j}^r(d_{i,j})$ denotes a probability that the amino acid pair indexed by (i,j) are separated by the distance $d_{i,j}$ defined by the predicted structure 606 according to the corresponding reference probability distribution $p_{i,j}^r$ over possible distance ranges between the pair of amino acid residues (i,j) defined by reference distance map (as described above). By determining the distance likelihood score 626 using the reference distance map, the distance likelihood score 626 can characterize deviations between the reference distance map and the distance map generated by a distance prediction neural network 616 (as described further with reference to FIG. 6). For example, as also described later the distance likelihood score 626 determined using the reference distance map may be subtracted in the log domain from a distance likelihood score determined using a distance likelihood score determined using the amino acid identities, to correct for over-representation of the prior distance distribution.

Generally, the distance likelihood score 626 can be any numerical value determined from the predicted structure 606 and the distance map 608 which characterizes a quality of the predicted structure.

By characterizing the distances between pairs of amino acids using continuous-valued distance estimates or distance range probability distributions (i.e., rather than binary variables), the system 528 can generate a distance likelihood score 626 which conveys more precise information about how closely the predicted structure 606 conforms with the actual structure of the amino acid sequence 102.

In some cases, the distance prediction neural network 616 may be configured to generate additional auxiliary outputs (e.g., in addition to distance map crops). For example, the distance prediction neural network may be configured to generate outputs characterizing torsion angles between amino acids in each of the first positions and second positions in the amino acid sequence corresponding to a distance map crop. As another example, the distance prediction neural network may be configured to generate outputs characterizing estimated secondary structures (β-sheet or α-helix secondary structures and/or a coil structure) corresponding to amino acids in each of the first positions and second positions in the amino acid sequence corresponding to a distance map crop. As another example, the distance prediction neural network may be configured to generate outputs characterizing the accessible surface area of the protein (i.e., the surface area of the protein accessible to a solvent). Training the distance prediction neural network to accurately generate additional auxiliary outputs may cause the distance prediction neural network to generate more accurate distance map crops.

Figure 7:
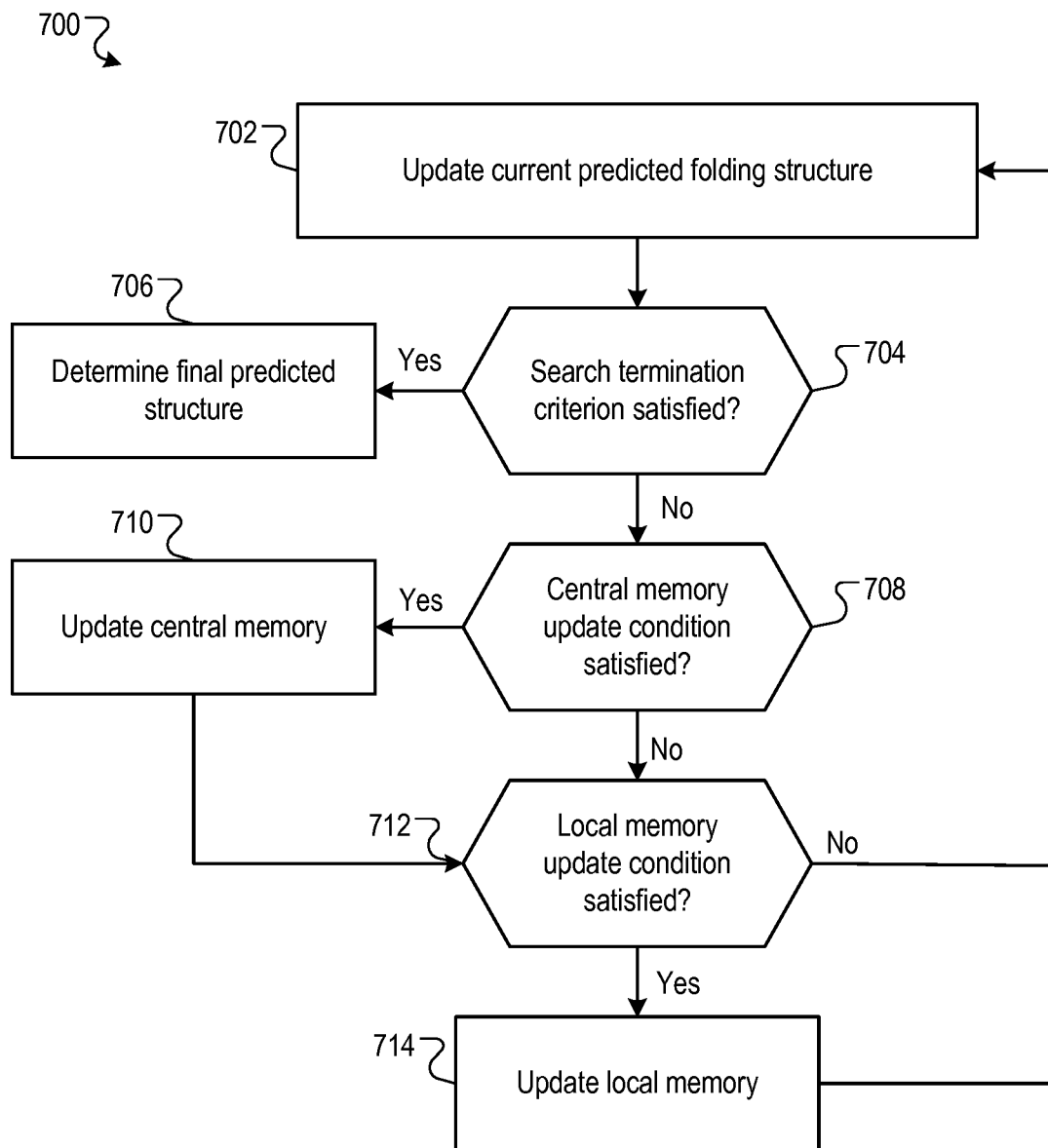
FIG. 7 is a flow diagram of an example process for generating a respective trajectory of predicted structures of a protein by iteratively updating a current predicted structure of the protein.

FIG. 7 is a flow diagram of an example iterative process for generating a trajectory (i.e., sequence) of predicted structures of a protein by iteratively updating a current predicted structure of the protein. For convenience, the process 700 will be described as being performed by a system of one or more computers located in one or more locations. For example, a search computing unit, e.g., the search computing units 108 and 110 of FIG. 1, appropriately programmed in accordance with this specification, can perform the process 700.

The system updates a current predicted structure of the protein using a local memory that is configured to store a collection of structure fragments (702). Each structure fragment characterizes a predicted structure of a subsequence (i.e., fragment) of amino acids in the amino acid sequence of the protein. To update the current predicted structure of the protein, the system generates an alternative predicted structure for the protein by "perturbing" the current predicted structure of the protein using a structure fragment from the local memory. An example process for determining whether to update a current predicted structure to an alternative predicted structure is described with reference to FIG. 8.

The system determines whether a search termination criterion is satisfied (704). As an example, the system may determine the search termination criterion is satisfied when the system has performed a predetermined number of iterations of the steps of the process 700. As another example, the system may determine the search termination criterion is satisfied if an average increase in a quality score of the current predicted structure over a predetermined number of iterations (e.g., the previous ten iterations) is below a certain threshold. The quality score of a predicted structure generally characterizes a quality of the predicted structure. For example, the quality score of a predicted structure may characterize an estimated similarity between the predicted structure and an actual structure of the protein, a likelihood of the predicted structure based on the distances between the backbone atoms in the amino acids in the predicted structure, or both. Determining a quality score for a predicted structure is described further with reference to 806.

In response to determining that the search termination criterion is satisfied, the system determines a final predicted structure of the protein (706). To determine the final predicted structure of the protein, the system selects a predicted structure stored in the central memory. Generally, each predicted structure stored in the central memory is associated with a score, and the system determines the final predicted structure by selecting a predicted structure in the central memory based on the scores. For example, system may determine the final predicted structure to be a predicted structure stored in the central memory that has a highest score. The scores associated with the predicted structures stored in the central memory may be, for example, backbone-atom quality scores or full-atom quality scores (as described earlier).

In response to determining that the search termination criterion is not satisfied, the system determines whether a central memory update condition is satisfied by the current predicted structure (708). The system may determine that the central memory update condition is satisfied if, for example, a quality score of the current predicted structure is the highest quality score in the trajectory of predicted structures generated by the system up to the current iteration. In this example, the system dynamically updates the central memory to store the most "promising" predicted structures (e.g., which are most likely to accurately approximate the actual structure of the protein).

In response to determining that the central memory update condition is satisfied, the system updates the central memory (710). The central memory is a data store (e.g., a logical data storage area or a physical data storage device) which is configured to store predicted structures. The system can update the central memory by storing the current predicted structure in the central memory. Storing the current predicted structure in the central memory refers to storing the values of the structure parameters defining the current predicted structure in the central memory.

The system determines whether a local memory update condition is satisfied (712). For example, the system may determine the local memory update condition to be satisfied if the system has performed a predetermined number of iterations since the last time the system determined the local memory update condition to be satisfied. As another example, the system may determine the local memory update condition to be satisfied if an average increase in the quality score of the current predicted structure over a predetermined number of iterations is below a predetermined threshold.

In response to determining that the local memory update condition is satisfied, the system updates the local memory (714). In some implementations, the system updates the local memory by obtaining different structure fragments and replacing the structure fragments currently in the local memory with the different structure fragments. In some implementations, the system updates the local memory by obtaining different structure fragments and partially replacing the structure fragments currently in the local memory using a replacement policy. For example, the replacement policy may be a first-in-first-out (FIFO) replacement policy, where the structure fragments which were included in the local memory earliest are replaced by the different structure fragments.

The system may obtain structure fragments to be included in the local memory in a variety of different ways. For example, as will be described in more detail below, the system may produce structure fragments by: (i) fragmenting predicted structures stored in the central memory, (ii) fragmenting actual structures stored in a structure database of known structures of different proteins, (iii) generating the structure fragments using a generative neural network included in a fragment generation system, or (iv) a combination thereof.

In some implementations, the system obtains structure fragments to be included in the local memory by fragmenting predicted structures sampled from the central memory. The system may sample predicted structures from the central memory in accordance with scores associated with the predicted structures stored in the central memory. As described previously, each predicted structure stored in the central memory may be associated with a quality score (e.g., a backbone-atom quality score or full-atom quality score). As an example, to sample a predicted structure from the central memory, the system may determine a probability distribution over the predicted structures stored in the central memory using their associated scores (e.g., by processing the scores using a soft-max function). The system can then sample predicted structures from the central memory in accordance with the determined probability distribution.

In some implementations, the system obtains structure fragments to be included in the local memory by fragmenting actual structures of different proteins stored in a structure database. The actual structures of the different proteins stored in the structure database may have been determined using physical experimental methods such as x-ray crystallography.

In some implementations, the system obtains structure fragments to be included in the local memory using a generative neural network trained to generate realistic structure fragments. Generating structure fragments using a generative neural network is described further with reference to FIG. 4.

After updating the local memory, the system can return to 702 and repeat the preceding steps.

Figure 8:
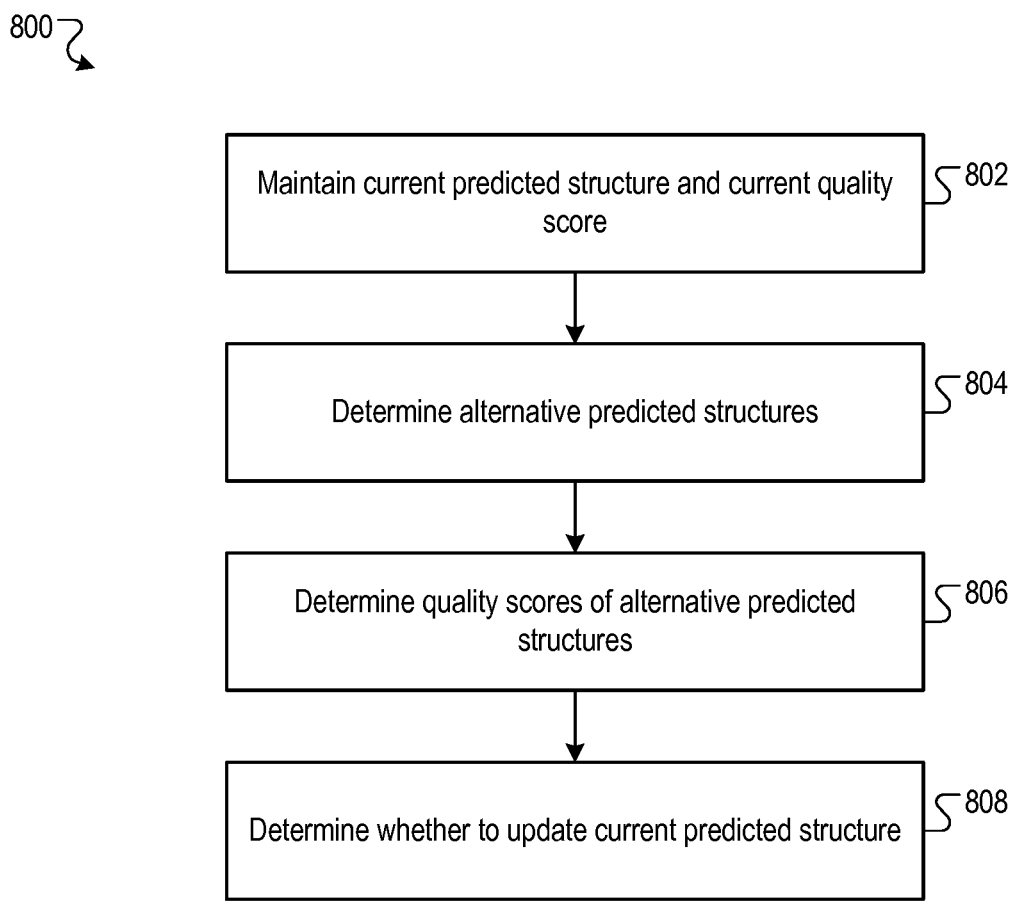
FIG. 8 is a flow diagram of an example process for determining whether to update a current predicted structure of a protein to an alternative predicted structure of the protein.

FIG. 8 is a flow diagram of an example process for determining whether to update a current predicted structure of a protein to an alternative predicted structure of the protein. For convenience, the process 800 will be described as being performed by a system of one or more computers located in one or more locations. For example, a search computing unit, e.g., the search computing units 108 and 110 of FIG. 1, appropriately programmed in accordance with this specification, can perform the process 800.

The system maintains a current predicted structure of the protein and a current quality score characterizing a quality of the current predicted structure (802). The current predicted folding structure is defined by values of a set of structure parameters. As an example, the structure parameters may be a sequence of torsion angles between backbone atoms in amino acids in the protein. The current quality score is a numerical value characterizing a quality of the current predicted structure.

The system determines alternative predicted structures of the protein (804). To determine an alternative predicted structure of the protein, the system obtains a structure fragment from the local memory. For example, the system may randomly sample a structure fragment from the local memory. After obtaining a structure fragment from the local memory, the system can generate an alternative predicted structure as a "perturbation" of the current predicted structure by the obtained structure fragment. More specifically, the system can determine the alternative predicted structure to include a portion of the current predicted structure and the obtained structure fragment.

The system determines a respective quality score for each alternative predicted structure (806). For example, the system may determine the quality score using one or more of: (i) a geometry score, (ii) a value score, (iii) a distance likelihood score, (iv) other additional scores.

For example, the system may determine the quality score as a linear combination of the geometry score, the value score, the likelihood score, and one or more additional scores, where the coefficients of the linear combination are adjustable system hyper-parameters.

The geometry score of a predicted structure of a protein is an estimate of a similarity measure (e.g., RMSD or GDT) between the predicted structure of the protein and the actual structure of the protein. To determine the geometry score of an alternative predicted folding structure, the system can process a network input characterizing the alternative predicted folding structure using a geometry neural network in accordance with current values of geometry neural network weights. The network input includes a representation of the amino acid sequence of the protein and the values of the folding structure parameters defining the alternative predicted folding structure. In some implementations, the geometry neural network is configured to directly output the geometry score. In some implementations, the geometry neural network is configured to generate an output defining a probability distribution over a predetermined set of geometry scores. In these implementations, the output of the geometry neural network includes a respective probability value for geometry score in the predetermined set of geometry scores. The system may determine the geometry score to be a measure of central tendency (e.g., a mean, median, or mode) of the probability distribution over the predetermined set of geometry scores.

The value score of a predicted structure of a protein is an estimate of a quality score characterizing a quality of a predicted structure generated (e.g., by a search computing unit) at a future search iteration (e.g., iteration of the process 700) if the current predicted structure (e.g., as maintained by the search computing unit) at the current search iteration is the predicted structure. To determine the value score of an alternative predicted folding structure, the system can process a network input characterizing the alternative predicted folding structure using a value neural network in accordance with current values of value neural network weights. In some implementations, the value neural network is configured to directly output the value score. In some implementations, the value neural network is configured to generate an output defining a probability distribution over a predetermined set of value scores. In these implementations, the output of the value network includes a respective probability value for each of a value score in the predetermined set of value scores. The system may determine the value score to be a measure of central tendency (e.g., a mean, median, or mode) of the probability distribution over the predetermined set of value scores.

The distance likelihood score of a predicted folding structure of a protein defines a likelihood of the predicted structure based on the difference between: (i) distances between pairs of amino acids in the predicted structure of the protein, and (ii) estimated distances between pairs of amino acids in the actual structure of the protein. To determine the distance likelihood score of an alternative predicted folding structure, the system can process a representation of the amino acid sequence, and (optionally) alignment features derived from a MSA corresponding to the protein, using a distance prediction system (as described with reference to FIG. 6).

The system may determine additional scores for the alternative predicted folding structure in addition to the geometry score, the value score, and the distance likelihood score. For example, the additional scores may include scores based on whether hydrophobic parts of the predicted structure would be exposed to water if the amino acid sequence were folded in accordance with the predicted structure.

The system determines whether to update the current predicted structure to an alternative predicted structure based on the respective quality scores of the current predicted structure and the alternative predicted structures (808).

In some implementations, the system may determine whether to update the current predicted structure to an alternative predicted structure using a deterministic procedure based on the quality scores. For example, the system may determine to update the current predicted structure to a particular alternative predicted structure if the particular alternative predicted structure has a higher quality score than the current predicted structure and any of the other alternative predicted structures. In this example, if the current predicted structure has a higher quality score than any of the alternative predicted structures, the system may determine not to update the current predicted structure to any of the alternative predicted structures.

In some implementations, the system may determine whether to update the current predicted structure to an alternative predicted structure using a stochastic procedure (i.e., that involves some randomness) based on the quality scores. For example, the system may determine a probability distribution over a set of structures including the current predicted structure and each of the alternative predicted structures using the quality scores. The system may determine to update the current predicted structure to a structure sampled from the set of structures including the current predicted structure and each of the alternative predicted structures using the probability distribution.

In a particular example, the system may determine the probability distribution by processing the respective quality scores of the current predicted structure and each of the alternative predicted structures using a soft-max function. In another particular example, the system may determine the probability distribution by processing the respective quality scores of the current predicted structure and each of the alternative predicted structures using a soft-max function in accordance with a temperature hyper-parameter. A probability distribution defined by discrete probability values $\{q_i\}_{i=1}^{n}$ can be determined by processing a set of scores $\{z_i\}_{i=1}^{n}$ using a soft-max function in accordance with a temperature hyper-parameter T based on the relationship:

$$q_i = \frac{\exp\left(\frac{z_i}{T}\right)}{\sum_{j=1}^{n} \exp\left(\frac{z_j}{T}\right)} \qquad (3)$$

In this example, a higher temperature parameter results in a more uniform score distribution, and therefore an increased likelihood that the system may update the current predicted structure to an alternative predicted structure with a lower quality score than the current predicted structure.

By determining whether to update the current predicted structure to an alternative predicted structure using a soft-max function in accordance with an elevated temperature hyper-parameter, the system can "explore" the space of possible protein structures. A search computing unit (e.g., as described with reference to FIG. 1) may alter the value of a temperature used to update its current predicted folding structure in accordance with a predetermined schedule. For example, the predetermined schedule may set the temperature value to an initial high value (resulting in initial exploration of the space of possible structures) which gradually decreases as the number of performed search iterations increases.

Figure 9:
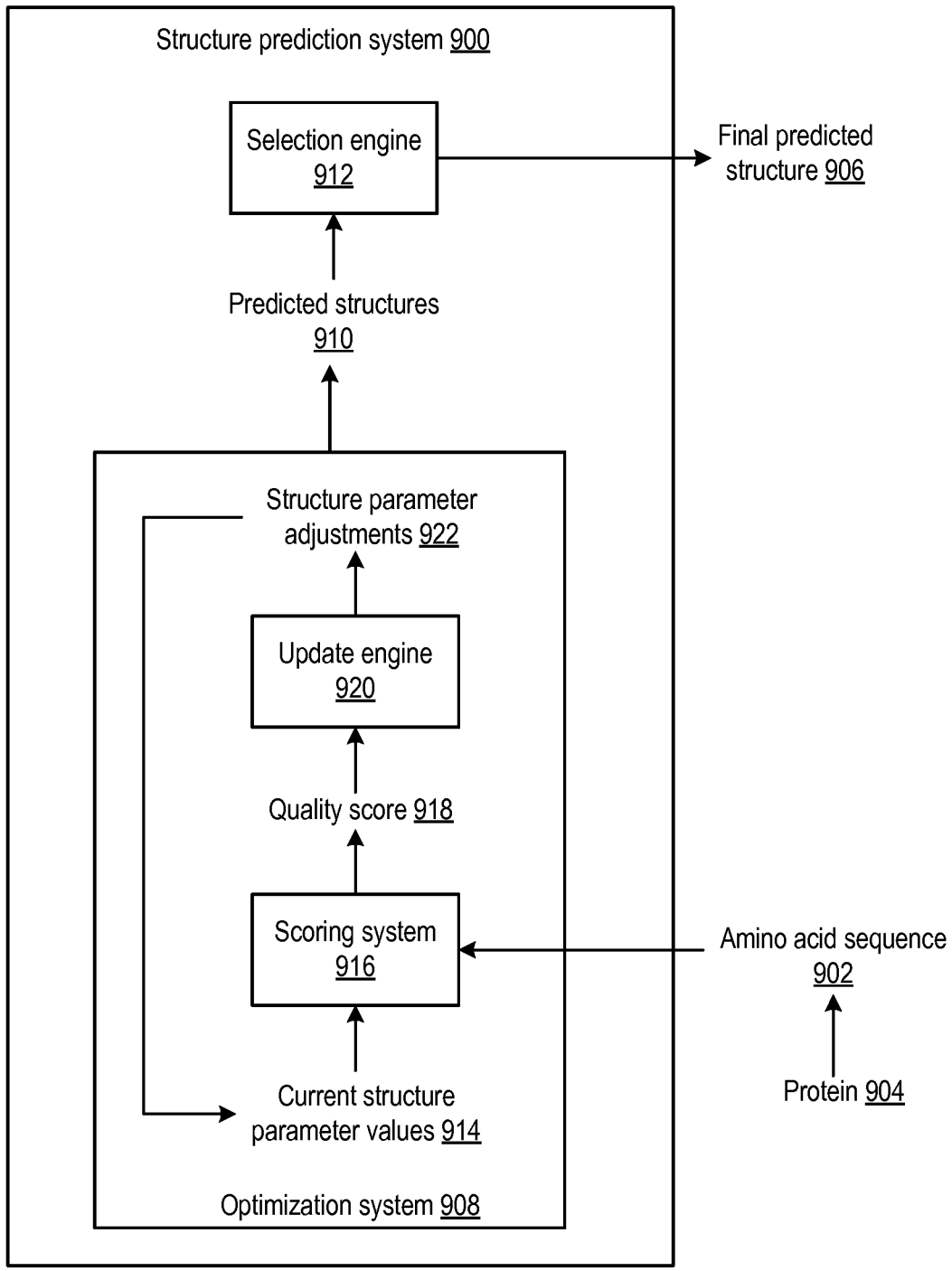
FIG. 9 is a block diagram of an example structure prediction system that uses an optimization system.

FIG. 9 is a block diagram of an example structure prediction system 900. The structure prediction system 900 is an example of a system implemented as computer programs on one or more computers in one or more locations in which the systems, components, and techniques described below are implemented.

The structure prediction system 900 is configured to process data defining an amino acid sequence 902 of a protein 904 to generate a final predicted structure 906 of the protein 904. Each amino acid in the amino acid sequence 902 is an organic compound which includes an amino functional group and a carboxyl functional group, as well as a side-chain (i.e., group of atoms) which is specific to the amino acid. The final predicted structure 906 defines an estimate of a three-dimensional configuration of the atoms in the amino acid sequence 902 of the protein 904 after the protein 904 undergoes protein folding. Protein folding refers to a physical process by which a sequence e.g. a random coil of amino acids (e.g., defined by the amino acid sequence 902 of the protein 904) folds into a unique three-dimensional configuration (e.g., as estimated by the final predicted structure 906).

The amino acid sequence 902 can be represented in any appropriate numerical format. For example, the amino acid sequence 902 may be represented as a sequence of one-hot vectors. In this example, each one-hot vector in the sequence of one-hot vectors represents a corresponding amino acid in the amino acid sequence 902. A one-hot vector has a different component for each possible amino acid (e.g., of a predetermined number of possible amino acids). A one-hot vector representing a particular amino acid has value one (or some other predetermined value) in the component corresponding to the particular amino acid and value zero (or some other predetermined value) in the other components.

A structure of the amino acid sequence 902 (e.g., the final predicted structure 906 output by the system 900) is defined by the values of a set of structure parameters. In some implementations, the structure parameters are a sequence of three-dimensional (3D) numerical coordinates (e.g., represented as 3D vectors) where each coordinate represents the position (in some given frame of reference) of a corresponding atom in an amino acid from the amino acid sequence 902. For example, the structure parameters may be a sequence of 3D numerical coordinates representing the respective positions of the alpha carbon atoms in the amino acids in the structure. An alpha carbon atom, which is referred to in this specification as a backbone atom, refers to a carbon atom in an amino acid to which the amino functional group, the carboxyl functional group, and the side-chain are bonded. In some implementations, the structure parameters are a sequence of torsion (i.e., dihedral) angles between specific atoms in the amino acids in the structure. For example, the structure parameters may be a sequence of phi ($\phi$), psi ($\psi$), and optionally omega ($\omega$) dihedral angles between the backbone atoms in amino acids in the structure.

To generate the final predicted structure 906, the system 900 uses an optimization system 908 to generate multiple predicted structures 910 of the protein 904, each of which are candidates to be the final predicted structure 906 of the protein 904. After generating the multiple predicted structures 910, the system 900 uses a selection engine 912 to select one of the predicted structures 910 as the final predicted structure 906 (as will be described in more detail below).

To generate a predicted structure 910, the optimization system 908 first obtains initial values of the set of structure parameters which define the structure of the protein 904. Generally, the optimization system 908 determines the initial values of the set of structure parameters using a process that involves some randomness, thereby enabling the optimization system 908 to "explore" the space of possible predicted structures. In a particular example, if the optimization system 908 has previously generated one or more predicted structures 910 for the protein, to determine the initial values of the structure parameters, the optimization system 908 may obtain the values of structure parameters defining a previously generated predicted structure 910 for the protein. Subsequently, the optimization system 908 may determine the initial values of the structure parameters by perturbing the values of the structure parameters defining the previously generated predicted structure using random noise values (as will be described in more detail with reference to FIG. 11).

Having determined the initial values of the structure parameters, the optimization system 908 iteratively updates (i.e., adjusts) the values of structure parameters over multiple update iterations. When the optimization system 908 determines that a termination criterion is satisfied, the optimization system 908 outputs a predicted structure 910 that is defined by the current values of the structure parameters after the final update iteration.

The optimization system 908 is configured to update the values of the structure parameters over the multiple update iterations to generate a predicted structure with a high quality score. As will be described in more detail below, the quality score of a predicted structure characterizes a quality of the predicted structure, for example, how closely the predicted structure conforms to the actual structure of the protein 904. For convenience, in this specification a higher quality score will be understood to characterize a higher quality of a predicted structure.

At each update iteration, the optimization system 908 processes the current structure parameter values 914 and a representation of the amino acid sequence 902 using a scoring system 916 to generate a quality score 918 characterizing the quality of the predicted structure defined by the current structure parameter values 914. As will be described in more detail with reference to FIG. 10, the scoring system 916 can determine the quality score 918 based on one or more of: (i) a structure parameter likelihood score, (ii) a geometry score, (iii) a distance likelihood score, or (iv) one or more additional scores.

The scoring system 916 can determine the structure parameter likelihood score by determining a respective probability distribution over the possible values for each structure parameter, and determining the likelihood of the current structure parameter values 914 according to these probability distributions. The scoring system 916 can determine the geometry score by generating an estimate of a similarity measure between the predicted structure defined by the current structure parameter values 914 and the actual structure of the protein 904. The scoring system 196 can determine the distance likelihood score by determining a respective probability distribution over possible distances ranges between each pair of amino acids in the amino acid sequence 102, and determining the likelihood of the predicted structure defined by the current structure parameter values according to these probability distributions. The scoring system 916 can determine additional scores based on how closely the predicted structure defined by the current structure parameter values 914 conforms to biochemical constraints on real-world protein structures. As used throughout this specification, the term "likelihood" (e.g., as in structure parameter likelihood score and distance likelihood score) can refer to any numerical value derived from a probability distribution.

After determining the quality score 918 for the predicted structure defined by the current structure parameter values 914, the optimization system 908 uses an update engine 920 to determine structure parameter adjustments 922 which the optimization system 908 subsequently uses to adjust the current structure parameter values 914. For example, the structure parameter adjustments 922 may include a respective numerical value corresponding to each structure parameter. In this example, the optimization system 908 may adjust the current structure parameter values 914 by adding the corresponding structure parameter adjustment value 922 to each current structure parameter value 914.

As will be described further with reference to FIG. 11, the update engine 920 is configured to determine the structure parameter adjustments 922 by determining a respective gradient of the quality score 918 with respect to each current structure parameter value 914. The update engine 920 uses the gradients of the quality score 918 with respect to the current structure parameter values 914 to determine the structure parameter adjustments 922. The gradients of the quality score 918 with respect to the current structure parameter values 914 indicate a "direction" in which the current structure parameter values 914 can be adjusted to incrementally improve the quality score 918 of the predicted structure defined by the resulting structure parameter values.

Generally, each of the predicted structures 910 generated by the optimization system 908 are different from one another. In particular, the structure parameter values defining each of the predicted structures 910 generated by the optimization system 908 are different since they are derived from different (e.g., randomly determined) initial structure parameter values. The selection engine 912 may be configured to select the predicted structure 910 with the highest corresponding quality score 918 as the final predicted structure 906. In this manner, the system 900 outputs the "best" of the predicted structures 910 generated by the optimization system 908.

Generally, the optimization system 908 can jointly optimize the predicted structure of an entire protein without relying on domain segmentation.

Figure 10:
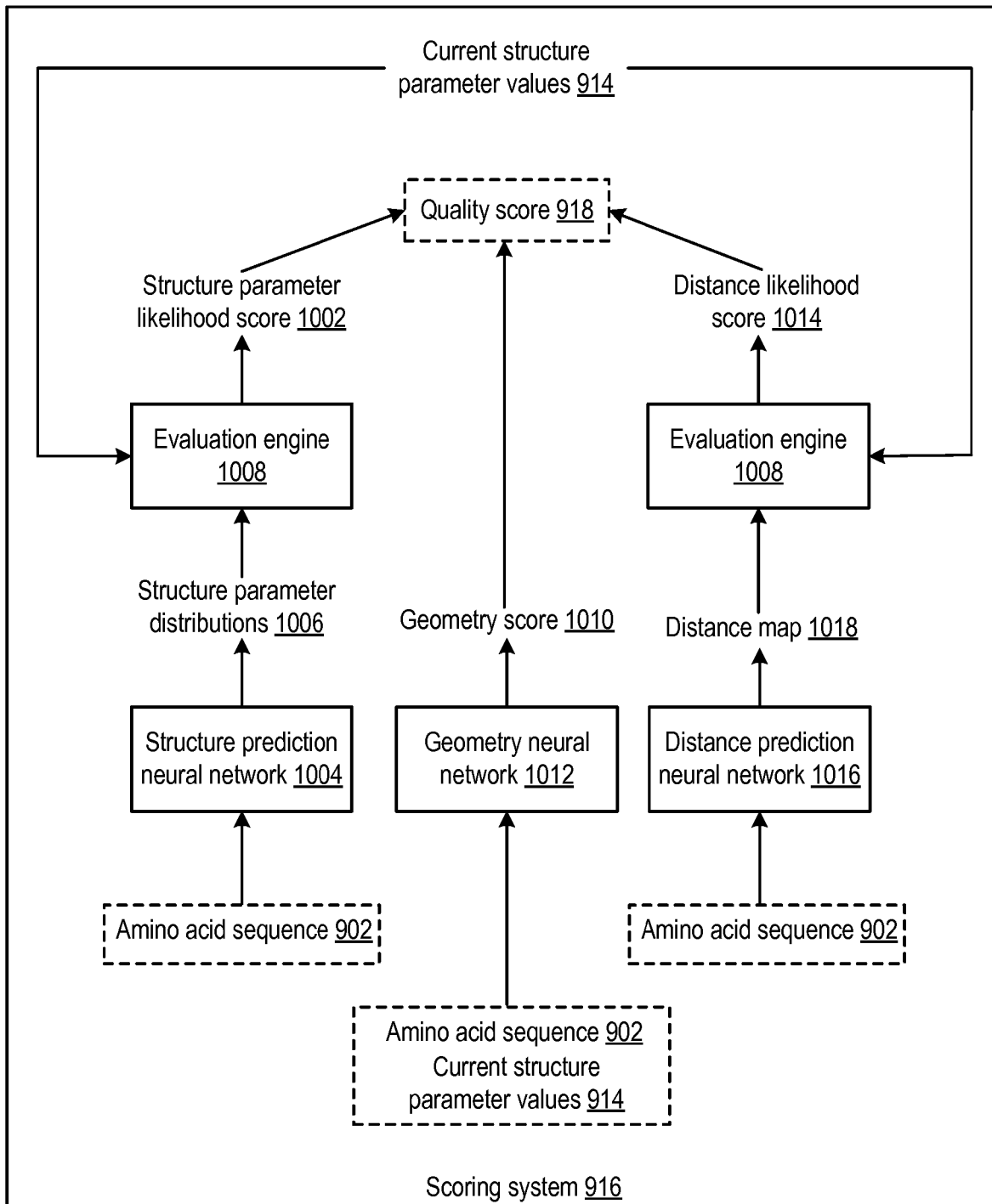
FIG. 10 is a block diagram of an example scoring system, e.g., that can be used by the structure prediction system described with reference to FIG. 9.

FIG. 10 is a block diagram of an example scoring system 916. The scoring system 916 is an example of a system implemented as computer programs on one or more computers in one or more locations in which the systems, components, and techniques described below are implemented. The scoring system 916 can be understood as an alternative implementation of the scoring system 136 that is described with reference to FIG. 5. Generally, a scoring system can include any combination of any of the components of the scoring systems described with reference to FIG. 5 and FIG. 10.

The scoring system 916 is configured to process a representation of the amino acid sequence 902 of the protein 904 and the current structure parameter values 914 at each update iteration of the optimization system 908 to generate a quality score 918. The quality score 918 is a numerical value which characterizes the quality of the predicted structure of the protein 904 defined by the current structure parameter values 914. The scoring system 916 generates one or more of: (i) a structure parameter likelihood score, (ii) a geometry score, (iii) a distance likelihood score, or (iv) one or more additional scores, and thereafter combines them (e.g., as a weighted linear combination) to generate the quality score 918.

To generate the structure parameter likelihood score 1002, the scoring system 916 can process an input including a representation of the amino acid sequence 902 using a structure prediction neural network 1004. As described earlier, the representation of the amino acid sequence 902 may be a sequence of one-hot vectors representing each amino acid in the amino acid sequence 902. In addition to the representation of the amino acid sequence 902, the structure prediction neural network 1004 may be configured to process additional inputs including, for example, data derived from a multiple sequence alignment (MSA) of amino acid sequences from other proteins with the amino acid sequence 902. A MSA refers to a correspondence between amino acids in amino acid sequences from multiple other proteins with the amino acids in the amino acid sequence 902. A MSA can be generated by processing the amino acid sequences of other proteins (e.g., which are stored in a database) using any appropriate computational sequence alignment technique (e.g., progressive alignment construction). The additional inputs to the structure prediction neural network 1004 derived from the MSA may include a representation of the MSA itself, statistical features (e.g., second order statistical features) derived from the MSA such as those described with reference to: S. Seemayer, M. Gruber, and J. Soding: "CCMpred: fast and precise prediction of protein residue-residue contacts from correlated mutations", Bioinformatics, 2014, or both.

The structure prediction neural network 1004 is configured to process the structure prediction neural network input in accordance with values of structure prediction neural network weights to generate an output defining, for each structure parameter, a respective probability distribution over possible values of the structure parameter. The probability distributions over the possible values of each of the structure parameters will be referred to in this specification (and identified in the figures) as the structure parameter distributions 1006. For example, if the structure parameters are a set of torsion angles between backbone atoms of the amino acid sequence 902, then for each torsion angle, the structure prediction neural network 1004 may generate a respective probability for each of a set of possible angle ranges. In a particular example, the structure prediction neural network 1004 may generate a respective probability for each of the angle ranges:

$$\left[0, \frac{\pi}{3}\right), \left[\frac{\pi}{3}, \frac{2\pi}{3}\right), \left[\frac{2\pi}{3}, \pi\right), \left[\pi, \frac{4\pi}{3}\right), \left[\frac{4\pi}{3}, \frac{5\pi}{3}\right), \left[\frac{5\pi}{3}, 2\pi\right).$$

In another particular example, the structure prediction neural network 1004 may generate data defining a respective joint probability distribution over the set of possible values of the structure parameters (e.g., torsion angles) for each amino acid of the amino acid sequence 902. In another particular example, the structure prediction neural network 1004 may generate values of the parameters of a parametric probability distribution (e.g., von Mises probability distribution) over possible values of the structure parameters (e.g., torsion angles).

To determine the structure parameter likelihood score 1002 from the structure parameter distributions 1006, an evaluation engine 1008 determines the probability of each current structure parameter value 914 using the corresponding probability distribution over possible values for the structure parameter generated by the structure prediction neural network 1004. The evaluation engine 1008 may thereafter determine the structure parameter likelihood score 1002 based on the respective probability of each current structure parameter value, for example, based on the quantity expressed by:

$$\prod_i p_i^{sp}(\tau_i) \qquad (4)$$

where the product is over each structure parameter i, and $p_i^{sp}(\tau_i)$ denotes the probability of the current structure parameter value $\tau_i$ according to the probability distribution $p_i^{sp}(\cdot)$ over possible values of the structure parameter generated by the structure prediction neural network 1004. In particular examples, the evaluation engine 1008 may determine the structure parameter likelihood score 1002 to be the quantity expressed by equation (4), or to be a function (e.g., the logarithm) of the quantity expressed by equation (4).

In some cases, for example (as described above) when the structure parameter distributions 1006 are discrete probability distributions over ranges of possible structure parameter values, a structure parameter likelihood score 1002 determined with reference to the structure parameter distributions 1006 may not be differentiable. To cause the structure parameter likelihood score 1002 to be differentiable (i.e., with respect to the current structure parameter values 914), the evaluation engine 1008 may fit a differentiable function to each of the structure parameter distributions 1006. Subsequently, the evaluation engine 1008 may determine the structure parameter likelihood score 1002 with reference to the differentiable function fitted to each structure parameter distribution 1006. Fitting a differentiable function to a given structure parameter distribution 1006 refers to determining the values of the parameters defining the differentiable function which cause the differentiable function to match the given structure parameter distribution 1006 as closely as possible. The evaluation engine 1008 can use any appropriate method to fit the differentiable functions to the structure parameter distributions, for example, the method of moments or the maximum likelihood method.

In some cases, the evaluation engine 1008 may fit a respective parametric probability distribution (with a differentiable probability density function) to each of the structure parameter distributions 1006 generated by the structure prediction neural network 1004. For example, the parametric probability distribution may be a uni-modal von Mises probability distribution with distribution parameters μ and κ. In some other cases, the evaluation engine 1008 may fit a respective spline (e.g., a cubic spline) to each of the structure parameter distributions 1006 generated by the structure prediction neural network 1004. Even when the structure parameter distributions initially generated by the structure prediction neural network 1004 are non-convex (e.g., multi-modal), the differentiable functions fitted to the structure parameter distributions by the evaluation engine 1008 may be convex functions (e.g., uni-modal von Mises probability distributions). Determining the structure parameter likelihood score 1002 with reference to convex differentiable functions fitted to the structure parameter distributions 1006 facilitates performing gradient descent on the quality score 918, as described further with reference to FIG. 11.

To generate the geometry score 1010, the scoring system 916 can process an input including a representation of the amino acid sequence 902 and the current structure parameter values 914 using a geometry neural network 1012. The geometry neural network may process additional inputs, such as data derived from a MSA of amino acid sequences from other proteins with the amino acid sequence 902 (as described earlier). The geometry neural network 1012 is configured to process the geometry neural network input in accordance with values of geometry neural network weights to generate the geometry score 1010. The geometry score 1010 is an estimate of a similarity measure between the predicted structure defined by the current structure parameter values 914 and the actual structure of the protein 904. For example, the similarity measure may be a root-mean-square-deviation (RMSD) between the current structure parameter values 914 and structure parameters values defining the actual structure of the protein 904. As another example, the similarity measure may be a global distance test (GDT) similarity measure. The GDT similarity can be defined as the fraction of backbone atoms in the amino acids in the amino acid sequence 902 whose position in the predicted structure defined by the current structure parameter values 914 is within a predetermined distance of their position in the actual structure of the protein 904.

To generate the distance likelihood score 1014, the scoring system 916 can process an input including a representation of the amino acid sequence 902 using a distance prediction neural network 1016. The distance prediction neural network 1016 may process additional inputs, such as data derived from a MSA of amino acid sequences from other proteins with the amino acid sequence 902 (as described earlier). The distance prediction neural network 1016 is configured to process the distance prediction neural network input in accordance with current values of distance prediction neural network weights to generate a distance map 1018. The distance map 1018 defines, for each pair of amino acids in the amino acid sequence 902 (i.e., each set of two different amino acids from the amino acid sequence 902), a respective probability distribution over possible distance ranges between the pair of amino acids. The distance between a first amino acid and a second amino acid in the amino acid sequence 902 refers to a physical distance (e.g., measured in angstroms) between a particular atom (e.g., a backbone atom such as an alpha carbon atom; or a beta carbon atom) in the first amino acid and a particular atom in the second amino acid. In a particular example, for each pair of amino acids in the amino acid sequence 902, the distance map 1018 may include respective probabilities that the pair of amino acids are separated by the distances ranges: [0, 2 A), [2 A, 4 A), [4 A, 6 A), [6 A, ∞), where A denotes Angstroms. In another example 64 distance ranges are used, as previously described. In some implementations the distance prediction neural network 1016 may be used to generate distance map subsets or crops, e.g. as previously described, which may then be combined to obtain the distance map 1018. Thus the distance prediction system 528 may be used in the structure prediction system 900 to generate the distance map 1018.

The evaluation engine 1008 uses the distance map 1018 to determine the respective probabilities that each pair of amino acids in the amino acid sequence 902 are separated by the respective distance $d_{i,j}$ defined by the current structure parameter values. When the structure parameters are a sequence of numerical coordinates where each coordinate represents the position of a corresponding backbone atom in an amino acid in the amino acid sequence 902, then the current structure parameter values 914 directly define the distance between each pair of amino acids. For example, the distance between a pair of amino acids may be defined by the Euclidean distance between the corresponding numerical coordinates representing the positions of respective atoms in each of the amino acids in the pair of amino acids, e.g. the beta carbon atoms of the pair of amino acids. When the structure parameters are a sequence of torsion angles between respective atoms in each amino acid in the amino acid sequence 902, then the current structure parameter values 914 indirectly define the position of, and therefore the distance between, each pair of amino acids in the amino acid sequence 902 (as previously described).

The evaluation engine 1008 uses the respective probabilities that each pair of amino acids in the amino acid sequence 902 are separated by the respective distance defined by the current structure parameter values 914 to generate the distance likelihood score 1014. For example, the evaluation engine 1008 may generate the distance likelihood score 1014 based on the quantity expressed by:

$$\prod_{(i,j), i \neq j} p_{i,j}^{dl}(d_{i,j}) \tag{5}$$

where the product is over pairs of amino acids in the amino acid sequence 902 indexed by (i,j) and $p_{i,j}^{dl}(d_{i,j})$ denotes the probability that the amino acid pair indexed by (i,j) are separated by the distance $d_{i,j}$ defined by the current structure parameter values 914 according to the corresponding probability distribution $p_{i,j}^{dl}$ over possible distance ranges between the pair of amino acid residues (i,j) defined by distance map 1018. In particular examples, the evaluation engine 1008 may determine the distance likelihood score 1014 to be the quantity expressed by equation (5), or to be a function (e.g., the negative logarithm) of the quantity expressed by equation (5) (e.g. a negative log probability).

In some cases, the evaluation engine 1008 may additionally determine the distance likelihood score 1014 using a "reference" distance map. A reference distance map characterizes estimated distances which are generally expected between each pair of amino acids in the amino acid sequence 902, but which are determined without reference to the identities of the specific amino acids in the amino acid sequence 902. For example, for each pair of amino acids in the amino acid sequence 902, the reference distance map may characterize the estimated distance between the pair of amino acids based on the positions and relative offsets of the amino acids in the amino acid pair. The position of a given amino acid refers to the number of other amino acids between the given amino acid and the first amino acid in the amino acid sequence. The relative offset between two amino acids refers to the number of other amino acids between the two amino acids in the amino acid sequence. Similar to the distance map 1018, the reference distance map characterizes the estimated distance between each pairs of amino acids in the amino acid sequence 902 by a respective probability distribution over a set of possible distance ranges.

The scoring system 916 may generate the reference distance map using a protein structure database of actual structures of different proteins. In a particular example, the scoring system 916 may determine a reference probability distribution over a set of possible distance ranges between a pair of amino acids based on each pair of amino acids included in a respective protein structure in the protein structure database with the same positions and relative offset. In another particular example, the scoring system 916 can determine a reference probability distribution based on an output of a separate distance prediction neural network (or distance prediction system 528) that is configured to process an input that characterizes the length of the amino acid sequence of the protein (but does not include, e.g., alignment features or features identifying the amino acids). Such a separate distance prediction neural network may be trained using the same training data set used to train the distance prediction neural network 616 or 1016 (but with an input feature indicating whether or not the amino acid is glycine, which lacks a beta carbon, to account for the atoms between which distances are predicted).

The evaluation engine 1008 can use the respective probability, according to the reference distance map, that each pair of amino acids in the amino acid sequence 902 are separated by the respective distance defined by the current structure parameter values 914 to generate the distance likelihood score 1014. For example, the evaluation engine 1008 may generate the distance likelihood score 1014 based on the quantity expressed by:

$$\prod_{(i,j),i\neq j} p_{i,j}^{dl,r}(d_{i,j}) \quad (6)$$

where the product is over pairs of amino acids in the amino acid sequence 902 indexed by (i,j) and $p_{i,j}^{dl,r}(d_{i,j})$ denotes a probability that the amino acid pair indexed by (i,j) are separated by the distance $d_{i,j}$ defined by the current structure parameter values 914 according to a corresponding probability distribution $p_{i,j}^{dl,r}(\cdot)$ over possible distance ranges between the pair of amino acid residues (i,j) defined by reference distance map. In a particular example, the evaluation engine 1008 may determine the distance likelihood score 1014 to be the quantity expressed by:

$$-\log \prod_{(i,j),i\neq j} p_{i,j}^{dl}(d_{i,j}) + \log \prod_{(i,j),i\neq j} p_{i,j}^{dl,r}(d_{i,j}) \quad (7)$$

where the variables in equation (7) have the same definitions as in equations (5) and (6).

In some cases, for example when the distance map 1018 and reference distance map define discrete probability distributions over ranges of possible distance ranges between pairs of amino acids, a distance likelihood score 1014 determined with reference to the distance map 1018 and the reference distance map may not be differentiable. To cause the distance likelihood score 1014 to be differentiable (i.e., with respect to the current structure parameter values 914), the evaluation engine 1008 may fit a differentiable function to each of the probability distributions defined by the distance map 1018 and the reference distance map. Subsequently, the evaluation engine 1008 may determine the distance likelihood score 1014 with reference to the differentiable function fitted to each of the probability distributions defined by the distance map 1018 and the reference distance map. As described above with reference to the structure parameter distributions 1006, the evaluation engine 1008 may fit respective parametric probability distributions (e.g., uni-modal von Mises probability distributions) or splines to each of the probability distributions defined by the distance map 1018 and the reference distance map. For example, the evaluation engine 1008 may interpolate the discrete probabilities e.g. negative log probabilities with a spline such as a cubic spline; this may be referred to as a distance potential. In some implementations the distance potential may have a constant extrapolation above a threshold distance e.g. 18 Å, as greater distances are harder to predict accurately.

As previously mentioned, the scoring system 916 can determine the distance map 1016 as described with reference to FIG. 6, by generating a set of distance map crops that are proper subsets of the entire distance map 1016, and then fusing the distance map crops (e.g., by averaging the overlapping distance map crops).

The scoring system 916 can determine the quality score 918 based on one or more additional scores, for example, a physics or physical constraint score. The physics score may characterize the likelihood of the current structure parameter values 914 based on how closely the predicted structure defined by the current structure parameter values 914 conforms to biochemical constraints on real-world protein structures. For example, the scoring system 916 may determine the physics score based on a van der Waals potential which characterizes the interatomic potential energy associated with predicted structures; this term can help to inhibit steric clashes. In this example, the scoring system 916 may determine the physics score to be:

$$\sum_i \sum_{j>i} \frac{(r_{ij}^2 - d_{ij}^2)^2}{r_{ij}} \quad (8)$$

where i and j index the amino acids in the amino acid sequence 902, $r_{ij}$ represents the summed van der Waal radii for amino acid i and amino acid j, and $d_{ij}$ represents the interatomic distance between amino acid i and amino acid j.

As previously mentioned, the distance likelihood score 1014, e.g. as expressed in equation (7), may be considered as a distance-based potential to be minimized e.g. by gradient descent. This may be combined, e g summed, with a potential based on the structure parameter likelihood score e.g. a sum of negative log likelihoods of a torsion angle for each residue according to the von Mises probability distributions ($-\Sigma_i \log p(\phi_i, \psi_i)$) and/or with a potential based on the physics score of equation (8). As (7) and (8) are functions of $d_{ij}$ rather than ($\phi, \psi$), when performing gradient descent to optimize ($\phi, \psi$), $d_{ij}$ can be related to ($\phi, \psi$) by a differentiable model of protein geometry $x=G(\phi, \psi)$ where x denotes atomic e.g. beta carbon coordinates and $d_{ij}\|x_i-x_j\|$. Thus the distance likelihood score 1014 ("distance-based potential") may be expressed as a function of ($\phi, \psi$) to facilitate optimizing these torsion angles by a gradient descent algorithm.

Generally the structure prediction neural network 1004, the geometry neural network 1012, and the distance prediction neural network 1016 can be implemented in any appropriate neural network configuration. For example, the structure prediction neural network 1004, the geometry neural network 1012, and the distance prediction neural network 1016 may include multiple convolutional neural network layers, attention layers, and residual blocks. In some cases, the convolutional layers may include dilated convolutional filters to increase the sizes of their respective receptive fields. In some implementations, the structure prediction neural network 1004 may have an autoregressive architecture (e.g., derived from a WaveNet neural network architecture, ibid) which sequentially generates each structure parameter distribution conditioned on the structure parameter values of preceding structure parameters. In some implementations, the structure prediction neural network 1004 may have an architecture derived from a variational autoencoder (e.g., derived from a DRAW neural network architecture, ibid) which generates the structure parameter distributions by processing randomly sampled latent variables at each of multiple internal time steps.

In some cases, one or more of the scoring neural networks may share weight values. Neural networks are said to share a weight value if the weight value is the same in each of the neural networks and changing the weight value in any of the neural networks (e.g., during training) causes the weight value to change in all the neural networks. For example, the structure prediction neural network 1004 and the distance prediction neural network 1016 may share the same weight values in one or more neural network layers.

The structure prediction neural network 1004, the geometry neural network 1012, and the distance prediction neural network 1016 can be trained using machine learning training techniques (e.g., stochastic gradient descent) on respective sets of training data (as will be described in more detail below).

The structure prediction neural network 1004 can be trained based on a set of training data which includes multiple training examples. Each training example may include: (i) a training network input derived from a training protein with a known structure, and (ii) target structure parameter values defining the known structure of the training protein. The training network input includes a representation of the amino acid sequence of the training protein, and optionally, data derived from a MSA of amino acid sequences from other proteins with the amino acid sequence 902. The target structure parameter values represent parameter values which should be assigned a high probability by the structure parameter distributions 1006 generated by the structure prediction neural network 1004 by processing the training network input. The structure of the training protein may have been derived through experimental methods (e.g., x-ray crystallography).

The geometry neural network 1012 can be trained based on a set of training data which includes multiple training examples. Each training example may include: (i) a training network input derived from a training protein with a known structure, (ii) a training predicted structure of the protein, and (ii) a target geometry score that is a similarity measure between the training predicted structure of the protein and the actual structure of the protein. The training network input includes a representation of the amino acid sequence of the training protein, structure parameter values defining the structure of the training protein, and optionally, data derived from a MSA of amino acid sequences from other proteins with the amino acid sequence 902. The target geometry score for the training predicted structure represents the geometry score that should be generated by the geometry neural network 1012 by processing the training network input. The structure of the training protein may have been derived through experimental methods (e.g., x-ray crystallography).

In some cases, the geometry neural network 1012 may be trained using a contrastive divergence training procedure. In this case, the geometry score generated by the geometry neural network may not be a direct estimate of a particular similarity measure between the predicted structure and the actual structure of the protein. The description of the geometry neural network 1012 in this specification should be understood to include the case where the geometry neural network is trained using a contrastive divergence training procedure.

The distance prediction neural network 1016 can be trained based on a training data set including multiple training examples. Each training example may include: (i) a training network input derived from a training protein with a known structure, and (ii) a target distance map which defines respective distances between each pair of amino acids in the amino acid sequence of the training protein. The training network input includes a representation of the amino acid sequence of the training protein, and optionally, data derived from a MSA of amino acid sequences from other proteins with the amino acid sequence 902. The target distance map represents distances between amino acid pairs which should be assigned a high probability by the probability distributions of the distance map 1018 generated by the distance prediction neural network 1016 by processing the training network input.

Figure 11:
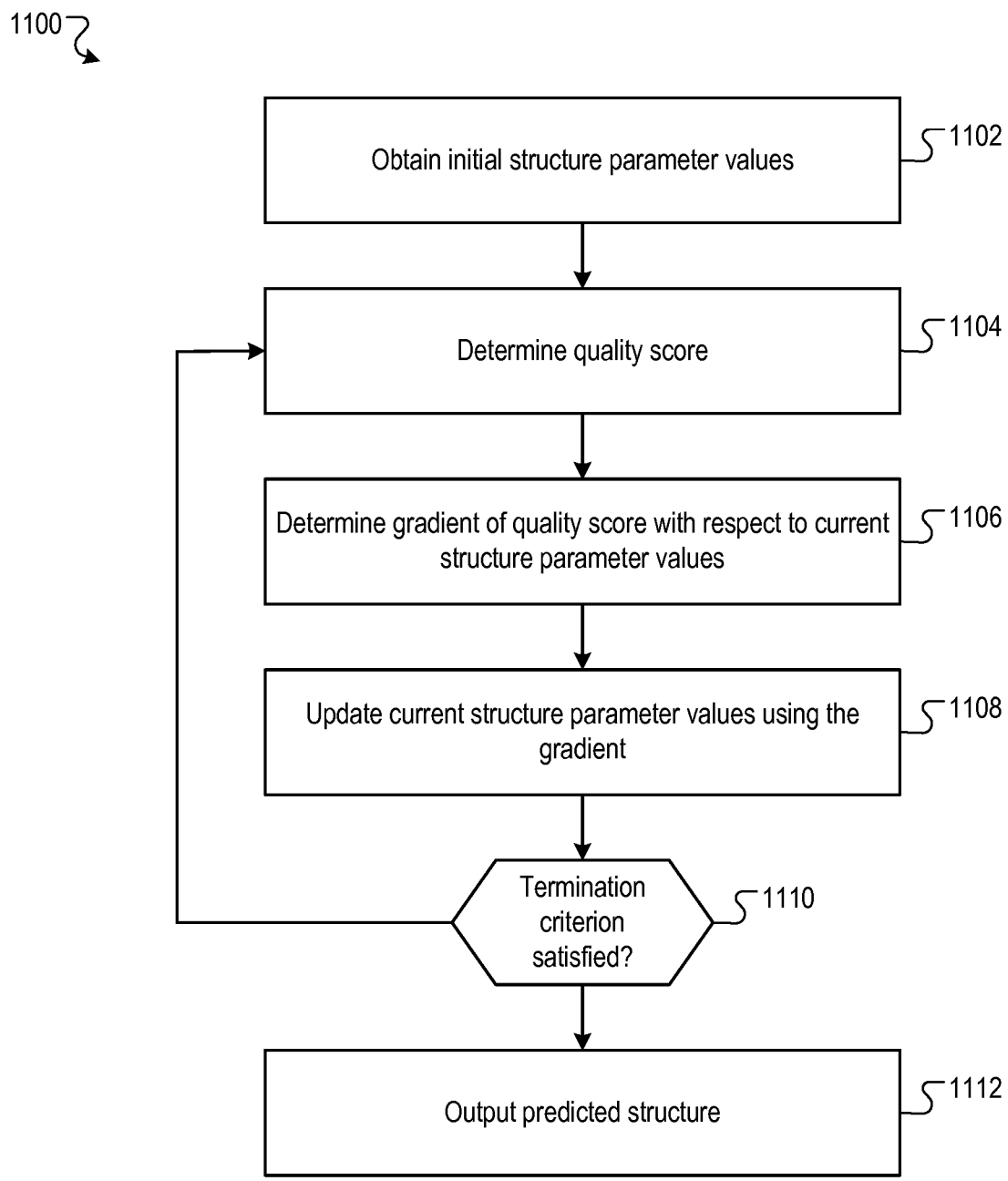
FIG. 11 is a flow diagram of an example process for determining a predicted structure of a protein.

FIG. 11 is a flow diagram of an example process 1100 for determining a predicted structure of a protein. For convenience, the process 1100 will be described as being performed by a system of one or more computers located in one or more locations. For example, an optimization system, e.g., the optimization system 908 of FIG. 9, appropriately programmed in accordance with this specification, can perform the process 1100. In particular, the optimization system 908 can perform the process 1100 multiple times to determine multiple predicted structures of the protein.

The system determines a respective initial value for each of the structure parameters defining the structure of the protein (1102). Generally, the system determines the initial values of the structure parameters using a process that involves some randomness, as will be described in more detail below.

In some implementations, to determine the initial values of the structure parameters, the system obtains the structure parameter values defining a predicted structure of the protein which was previously generated by system (e.g., by performing the process 1100). The system then determines the initial values of the structure parameters by perturbing the obtained values of the structure parameters defining the previously generated predicted structure using random noise values. For example, the system may generate the random noise values by sampling from a predetermined probability distribution (e.g., a zero mean Gaussian distribution), and determine the initial values of the structure parameters by adding the generated random noise values to the structure parameter values defining the previously generated predicted structure.

In some implementations, to determine the initial values of the structure parameters, the system obtains the structures parameter values defining multiple predicted structures of the protein which were previously generated by the system. The system then determines the initial values of the structure parameters by combining the structure parameter values defining each of the previously predicted structures of the protein. For example, the system may determine the initial values of the structure parameters by averaging the structure parameter values defining each of the previously predicted structures of the protein. As another example, the system may determine the initial values of the structure parameters by extraction disjoint portions of the structure parameter values defining each of the previously predicted structures of the protein.

In some implementations, to determine the initial values of the structure parameters, the system, the system processes an input including a representation of the amino acid sequence of the protein using a structure prediction neural network. As described with reference to FIG. 10, the structure prediction neural network is configured to process the input to generate an output defining, for each structure parameter, a respective probability distribution over possible values of the structure parameter. The system then determines the initial value of each structure parameter by sampling a value from the corresponding probability distribution over possible values of the structure parameter. For example, if the structure parameters are a set of torsion angles between backbone atoms of the amino acid sequence, then for each torsion angle, the structure prediction neural network may generate a respective probability over a set of possible angle ranges. In this example, for each structure parameter, the system may sample an angle range in accordance with the probability distribution corresponding to the structure parameter, and determine the initial value of the structure parameter to be a particular torsion angle randomly selected from the sampled angle range.

The system determines a quality score characterizing the quality of the predicted structure of the protein defined by the current structure parameter values (1104). For the first iteration of the process 1100, the current structure parameter values are the initial structure parameter values (i.e., as described with reference to 1102). As described in more detail with reference to FIG. 10, the system determines the quality score for the predicted structure defined by the current structure parameter values based on respective outputs of one or more scoring neural networks. Each of the scoring neural networks are configured to process: (i) the current values of the structure parameters, (ii) a representation of the amino acid sequence of the protein, or (iii) both. The scoring neural networks may include one or more of: a structure prediction neural network, a geometry neural network, and a distance prediction neural network.

In general, some of the scoring neural networks (e.g., the structure prediction neural network and the distance prediction neural network) may be configured to process inputs which do not include the current structure parameter values. The system can process the inputs provided to these scoring neural networks once (i.e., prior to the first iteration of the process 1100). Thereafter, at each iteration of the process 1100, the system can use the respective outputs generated by these scoring neural networks to determine the quality score without re-processing their respective inputs. For those scoring neural networks (e.g., the geometry neural network) which process an input which includes the current structure parameter values, the system must process their respective inputs at each iteration of the process 1100 in order to determine the quality score for the iteration.

The system determines a respective gradient of the quality score with respect to each current structure parameter value (1106). To determine the gradient of the quality score with respect to a current structure parameter value, the system can determine the gradient of each of the individual scores used to determine the quality score with respect to the current structure parameter value. The individual scores used to determine the quality score can include one or more of: the structure parameter likelihood score, the geometry score, the distance likelihood score, and the physics score. Since the quality score is a function (e.g., a weighted linear combination) of the individual scores, the gradient of the quality score with respect to a current structure parameter value can be determined from the gradient of each of the individual scores with respect to the current structure parameter. For example, if the quality score is given by:

$$QS = \alpha_1 \cdot SPLS + \alpha_2 \cdot GS + \alpha_3 \cdot DLS \quad (9)$$

where QS is the quality score, SPLS is the structure parameter likelihood score, GS is the geometry score, DLS is the distance likelihood score, and $\{\alpha_i\}_{i=1}^3$ are constant values, then the gradient of the quality score with respect to the current structure parameter value r is given by:

$$\nabla_r QS = \alpha_1 \cdot \nabla_r SPLS + \alpha_2 \cdot \nabla_r GS + \alpha_3 \cdot \nabla_r DLS \quad (10)$$

where $\nabla_r QS$ is the gradient of the quality score with respect to the current structure parameter value r, $\nabla_r SPLS$ is the gradient of the structure parameter likelihood score with respect to the current structure parameter value r, $\nabla_r GS$ is the gradient of the geometry score with respect to the current structure parameter value r, and $\nabla_r DLS$ is the gradient of the distance likelihood score with respect to the current structure parameter value r. Optionally a term for the physics score may also be included; optionally other terms, e.g. $\nabla_r GS$, may be omitted.

The system can use any appropriate computational methods to determine the gradients of the structure parameter likelihood score, the geometry score, the distance likelihood score, and the physics score with respect to the current structure parameter values. (Generally, each of these scores is a differentiable function of the structure parameter values). For example, to determine the gradients of the geometry score with respect to the current structure parameter values, the system can use a variation of the backpropagation algorithm which is typically used to determine the gradient with respect to the current weight values of a neural network. More specifically, the system can treat the weight values of the geometry neural network as constants and use backpropagation to determine the gradient of the geometry score with respect to the current structure parameter values that are provided as an input to the geometry neural network. As another example, to determine the gradients of the structure parameter likelihood score, the distance likelihood score, and the physics score, the system can use numerical differentiation methods (finite difference methods) or automatic differentiation methods (e.g., as implemented in the Tensor Flow software library).

The system updates the current structure parameter values using the gradient of the quality score with respect to the current structure parameter values (1108). In general, the system can update the current structure parameter values using the gradient of the quality score based on the update rule from any appropriate gradient descent optimization algorithm, for example, Adam, RMSprop, Adagrad, Adadelta, AdaMax, and L-BFGS amongst others. In some cases, the system can update the current structure parameter values using the gradient of the quality score based on a "warm" gradient descent update rule that includes "momentum". When the update rule includes momentum, the update to the current structure parameter values at the current iteration of the process 1100 is determined based in part on the update to the structure parameter values at the previous iteration of the process 1100. An example of a warm gradient descent update rule that includes momentum is described with reference to: R. M. Neal, "MCMC using Hamiltonian dynamics", Ch. 5, Handbook of Markov Chain Monte Carlo, Chapman & Hall/CRC Press, 2011. In this manner, the system can enable the current structure parameter values to "roll around" the quality score surface during optimization rather than directly finding a local minimum of the quality score surface. The quality score surface refers to the high-dimensional surface defined by the mapping from structure parameter values to the quality scores of predicted protein structures defined by the structure parameter values.

The system determines whether a termination criterion is satisfied (1110). For example, the system may determine the termination criterion is satisfied if the current structure parameter values have been updated at least a predetermined number of times (i.e., a predetermined number of iterations of the steps 1104, 1106, and 1108 have been performed). As another example, the system may determine the termination criterion is satisfied if the change in the current structure parameter values caused by updating the current structure parameter values (i.e., as described with reference to 1108) is less than a predetermined threshold.

In response to determining that the termination criterion is not met, the system can return to step 1104 and repeat the preceding steps. In response to determining that the termination criterion is met, the system can output the predicted structure defined by the current parameter values after the last update the current parameter values (1112). As described with reference to FIG. 9, the system can determine a final predicted structure of the protein by repeatedly performing the process 1100 to generate multiple predicted structures of the protein, and selecting the final predicted structure to be the generated predicted structure with the highest quality score.

Figure 12:
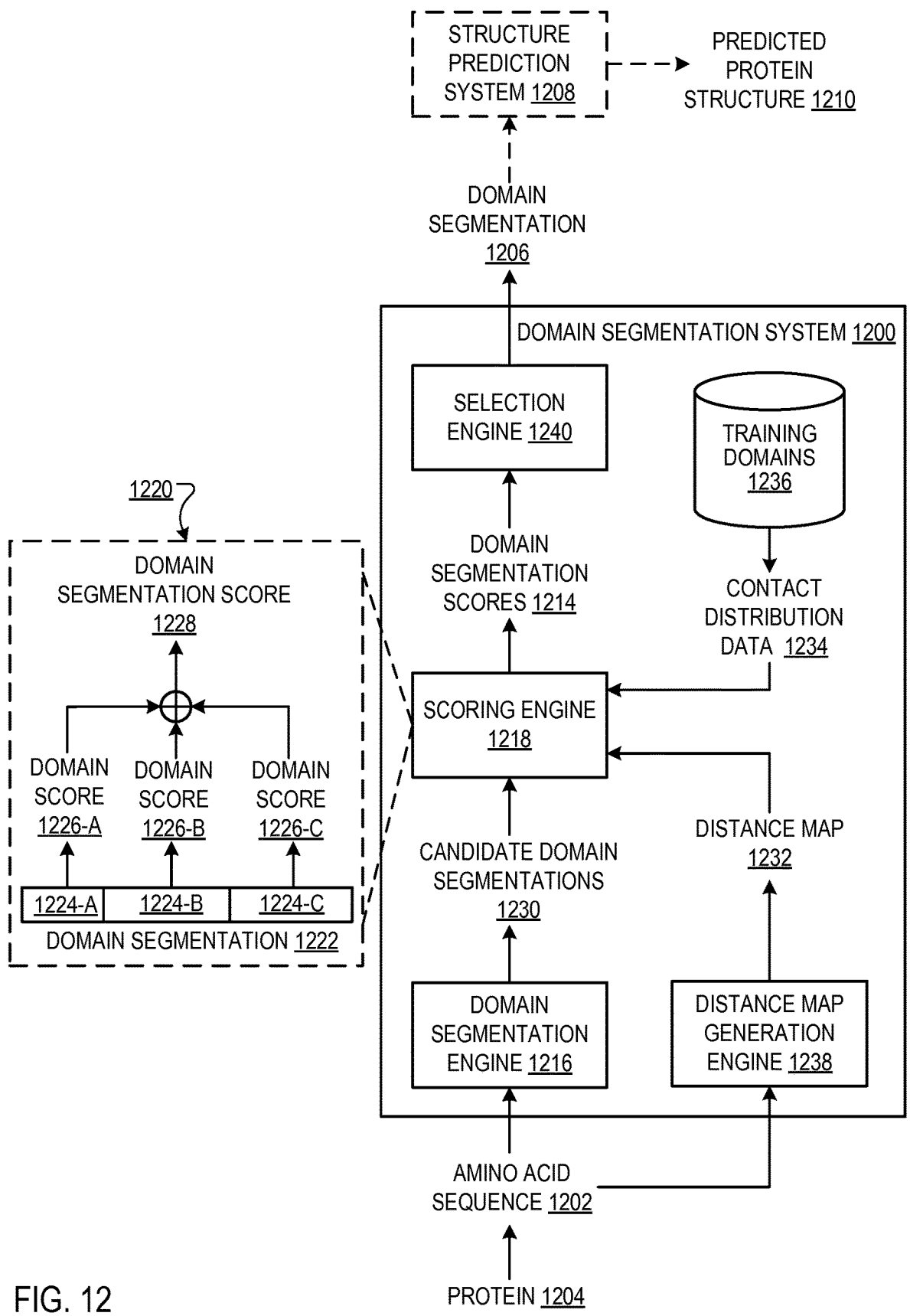
FIG. 12 is a block diagram of an example domain segmentation system.

FIG. 12 is a block diagram of an example domain segmentation system 1200. The domain segmentation system 1200 is an example of a system implemented as computer programs on one or more computers in one or more locations in which the systems, components, and techniques described below are implemented.

The domain segmentation system 1200 is configured to process data defining an amino acid sequence 1202 of a protein 1204 to generate a domain segmentation 1206 of the protein 1204. Each amino acid in the amino acid sequence 1202 is an organic compound which includes an amino functional group and a carboxyl functional group, as well as a side-chain (i.e., group of atoms) which is specific to the amino acid. Generally, a domain segmentation of a protein defines a partition of the amino acid sequence of the protein into multiple domains. A domain of a protein defines an amino acid subsequence of the amino acid sequence of the protein which can undergo protein folding (almost or totally) independently of the rest of the amino acid sequence of the protein. Moreover, protein domains can be independently stable, that is, can exist in a stable form independently of the rest of the protein. Protein folding refers to a physical process by which a sequence e.g. a random coil of amino acids (e.g., defined by the amino acid sequence 1202 of the protein 1204) folds into a unique three-dimensional configuration.

In a particular example, the amino acid sequence of a protein may be given by: [A, I, L, M, V, A, A, M, L], where A represents the amino acid alanine, I represents the amino acid isoleucine, L represents the amino acid leucine, M represents the amino acid methionine, and V represents the amino acid valine. An example domain segmentation of this protein may be given by: [A, I, L], [M, V, A, A], [M, L].

The domain segmentation 1206 generated by the system 100 for the protein 1204 can be provided to a structure prediction system 1208 which is configured to generate an output defining a predicted structure 1210 of the protein 1204. The structure prediction system 1208 can determine a predicted structure of each domain specified by the domain segmentation 1206, and subsequently determine a predicted structure of the entire protein 1204 by combining the predicted structures of each domain. Determining a predicted structure of a domain of the protein 1204 is generally an "easier" problem that determining a predicted structure of the entire protein 1204 at once. In particular, since the number of possible structures of an amino acid sequence increases exponentially with the length of the amino acid sequence, the search space of possible predicted structures of a domain will generally be exponentially smaller than the search space of possible predicted structures of the entire protein 1204. By separately determining a predicted structure of each domain of the protein 1204, the structure prediction system 1208 can generate more accurate predictions while consuming fewer computational resources (e.g., memory, computing power, or both) than if it directly predicted the structure of the entire protein 1204.

Examples of structure prediction systems, which can be used to generate a predicted structure of each domain of a protein, are described with reference to FIG. 1 and FIG. 9.

To generate the domain segmentation 1206, the system 1200 generates multiple candidate domain segmentations 1230 (which each specify multiple candidate domains of the protein 1204) and determines a respective domain segmentation score 1214 for each of the candidate domain segmentations 1230. As will be described in more detail below, the system 1200 subsequently uses the domain segmentation scores 1214 to select one of the candidate domain segmentations 1230 as the domain segmentation 1206 output by the system 1200.

The system 1200 generates the candidate domain segmentations 1230 using a domain segmentation engine 1216. In some implementations, the domain segmentation engine 1216 generates candidate domain segmentations 1230 corresponding to every possible domain segmentation of the protein 1204. In some other implementations, the domain segmentation engine 1216 generates candidate domain segmentations 1230 corresponding to a proper subset of the possible domain segmentations of the protein 1204 (e.g., by randomly sampling a predetermined number of possible domain segmentations of the protein 1204).

The system 1200 determines a respective domain segmentation score 1214 for each candidate domain segmentation 1230 using a scoring engine 1218. To determine the domain segmentation score 1214 for a candidate domain segmentation 1230, the scoring engine 1218 determines a respective domain score for each candidate domain defined by the candidate domain segmentation 1230. The scoring engine 1218 subsequently determines the domain segmentation score 1214 for the candidate domain segmentation 1230 using the respective domain scores for each candidate domain defined by the candidate domain segmentation 1230. For example, the scoring engine 1218 may determine the domain segmentation score 1214 for a candidate domain segmentation 1230 by summing the respective domain scores for each candidate domain defined by the candidate domain segmentation 1230.

In a particular example illustrated by 1220, the example domain segmentation 1222 defines a partition of the amino acid sequence of the protein 1204 into 3 domains: 1224-A, 1224-B, and 1224-C. The scoring engine 1218 determines the domain score 1226-A for the domain 1224-A, the domain score 1226-B for the domain 1224-B, and the domain score 1226-C for the domain 1224-C. The scoring engine 1218 determines the domain segmentation score 1228 for the example domain segmentation 1222 by summing the domain scores 1226-A, 1226-B, and 1226-C.

For each candidate domain defined by each candidate domain segmentation 1230, the scoring engine 1218 determines the domain score for the candidate domain using: (i) a distance map 1232, and (ii) contact distribution data 1234 derived from a set of training domains 1236, as will be described in more detail below.

The distance map 1232 characterizes estimated distances between each pair of amino acids in the protein 1204. The distance between a first amino acid and a second amino acid in the protein 1204 refers to a physical distance (e.g., measured in angstroms) between a particular atom (e.g., a carbon-alpha atom or carbon-beta atom) in the first amino acid and a particular e.g. corresponding atom in the second amino acid in the structure of the protein 1204. For example, for each pair of amino acids in the protein 1204, the distance map 1232 may include a respective binary variable which defines whether the distance between the pair of amino acids is predicted to be less than a predetermined threshold distance (e.g., 8 Angstroms). The system 1200 can generate the distance map 1232 by processing the amino acid sequence 1202 of the protein 1204 using a distance map generation engine 1238. An example process for generating a distance map 1232 is described below with reference to FIG. 14.

The training domains 1236 define actual (i.e., ground-truth) domains of respective training proteins (which are different than the protein 1204). The training domains 1236 can be manually determined by human experts (e.g., biologists trained to identify protein domains).

The system 1200 processes the training domains 1236 to generate contact distribution data 1234. The contact distribution data 1234 defines, for each given length in a predetermined number of possible lengths, a probability distribution over the number of contacts per amino acid in training domains of the given length. Two amino acids in a protein are said to be in contact if the distance separating the two amino acids is less than a predetermined threshold (e.g., 8 Angstroms). The number of contacts of a given amino acid in a domain refers to the number of other amino acids in the domain with which the given amino acid is in contact. The length of a domain refers to the number of amino acids in the amino acid subsequence defined by the domain. A probability distribution over the number of contacts per amino acid in training domains of a given length defines, for each of multiple non-negative integer values, a respective likelihood that a given amino acid in a training domain of the given length has a number of contacts in the training domain defined by the non-negative integer value.

For example, the contact distribution data 1234 may include data defining, for training domains of a given length, the mean and the standard deviation of the number of contacts per amino acid in training domains of the given length. The mean and the standard deviation define a Gaussian probability distribution over the number of contacts per amino acid in a training domain of the given length. In a particular example, the contact distribution data 1234 may specify that for training domains that are 20 amino acids long: (i) the mean number of contacts per amino acid in the training domain is 5, (ii) the standard deviation of the number of contacts per amino acid in the training domain is 1.8.

To determine the domain score for a candidate domain, the scoring engine 1218 obtains (from the distance map 1232) data characterizing the estimated distances between each pair of amino acids in the amino acid subsequence defined by the candidate domain. The scoring engine 1218 processes the data characterizing the estimated distances between each pair of amino acids in the amino acid subsequence defined by the candidate domain to determine the number of contacts per amino acid in the candidate domain. The scoring engine 1218 obtains, from the contact distribution data 1234, data defining a probability distribution over the number of contacts per amino acid in training domains of the same length as the candidate domain. Subsequently, the scoring engine 1218 determines the domain score for the candidate domain based on the likelihood of the number of contacts per amino acid in the candidate domain based on the probability distribution over the number of contacts per amino acid in training domains of the same length. Determining the domain score for a candidate domain is described in more detail below with reference to FIG. 13.

Optionally, the system 1200 may process the training domains 1236 to generate additional data characterizing: (i) the distribution of the lengths of the training domains, and (ii) the distribution of the number of training domains in each training protein. As will be described in more detail with reference to FIG. 13, the scoring system 1200 can determine the domain score for a candidate domain based in part on this additional data.

After generating a respective domain segmentation score 1214 for each of the candidate domain segmentations 1230, a selection engine 1240 selects one of the candidate domain segmentations 1230 as the domain segmentation 1206 output by the system 1200. For example, the selection engine 1240 may select the candidate domain segmentation 1230 with the highest domain segmentation score 1214 as the domain segmentation 1206 output by the system 1200.

Figure 13:
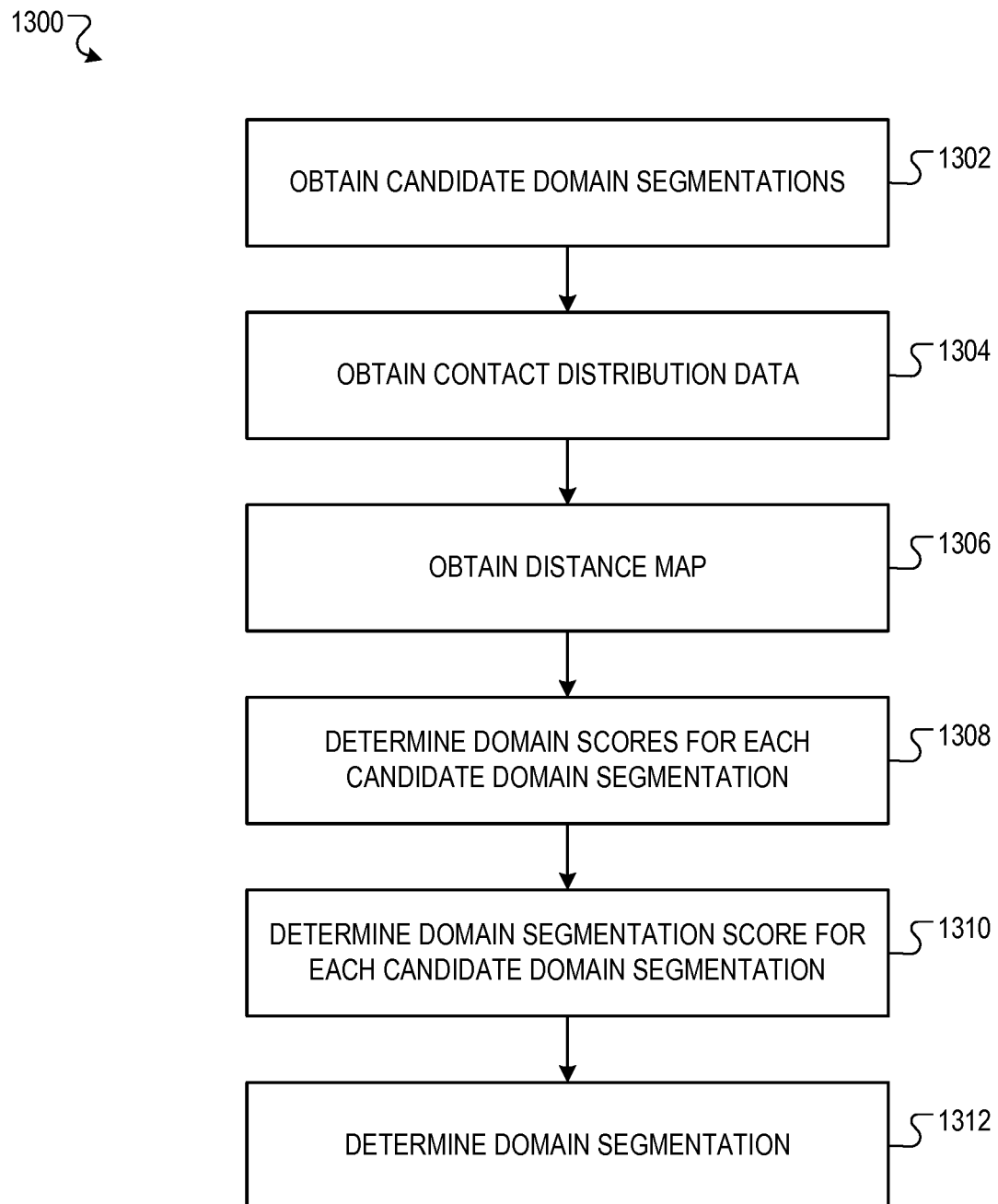
FIG. 13 is a flow diagram of an example process for determining a domain segmentation of an amino acid sequence of a protein.

FIG. 13 is a flow diagram of an example process 1300 for determining a domain segmentation of an amino acid sequence of a protein. For convenience, the process 1300 will be described as being performed by a system of one or more computers located in one or more locations. For example, a domain segmentation system, e.g., the domain segmentation system 1200 of FIG. 1200, appropriately programmed in accordance with this specification, can perform the process 1300.

The system obtains multiple candidate domain segmentations of the protein (1302). Each candidate domain segmentation defines a partition of the amino acid sequence of the protein into multiple respective candidate domains. In some implementations, the system generates candidate domain segmentations corresponding to every possible domain segmentation of the protein. In some other implementations, the system generates candidate domain segmentations corresponding to a proper subset of the possible domain segmentations of the protein (e.g., by randomly sampling a predetermined number of possible domain segmentations of the protein).

The system obtains data which defines, for each given length in a predetermined number of possible lengths, a probability distribution over the number of contacts per amino acid in training domains of the given length (1304). The system may obtain the data by processing a set of training domains, where each training domain defines an actual (i.e., ground truth) domain of a training protein. In a particular example, the system may determine the mean and standard deviation of the number of contacts per amino acid in training domains of the given length. More specifically, in this example the system may determine the mean and the standard deviation of a set of non-negative integer values which each define the number of contacts of a respective amino acid in a training domain of the given length. The mean and the standard deviation define a Gaussian probability distribution over the number of contacts per amino acid in a training domain of the given length.

Optionally, the system can process the set of training domains to determine additional data. For example, the system can determine data characterizing the distribution of the lengths of the training domains. In this example, the system may determine the mean and the standard deviation of the lengths of the training domains. As another example, the system can determine data characterizing the distribution of the number of training domains in each training protein. In this example, the system may determine the mean and the standard deviation of the number of training domains corresponding to each training protein.

The system obtains a distance map which characterizes estimated distances between each pair of amino acids in the protein (1306). For example, for each pair of amino acids in the protein, the distance map may include a respective binary variable which defines whether the pair of amino acids are predicted to be in contact. An example process for generating a distance map is described below with reference to FIG. 14.

The system determines a respective domain score for each candidate domain of each candidate domain segmentation (1308). To determine the domain score for a candidate domain, the system obtains (from the distance map) data characterizing the estimated distances between each pair of amino acids in the portion of the protein defined by the candidate domain. The system processes the data characterizing the estimated distances between each pair of amino acids in the amino acid subsequence defined by the candidate domain to determine the number of contacts per amino acid in the candidate domain. Subsequently, the system determines the domain score for the candidate domain based on the likelihood of the number of contacts per amino acid in the candidate domain based on the probability distribution over the number of contacts per amino acid in training domains of the same length.

For example, the probability distribution over the number of contacts per amino acid in training domains of the same length may be a Gaussian distribution defined by a mean and a standard deviation of the number of contacts per amino acid in training domains of the same length. In this example, the system can determine the domain score L for the candidate domain as:

$$L = \log \prod_{j=1}^{l} \mathcal{N}(d_j \mid \mu_l, \sigma_l) \qquad (11)$$

where $d_j$ is the number of contacts of the j-th amino acid in the candidate domain, l is the length of the candidate domain, $\mu_l$ is mean number of contacts per amino acid in training domains of length l, $\sigma_l$ is the standard deviation of the number of contacts per amino acid in training domains of length l, and $\mathcal{N}(d_j \mid \mu_l, \sigma_l)$ represents the probability of the value $d_j$ according to a Gaussian probability distribution parametrized by mean parameter $\mu_l$ and standard deviation parameter $\sigma_l$.

As another example, the system can additionally determine the domain score for the candidate domain based on the length of the candidate domain. In a particular example, the system can determine the domain score L for the candidate domain as:

$$L = \log \mathcal{N}(l \mid \mu^*, \sigma^*) + \log \prod_{j=1}^{l} \mathcal{N}(d_j \mid \mu_l, \sigma_l) \qquad (12)$$

where l is the length of the candidate domain, $\mu^*$ is the mean of the lengths of the training domains, $\sigma^*$ is the standard deviation of the lengths of the training domains, $\mathcal{N}(l \mid \mu^*, \sigma^*)$ represents the probability of the value l according to a Normal probability distribution parametrized by mean parameter $\mu^*$ and standard deviation parameter $\sigma^*$, and $\mathcal{N}(d \mid \mu_l, \sigma_l)$ is defined with reference to equation (11).

For each candidate domain segmentation, the system determines a domain segmentation score from the respective domain scores determined for the candidate domains defined by the candidate domain segmentation (1310). For example, the system may determine the domain segmentation score S for a candidate domain segmentation as:

$$S = \sum_{i=1}^{n} L_i \qquad (13)$$

where i indexes the n candidate domains defined by the candidate domain segmentation, and $L_i$ is the domain score determined for candidate domain i. As another example, the system can additionally determine the domain segmentation score S for a candidate domain segmentation based on the number of candidate domains defined by the candidate domain segmentation. In a particular example, the system can determine the domain segmentation score S for a candidate domain segmentation as:

$$S = \log \mathcal{N}(n \mid \hat{\mu}, \hat{\sigma}) + \sum_{i=1}^{n} L_i \qquad (14)$$

where n is the number of candidate domains defined by the candidate domain segmentation, $\hat{\mu}$ is the mean number of training domains in each training protein with the same length as the protein, $\hat{\sigma}$ is the standard deviation of the number of training domains in each training protein with the same length as the protein, $\mathcal{N}(n|\hat{\mu}, \hat{\sigma})$ represents the probability of the value n according to a Normal probability distribution parametrized by mean parameter $\hat{\mu}$ and standard deviation parameter $\hat{\sigma}$, and $\{L_i\}_{i=1}^n$ are defined with reference to equation (13).

The system determines the domain segmentation of the protein based on the respective domain segmentation scores determined for the candidate domain segmentations (1312). For example, the system may select the candidate domain segmentation with the highest domain segmentation score as the domain segmentation of the protein. After determining the domain segmentation of the protein, the system can provide the domain segmentation to a structure prediction system which is configured to generate an output defining a predicted structure of the protein using the domain segmentation.

Figure 14:
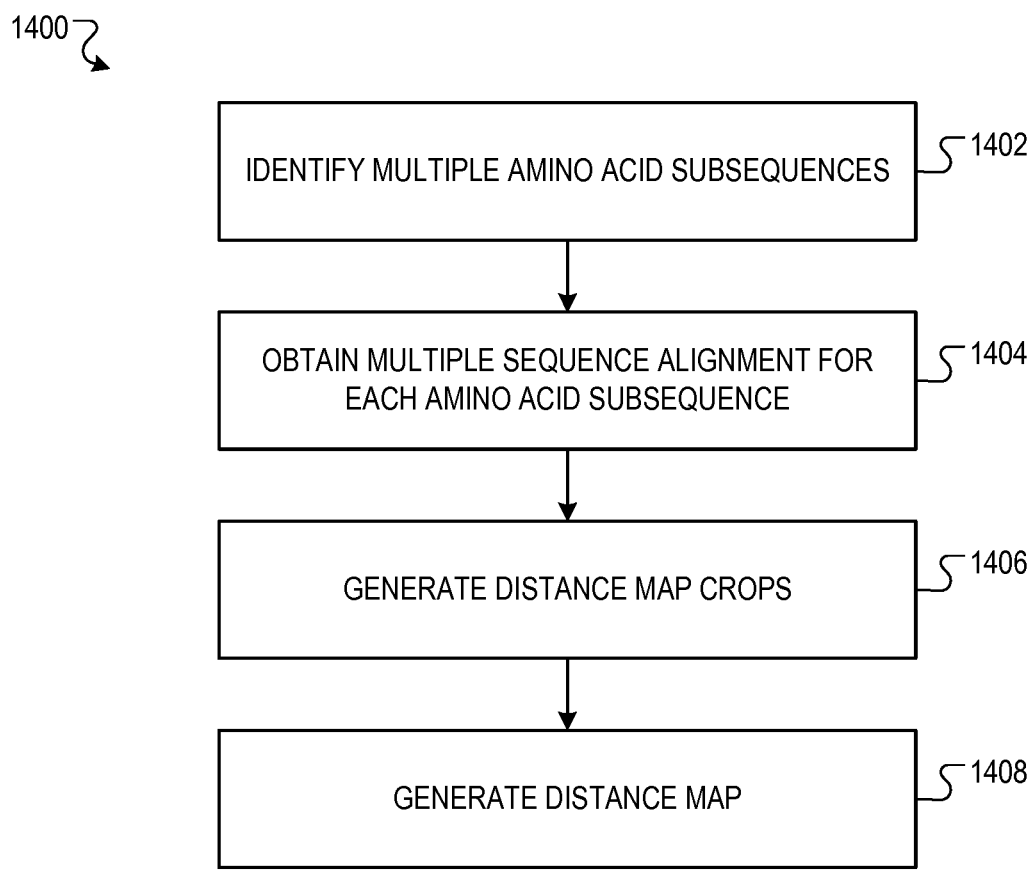
FIG. 14 is a flow diagram of an example process for generating a distance map characterizing estimated distances between each pair of amino acids in a protein.

FIG. 14 is a flow diagram of an example process 1400 for generating a distance map characterizing estimated distances between each pair of amino acids in a protein. For convenience, the process 1400 will be described as being performed by a system of one or more computers located in one or more locations. For example, a domain segmentation system, e.g., the domain segmentation system 1200 of FIG. 12, appropriately programmed in accordance with this specification, can perform the process 1400.

The system identifies multiple amino acid subsequences of the amino acid sequence of the protein (1402). In general, one of the amino acid subsequences identified by the system may be the full amino acid sequence of the protein. The multiple amino acid subsequences identified by the system typically "cover" the full amino acid sequence of the protein. That is, each amino acid in the protein is typically included in one or more amino acid subsequences identified by the system. In some implementations, the system randomly identifies the amino acid subsequences. For example, the system may randomly identify an amino acid subsequence by randomly selecting a starting point of the amino acid subsequence in the amino acid sequence of the protein, and randomly selecting a length of the amino acid subsequence. In these implementations, the system may continue randomly identifying amino acid subsequences until the collection of randomly identified amino acid subsequences covers the full amino acid sequence of the protein. In some other implementations, the system systematically identifies the amino acid subsequences. For example, for each of multiple different subsequence lengths (e.g., 64, 128, and 256 amino acids), the system may identify amino acid subsequences which have that length and are separated by a predetermined offset (e.g., 32 amino acids).

The system obtains a respective multiple sequence alignment (MSA) for each identified amino acid subsequence (1404). A MSA for amino acid subsequence of the protein refers to data defining a correspondence between the amino acid subsequence and amino acid (sub)sequences from each of multiple other proteins. A MSA can be generated for an amino acid subsequence of the protein by processing amino acid (sub)sequences from other proteins (e.g., which are stored in a database) using any appropriate computational sequence alignment technique (e.g., progressive alignment construction).

For each identified amino acid subsequence of the protein, the system processes the MSA obtained for the amino acid subsequence to generate a corresponding distance map crop (1406). A distance map crop corresponding to an amino acid subsequence of the protein refers to data characterizing estimated distances between each pair of amino acids in the amino acid subsequence of the protein. For example, a distance map crop corresponding to an amino acid subsequence of the protein may include a respective binary variable for each pair of amino acids in the amino acid subsequence which defines whether the pair of amino acids are predicted to be in contact. To generate a distance map crop corresponding to an amino acid subsequence, the system obtains features derived from the MSA corresponding to the amino acid subsequence. The features derived from the MSA can include a representation of the MSA itself, statistical features (e.g., second order statistical features) derived from the MSA such as those described with reference to: S. Seemayer, M. Gruber, and J. Soding: "CCMpred: fast and precise prediction of protein residue-residue contacts from correlated mutations", Bioinformatics, 2014, or both. The system can process the features derived from the MSA using a neural network to generate the distance map crop corresponding to the amino acid subsequence.

The system generates a distance map which characterizes estimated distances between each pair of amino acids in the protein using the distance map crops (1408). For example, the system may generate the distance map as a weighted average of the distance map crops, where the weight assigned to a distance map crop is based on the number of amino acid (sub)sequences in the MSA processed to generate the distance map crop. In a particular example, each of the distance map crops may include binary variables which indicate whether each pair of amino acids in the amino acid subsequence corresponding to the distance map crop are predicted to be in contact. For a given pair of amino acids in the protein, the system may determine a weighted average of the binary variables corresponding to the given pair of amino acids in each distance map crop and round the weighted average to 0 or 1 to generate a binary variable. Distance map crops which do not characterize the estimated distance between the given pair of amino acids are excluded from the weighted average.

Figure 15:
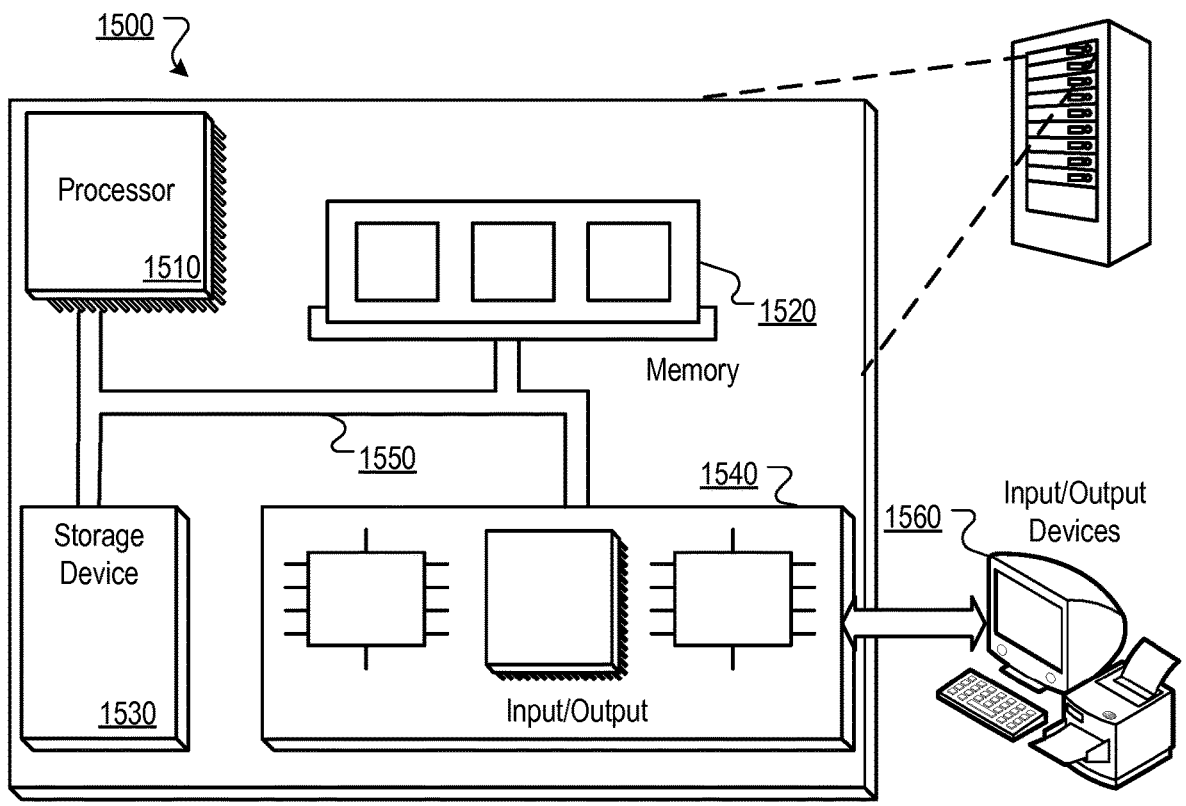
FIG. 15 is a block diagram of an example computing system.

FIG. 15 is block diagram of an example computer system 1500 that can be used to perform operations described above (e.g., the operations of a search computing unit, as described with reference to FIG. 1). The system 1500 includes a processor 1510, a memory 1520, a storage device 1530, and an input/output device 1540. Each of the components 1510, 1520, 1530, and 1540 can be interconnected, for example, using a system bus 1550. The processor 1510 is capable of processing instructions for execution within the system 1500. In one implementation, the processor 1510 is a single-threaded processor. In another implementation, the processor 1510 is a multi-threaded processor. The processor 1510 is capable of processing instructions stored in the memory 1520 or on the storage device 1530.

The memory 1520 stores information within the system 1500. In one implementation, the memory 1520 is a computer-readable medium. In one implementation, the memory 1520 is a volatile memory unit. In another implementation, the memory 1520 is a non-volatile memory unit.

The storage device 1530 is capable of providing mass storage for the system 1500. In one implementation, the storage device 1530 is a computer-readable medium. In various different implementations, the storage device 1530 can include, for example, a hard disk device, an optical disk device, a storage device that is shared over a network by multiple computing devices (e.g., a cloud storage device), or some other large capacity storage device.

The input/output device 1540 provides input/output operations for the system 1500. In one implementation, the input/output device 1540 can include one or more network interface devices, e.g., an Ethernet card, a serial communication device, e.g., and RS-232 port, and/or a wireless interface device, e.g., and 802.11 card. In another implementation, the input/output device can include driver devices configured to receive input data and send output data to other input/output devices, e.g., keyboard, printer and display devices 1560. Other implementations, however, can also be used, such as mobile computing devices, mobile communication devices, set-top box television client devices, etc.

Although an example processing system has been described in FIG. 15, implementations of the subject matter and the functional operations described in this specification can be implemented in other types of digital electronic circuitry, or in computer software, firmware, or hardware, including the structures disclosed in this specification and their structural equivalents, or in combinations of one or more of them.

Figures 16, 17:
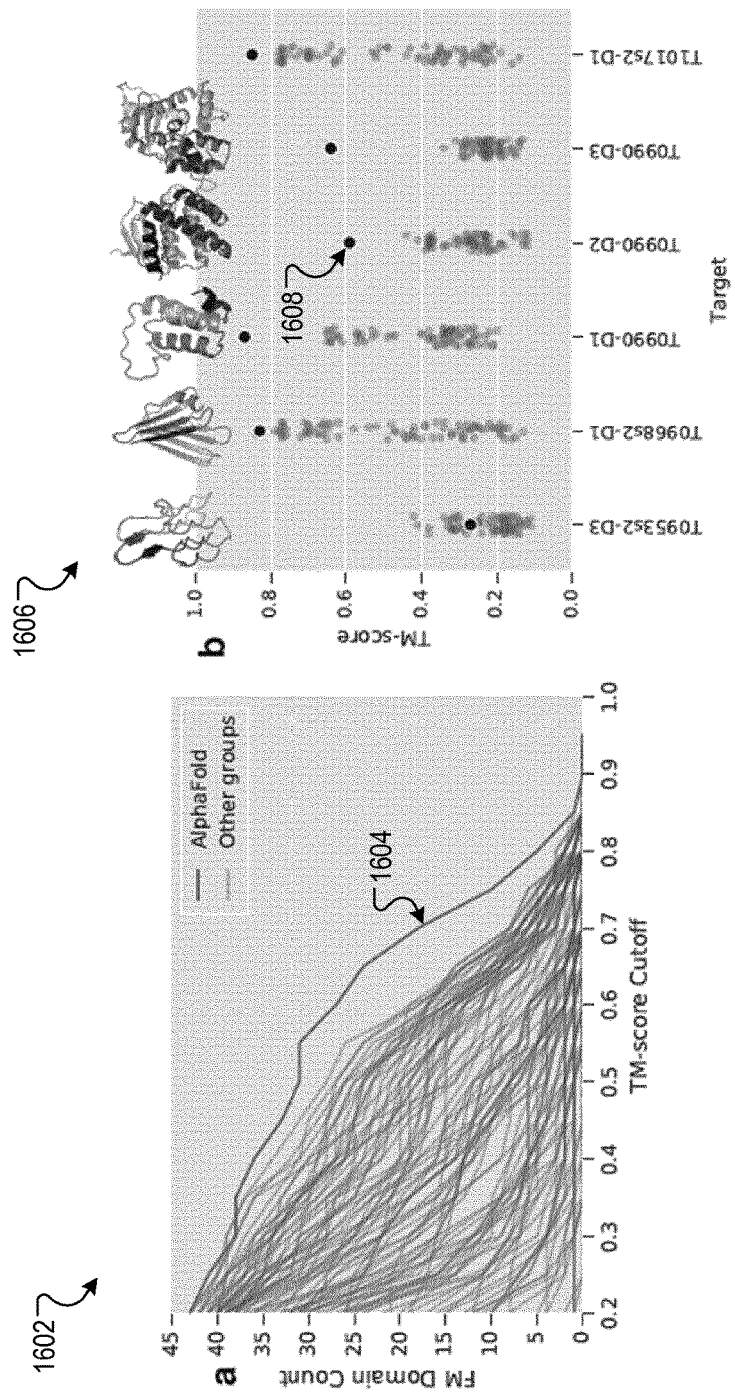
FIG. 16 shows example performance of a structure prediction system that uses an optimization system.
FIG. 17 shows example performance of a structure prediction system that uses a distance prediction system.

FIG. 16 illustrates an example of the performance gains that can be achieved by using a structure prediction system as described in this specification. In particular, FIG. 16 illustrates an example of the performance of the structure prediction system described with reference to FIG. 9 compared with the performance of other structure prediction systems submitted to the Critical Assessment of Protein Structure Prediction (CASP13) competition. The CASP13 competition is a blind assessment of the state of the field of protein structure prediction to benchmark progress in protein structure prediction accuracy.

The graph 1602 illustrates the number of free modeling (FM) protein domains predicted to given template modeling (TM) score thresholds by the structure prediction system described with reference to FIG. 9 (illustrated by the line 1604) and by the other structure prediction systems submitted to CASP13 (illustrated by the remaining lines). An FM protein domain refers to a domain where structures of similar protein domains have not been previously determined (e.g., by physical experiments). A TM score refers to a score between 0 and 1 that measures the degree of match of the backbone shape of a proposed structure of a protein to a native (i.e., actual) structure of the protein. It can be appreciated that the structure prediction system described with reference to FIG. 9 outperforms the other structure prediction systems for nearly all TM-score cutoffs.

The chart 1606 illustrates, for six newly determined protein structures (corresponding to the horizontal axis of the chart 1606), the TM score of the structure prediction generated by the structure prediction system described with reference to FIG. 9 (illustrated by dark circles, e.g., 1608) and the TM scores of the structure predictions generated by the other structure prediction systems submitted to CASP13 (illustrated by the light circles). It can be appreciated that the structure prediction system described with reference to FIG. 9 generally outperforms the other structure prediction systems.

FIG. 17 illustrates an example of the performance gains that can be achieved by using the distance prediction system described with reference to FIG. 6. The table 1700 shows the precisions for long-range contact prediction in CASP13 for the most probable L, L/2, or L/5 amino acid residue contacts, where L is the length of the domain. The probability distributions over distance ranges between pairs of amino acids that are generated by the distance prediction system described with reference to FIG. 6 (AF) are thresholded to contact predictions, and are compared with submissions by the two best-ranked contact prediction methods in CASP13: 032 (TripletRes) and 498 (RaptorX-Contact). Table 1700 illustrates the contact prediction accuracy of the distance prediction system described with reference to FIG. 6 for free modeling (FM) protein domains, template-based modeling (TBM) protein domains (where a protein domain with a similar sequence has a known structure), and intermediate FM/TBM protein domains. It can be appreciated that the distance prediction system described with reference to FIG. 6 generally outperforms the other contact prediction systems.

Figure 18:
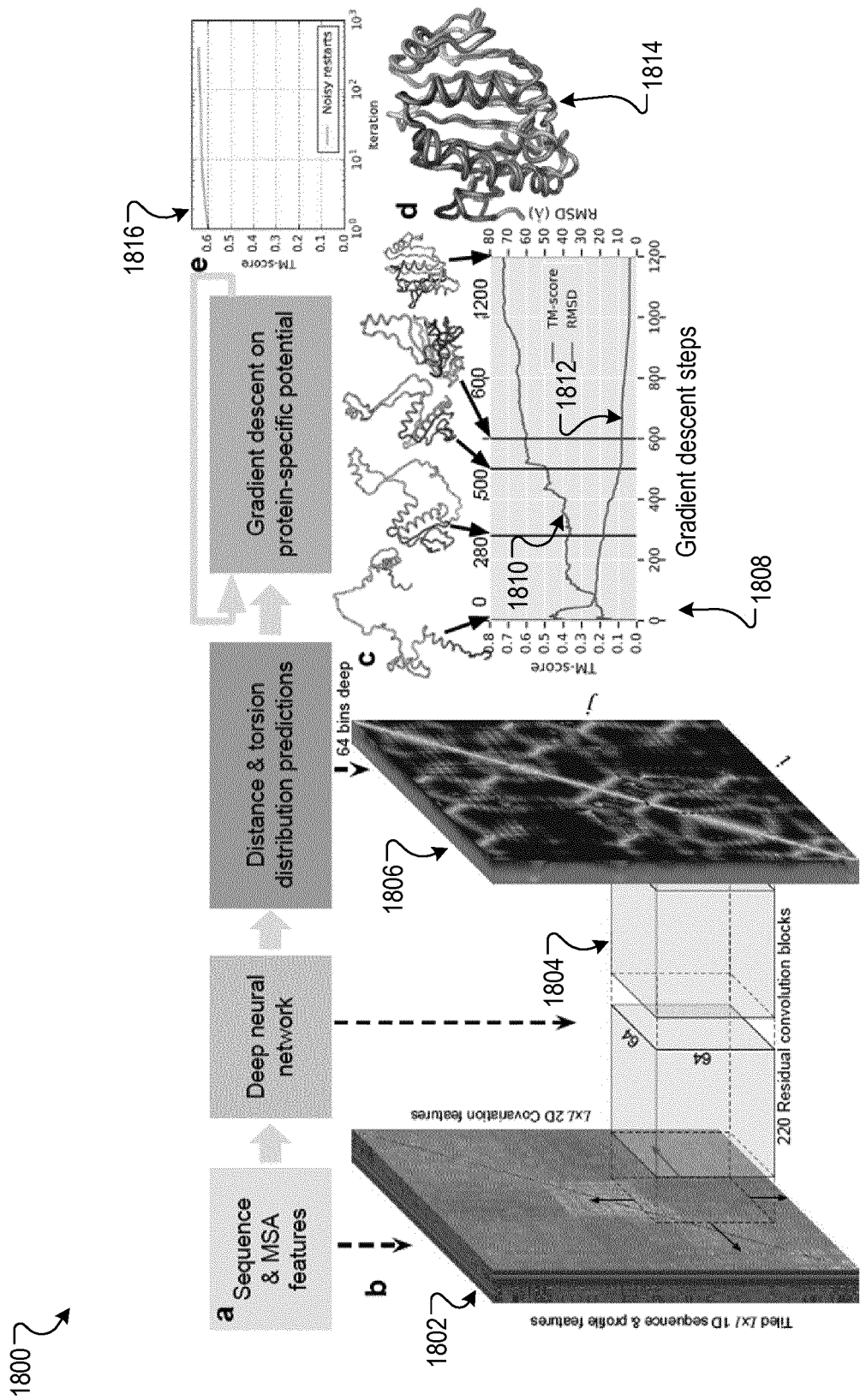
FIG. 18 shows an example data flow for determining the predicted structure of a protein.

FIG. 18 is an illustration of an example data flow 1800 for determining the predicted structure of a protein, e.g., using the structure prediction system described with reference to FIG. 9.

L×L 2D covariance features and tiled L×1 1D sequence and profile features (where L is the length of the amino acid sequence) are concatenated to generate the sequence and MSA features 1802. The sequence and MSA features can be represented as a 3D array of numerical values.

64×64 crops from the features 1802 are processed using a distance prediction neural network 1804 with 220 residual convolutional blocks (e.g., as described with reference to FIG. 6) to generate crops of the full distance map 1806. The crops of the full distance map are fused (e.g., averaged) to generate the full distance map 1806. The full distance map may specify a respective probability distribution over 64 possible distance ranges between each pair of amino acids in the protein. A separate output head of the distance prediction neural network 1804 generates structure parameter distributions (e.g., torsion angle distributions) for each amino acid in the protein (i.e., in this example, the structure prediction network and the distance prediction network share some parameter values).

Initial values of structure parameters defining a predicted structure of the protein are updated over multiple iterations of gradient descent to generate a final predicted structure of the protein. At each iteration, a quality score of the predicted structure defined by the current values of the structure parameters is determined based on (i) the distance map 1806, (ii) the structure parameter distributions, and (iii) a physics score based on a van der Waals potential that characterizes the interatomic potential energy associated with the predicted structure. The quality score is differentiable with respect to the current values of the structure parameters, and gradients of the quality score are determined with respect to the current values of the structure parameters. A gradient descent optimization technique is used to adjust the current values of the structure parameters using the gradients of the quality score to determine updated values of the structure parameters.

The graph 1808 illustrates the TM score 1810 and the RMSD 1812 between the predicted structure and the actual structure of the protein at each gradient descent step. It can be appreciate that the predicted structure of the protein approximates the actual structure of the protein more accurately over the sequence of gradient descent steps. It can be appreciated from the 3D visualization 1814 of an overlay of (i) the predicted structure of the protein after the last gradient descent step and (ii) the actual structure of the protein, that the final predicted structure of the protein accurately approximates the actual structure of the protein.

The graph 1816 illustrates the improvements in TM score that can be achieved by performing the gradient descent procedure multiple times with different initializations to generate different predicted structures, and selecting the best predicted structure as the final predicted structure of the protein.

FIG. 19 illustrates aspects of a distance map generated the distance prediction system described with reference to FIG. 6 for the protein 1900. The illustration 1902 is a distance map showing the actual (i.e., native) inter-residue distances for the protein 1900. The illustration 1904 is a distance map that is generated using the distance prediction system and that shows the modes of the probability distributions over inter-residue distance ranges for the protein 1900. It can be appreciated that the predicted distance map 1904 is an accurate approximation of the actual distance map 1902. The illustration 1906 shows the predicted probability distributions over possible distance ranges between residue 29 and all other residues of the protein 1900. The graph 1908 plots the mode of the predicted distance distribution against the true distance for all residue pairs in the protein 1900 with distances≤22 A, excluding distributions with standard deviation>3.5 A. The error bars show the mean and standard deviation calculated for 1 A bins. The graph 1910 plots the error of the mode distance prediction against the standard deviation of the distance distributions, excluding residue pairs with native distances>22 A.

Figure 20:
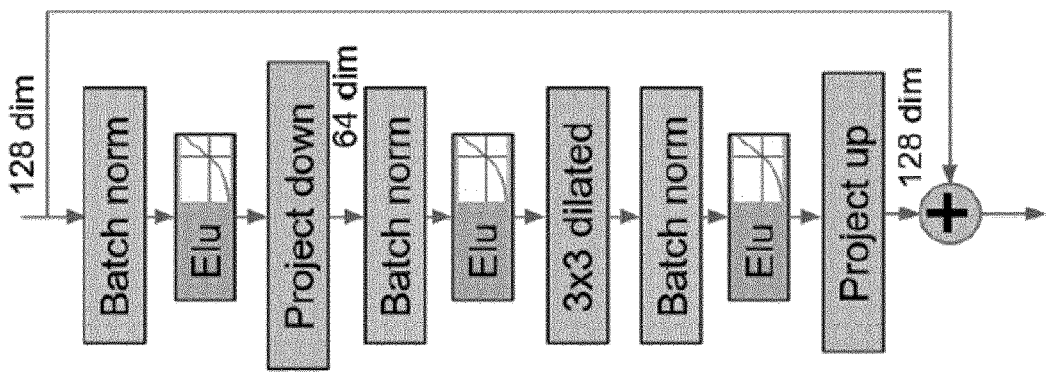
FIG. 20 shows an example architecture of a residual block of a distance prediction neural network.

FIG. 20 illustrates an example architecture 2000 of a residual block of the distance prediction neural network (e.g., as described with reference to FIG. 6). The residual block consists of a sequence of neural network layers, interleaving three batchnorm layers, two 1×1 projection layers, a 3×3 dilated convolutional layer, and ELU non-linearities. Successive layers cycle through dilations of 1, 2, 4, and 8 pixels to allow propagation of information quickly across the cropped region of the sequence and MSA features. In one example architecture, the distance prediction neural network may include a sequence of 220 such residual blocks. After the last residual block, the distance prediction neural network may include an output layer that has a respective soft-max function corresponding to each i, j component of the distance map crop generated by the distance prediction neural network.

Figure 21:
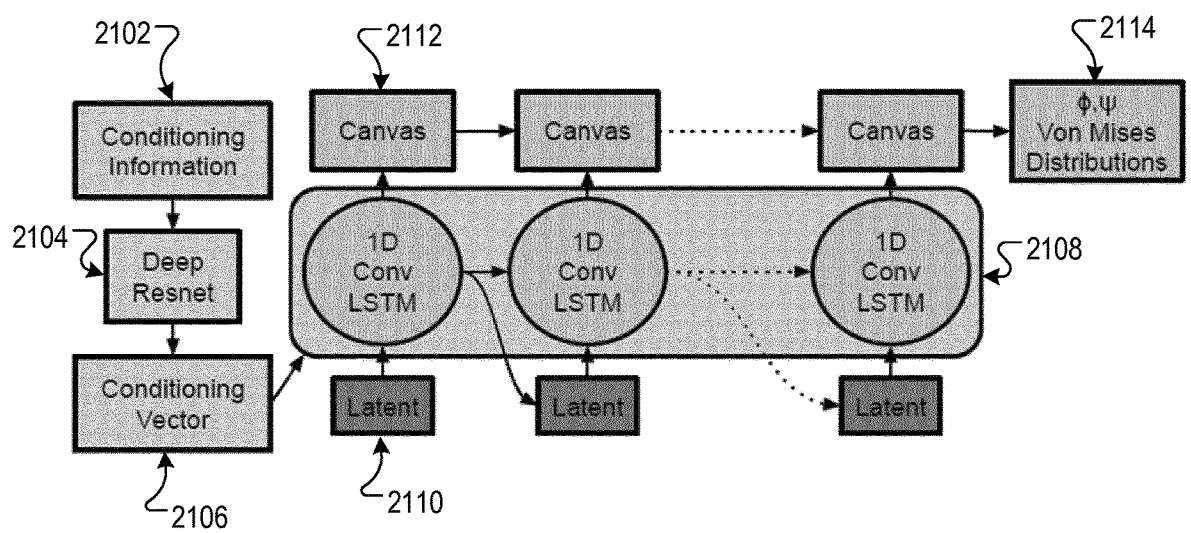
FIG. 21 shows an example architecture of a DRAW generative neural network configured to generate protein structure fragments.

FIG. 21 is an illustration of an example architecture of a DRAW generative neural network 2100 that is configured to generate protein structure fragments, as described with reference to FIG. 4. The generative neural network 2100 processes 2-D conditioning information 2102 that includes sequence and MSA features of an amino acid sequence (e.g., a subsequence of a longer amino acid sequence of a protein) using an embedding neural network 2104 to generate a conditioning vector 2106. The embedding neural network 2104 may include one or more convolutional residual blocks (e.g., as described with reference to FIG. 20) followed by a mean pooling layer that outputs the conditioning vector 2106. The conditioning vector 2106 is then passed into a 1-D convolutional long short-term memory (LSTM) convolutional decoder subnetwork 2108.

At each of 128 internal time steps, the decoder subnetwork 2108 samples a latent variable from a latent space 2110 in accordance with a prior probability distribution over the latent space 2110 and processes the latent variable and the conditioning vector 2106 to update an internal state of the decoder subnetwork. The prior probability distribution may be, e.g., a standard Normal distribution over the latent space 2110. At each internal time step, the generative neural network 2100 may add the updated internal state of the decoder subnetwork 2108 at the time step to the "canvas" internal state 2112 of the generative neural network 2100.

After a final internal time step, the values of the canvas internal state 2112 of the generative neural network 2100 define respective probability distributions 2114 (e.g., von Mises distributions) corresponding to each structure parameter of a protein structure fragment. Structure parameter values for any desired number of protein structure fragments can thereafter be sampled in accordance with the probability distributions 2114 over the structure parameter values.

This specification uses the term "configured" in connection with systems and computer program components. For a system of one or more computers to be configured to perform particular operations or actions means that the system has installed on it software, firmware, hardware, or a combination of them that in operation cause the system to perform the operations or actions. For one or more computer programs to be configured to perform particular operations or actions means that the one or more programs include instructions that, when executed by data processing apparatus, cause the apparatus to perform the operations or actions.

Embodiments of the subject matter and the functional operations described in this specification can be implemented in digital electronic circuitry, in tangibly-embodied computer software or firmware, in computer hardware, including the structures disclosed in this specification and their structural equivalents, or in combinations of one or more of them. Embodiments of the subject matter described in this specification can be implemented as one or more computer programs, i.e., one or more modules of computer program instructions encoded on a tangible non-transitory storage medium for execution by, or to control the operation of, data processing apparatus. The computer storage medium can be a machine-readable storage device, a machine-readable storage substrate, a random or serial access memory device, or a combination of one or more of them. Alternatively or in addition, the program instructions can be encoded on an artificially-generated propagated signal, e.g., a machine-generated electrical, optical, or electromagnetic signal, that is generated to encode information for transmission to suitable receiver apparatus for execution by a data processing apparatus.

The term "data processing apparatus" refers to data processing hardware and encompasses all kinds of apparatus, devices, and machines for processing data, including by way of example a programmable processor, a computer, or multiple processors or computers. The apparatus can also be, or further include, special purpose logic circuitry, e.g., an FPGA (field programmable gate array) or an ASIC (application-specific integrated circuit). The apparatus can optionally include, in addition to hardware, code that creates an execution environment for computer programs, e.g., code that constitutes processor firmware, a protocol stack, a database management system, an operating system, or a combination of one or more of them.

A computer program, which may also be referred to or described as a program, software, a software application, an app, a module, a software module, a script, or code, can be written in any form of programming language, including compiled or interpreted languages, or declarative or procedural languages; and it can be deployed in any form, including as a stand-alone program or as a module, component, subroutine, or other unit suitable for use in a computing environment. A program may, but need not, correspond to a file in a file system. A program can be stored in a portion of a file that holds other programs or data, e.g., one or more scripts stored in a markup language document, in a single file dedicated to the program in question, or in multiple coordinated files, e.g., files that store one or more modules, sub-programs, or portions of code. A computer program can be deployed to be executed on one computer or on multiple computers that are located at one site or distributed across multiple sites and interconnected by a data communication network.

In this specification the term "engine" is used broadly to refer to a software-based system, subsystem, or process that is programmed to perform one or more specific functions. Generally, an engine will be implemented as one or more software modules or components, installed on one or more computers in one or more locations. In some cases, one or more computers will be dedicated to a particular engine; in other cases, multiple engines can be installed and running on the same computer or computers.

The processes and logic flows described in this specification can be performed by one or more programmable computers executing one or more computer programs to perform functions by operating on input data and generating output. The processes and logic flows can also be performed by special purpose logic circuitry, e.g., an FPGA or an ASIC, or by a combination of special purpose logic circuitry and one or more programmed computers.

Computers suitable for the execution of a computer program can be based on general or special purpose microprocessors or both, or any other kind of central processing unit. Generally, a central processing unit will receive instructions and data from a read-only memory or a random access memory or both. The essential elements of a computer are a central processing unit for performing or executing instructions and one or more memory devices for storing instructions and data. The central processing unit and the memory can be supplemented by, or incorporated in, special purpose logic circuitry. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device, e.g., a universal serial bus (USB) flash drive, to name just a few.

Computer-readable media suitable for storing computer program instructions and data include all forms of nonvolatile memory, media and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks.

To provide for interaction with a user, embodiments of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's device in response to requests received from the web browser. Also, a computer can interact with a user by sending text messages or other forms of message to a personal device, e.g., a smartphone that is running a messaging application, and receiving responsive messages from the user in return.

Data processing apparatus for implementing machine learning models can also include, for example, special-purpose hardware accelerator units for processing common and compute-intensive parts of machine learning training or production, i.e., inference, workloads.

Machine learning models can be implemented and deployed using a machine learning framework, e.g., a TensorFlow framework, a Microsoft Cognitive Toolkit framework, an Apache Singa framework, or an Apache MXNet framework.

Embodiments of the subject matter described in this specification can be implemented in a computing system that includes a back-end component, e.g., as a data server, or that includes a middleware component, e.g., an application server, or that includes a front-end component, e.g., a client computer having a graphical user interface, a web browser, or an app through which a user can interact with an implementation of the subject matter described in this specification, or any combination of one or more such back-end, middleware, or front-end components. The components of the system can be interconnected by any form or medium of digital data communication, e.g., a communication network. Examples of communication networks include a local area network (LAN) and a wide area network (WAN), e.g., the Internet.

The computing system can include clients and servers. A client and server are generally remote from each other and typically interact through a communication network. The relationship of client and server arises by virtue of computer programs running on the respective computers and having a client-server relationship to each other. In some embodiments, a server transmits data, e.g., an HTML page, to a user device, e.g., for purposes of displaying data to and receiving user input from a user interacting with the device, which acts as a client. Data generated at the user device, e.g., a result of the user interaction, can be received at the server from the device.

While this specification contains many specific implementation details, these should not be construed as limitations on the scope of any invention or on the scope of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially be claimed as such, one or more features from a claimed combination can in some cases be excised from the combination, and the claimed combination may be directed to a subcombination or variation of a subcombination.

Similarly, while operations are depicted in the drawings and recited in the claims in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described above should not be understood as requiring such separation in all embodiments, and it should be understood that the described program components and systems can generally be integrated together in a single software product or packaged into multiple software products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In some cases, multitasking and parallel processing may be advantageous.

What is claimed is:

1. A computer-implemented method comprising:
    determining a predicted structure of a protein, comprising:
        generating a distance map for the protein, wherein the protein comprises a sequence of amino acid residues, and the distance map characterizes estimated distances between amino acid residues in the predicted structure of the protein, wherein generating the distance map for the protein comprises:
            generating a plurality of distance map crops, wherein each distance map crop characterizes estimated distances between (i) amino acid residues in each of one or more respective first positions in the sequence and (ii) amino acid residues in each of one or more respective second positions in the sequence in the structure of the protein, wherein generating a distance map crop comprises:
                identifying one or more first positions in the sequence and one or more second positions in the sequence, wherein the first positions are a proper subset of the sequence;
                determining a network input from the amino acid residues in the first positions in the sequence and the amino acid residues in the second positions in the sequence; and
                providing the network input to a distance prediction neural network, wherein the distance prediction neural network is configured to process the network input in accordance with current values of distance prediction neural network weights to generate a network output comprising the distance map crop, wherein each distance map crop is a two dimensional (2D) array that is a proper subset of the distance map; and
            generating the distance map for the protein by fusing the plurality of distance map crops; and
        determining the predicted structure of the protein using the distance map for the protein.

2. The method of claim 1, wherein determining a network input from the amino acid residues in the first positions in the sequence and the amino acid residues in the second positions in the sequence comprises:
    extracting components of (i) a representation of the sequence of amino acid residues, and (ii) alignment features derived from a multiple sequence alignment which includes the sequence of amino acid residues, which correspond to the amino acid residues in the first positions in the sequence and the amino acid residues in the second positions in the sequence.

3. The method of claim 1, wherein identifying one or more first positions in the sequence and one or more second positions in the sequence comprises:
    stochastically sampling the first positions as a first sequence of consecutive positions of a first predetermined length; and
    stochastically sampling the second positions as a second sequence of consecutive positions of a second predetermined length.

4. The method of claim 1, wherein generating the distance map for the given protein using the plurality of distance map crops comprises:
    averaging the plurality of distance map crops.

5. The method of claim 1, wherein generating the distance map for the protein using the plurality of distance map crops comprises:
    processing the plurality of distance map crops using a fusing neural network in accordance with current values of fusing neural network parameters to generate an output comprising the distance map.

6. The method of claim 1, wherein each distance map crop defines, for each pair of amino acid residues including a first amino acid residue in a first position and a second amino acid residue in a second position, a respective probability distribution over a predetermined set of distance ranges between the pair of amino acid residues.

7. The method of claim 1, wherein each distance map crop defines, for each pair of amino acid residues including a first amino acid residue in a first position and a second amino acid residue in a second position, a binary variable indicating whether a distance between the pair of amino acids is less than a predetermined threshold.

8. The method of claim 1, wherein each distance map crop defines, for each pair of amino acid residues including a first amino acid residue in a first position and a second amino acid residue in a second position, a continuous-valued number defining a distance between the pair of amino acids.

9. The method of claim 1, wherein the distance prediction neural network is trained on a set of training data comprising a plurality of training examples, wherein each training example comprises: (i) a training network input determined from a sequence of amino acid residues in a training protein, and (ii) a target distance map, wherein the target distance map characterizes actual distances between the amino acid residues in the training protein.

10. The method of claim 1, wherein the distance prediction neural network is trained on a set of training data comprising a plurality of training examples, wherein each training example comprises: (i) a training network input determined from a sequence of amino acid residues in a training protein, and (ii) a target distance map, wherein the target distance map characterizes estimated distances between the amino acid residues in the training protein and is generated as an output of a teacher neural network by processing the training network input.

11. The method of claim 9, wherein for a plurality of the training examples, random noise is added to the target distance map.

12. The method of claim 1, wherein the distance prediction neural network comprises one or more dilated convolutional neural network layers, one or more residual blocks, one or more attention layers, or a combination thereof.

13. The method of claim 11, wherein the distance prediction neural network is trained to generate an auxiliary output characterizing a secondary structure of the amino acid residues in the first positions in the sequence and the amino acid residues in the second positions in the sequence.

14. The method of claim 1, wherein the distance prediction neural network is trained to generate an auxiliary output characterizing torsion angles between amino acid residues in the first positions in the sequence and amino acid residues in the second positions in the sequence.

15. The method of claim 1, further comprising determining a predicted structure of the protein, wherein the predicted structure of the given protein is defined by values of a plurality of structure parameters, the determining comprising:
obtaining initial values of the plurality of structure parameters defining the predicted structure;
updating the initial values of the plurality of structure parameters, comprising, at each of a plurality of update iterations:
determining a quality score characterizing a quality of the predicted structure defined by current values of the structure parameters using the distance map;
for one or more of the plurality of structure parameters:
optimizing the quality score by adjusting the current value of the structure parameter;
determining the predicted structure of the protein to be defined by the current values of the plurality of structure parameters after a final update iteration of the plurality of update iterations.

16. A system comprising one or more computers and one or more storage devices storing instructions that when executed by the one or more computers cause the one or more computers to perform operations comprising:
determining a predicted structure of a protein, comprising:
generating a distance map for the protein, wherein the protein comprises a sequence of amino acid residues, and the distance map characterizes estimated distances between amino acid residues in the predicted structure of the protein,
generating a plurality of distance map crops, wherein each distance map crop characterizes estimated distances between (i) amino acid residues in each of one or more respective first positions in the sequence and (ii) amino acid residues in each of one or more respective second positions in the sequence in the structure of the protein, wherein generating a distance map crop comprises:
identifying one or more first positions in the sequence and one or more second positions in the sequence, wherein the first positions are a proper subset of the sequence;
determining a network input from the amino acid residues in the first positions in the sequence and the amino acid residues in the second positions in the sequence; and
providing the network input to a distance prediction neural network, wherein the distance prediction neural network is configured to process the network input in accordance with current values of distance prediction neural network weights to generate a network output comprising the distance map crop, wherein each distance map crop is a two-dimensional (2D) array that is a proper subset of the distance map; and
generating the distance map for the protein by fusing the plurality of distance map crops; and
determining the predicted structure of the protein using the distance map for the protein.

17. One or more non-transitory computer storage media storing instructions that when executed by one or more computers cause the one or more computers to perform operations comprising:
determining a predicted structure of a protein, comprising:
generating a distance map for the protein, wherein the protein comprises a sequence of amino acid residues, and the distance map characterizes estimated distances between amino acid residues in the predicted structure of the protein,
generating a plurality of distance map crops, wherein each distance map crop characterizes estimated distances between (i) amino acid residues in each of one or more respective first positions in the sequence and (ii) amino acid residues in each of one or more respective second positions in the sequence in the structure of the protein, wherein generating a distance map crop comprises:
identifying one or more first positions in the sequence and one or more second positions in the sequence, wherein the first positions are a proper subset of the sequence;
determining a network input from the amino acid residues in the first positions in the sequence and the amino acid residues in the second positions in the sequence; and
providing the network input to a distance prediction neural network, wherein the distance prediction neural network is configured to process the network input in accordance with current values of distance prediction neural network weights to generate a network output comprising the distance map crop, wherein each distance map crop is a two-dimensional (2D) array that is a proper subset of the distance map; and
generating the distance map for the protein by fusing the plurality of distance map crops; and
determining the predicted structure of the protein using the distance map for the protein.

18. The non-transitory computer storage media of claim 17, wherein determining a network input from the amino acid residues in the first positions in the sequence and the amino acid residues in the second positions in the sequence comprises:
extracting components of (i) a representation of the sequence of amino acid residues, and (ii) alignment features derived from a multiple sequence alignment which includes the sequence of amino acid residues, which correspond to the amino acid residues in the first positions in the sequence and the amino acid residues in the second positions in the sequence.

19. The non-transitory computer storage media of claim 17, wherein identifying one or more first positions in the sequence and one or more second positions in the sequence comprises:
stochastically sampling the first positions as a first sequence of consecutive positions of a first predetermined length; and
stochastically sampling the second positions as a second sequence of consecutive positions of a second predetermined length.

20. The non-transitory computer storage media of claim 17, wherein generating the distance map for the protein using the plurality of distance map crops comprises:
 averaging the plurality of distance map crops.

* * * * *